(12) United States Patent
Lee et al.

(10) Patent No.: US 11,945,864 B2
(45) Date of Patent: Apr. 2, 2024

(54) MONOCLONAL ANTIBODY SPECIFICALLY BINDING TO LAG-3 AND USE THEREOF

(71) Applicant: Y-BIOLOGICS INC., Daejeon (KR)

(72) Inventors: Sang Pil Lee, Daejeon (KR); Ji-Young Shin, Daejeon (KR); Sunha Yoon, Daejeon (KR); Yunseon Choi, Daejeon (KR); Jae Eun Park, Daejeon (KR); Ji Su Lee, Daejeon (KR); Youngja Song, Daejeon (KR); Gisun Baek, Daejeon (KR); Seok Ho Yoo, Daejeon (KR); Yeung-chul Kim, Daejeon (KR); Dong Jung Lee, Daejeon (KR); Bum-Chan Park, Daejeon (KR); Young Woo Park, Daejeon (KR)

(73) Assignee: Y-BIOLOGICS INC., Daejeon (KR)

( * ) Notice: Subject to any disclaimer, the term of this patent is extended or adjusted under 35 U.S.C. 154(b) by 618 days.

(21) Appl. No.: 17/051,630

(22) PCT Filed: Jun. 28, 2019

(86) PCT No.: PCT/KR2019/007877
§ 371 (c)(1),
(2) Date: Oct. 29, 2020

(87) PCT Pub. No.: WO2020/005003
PCT Pub. Date: Jan. 2, 2020

(65) Prior Publication Data
US 2021/0238283 A1   Aug. 5, 2021

(30) Foreign Application Priority Data

Jun. 29, 2018   (KR) .................. 10-2018-0075581

(51) Int. Cl.
| | |
|---|---|
| C07K 16/28 | (2006.01) |
| A61K 39/00 | (2006.01) |
| A61K 45/06 | (2006.01) |
| A61K 47/68 | (2017.01) |
| G01N 33/574 | (2006.01) |

(52) U.S. Cl.
CPC .......... *C07K 16/2803* (2013.01); *A61K 45/06* (2013.01); *A61K 47/6849* (2017.08); *G01N 33/574* (2013.01); *A61K 2039/505* (2013.01); *C07K 2317/31* (2013.01); *C07K 2317/565* (2013.01); *C07K 2319/03* (2013.01)

(58) Field of Classification Search
CPC ............ C07K 16/2803; C07K 2317/31; C07K 2317/565; C07K 2319/03; C07K 2317/21; C07K 2317/33; C07K 2317/34; C07K 2317/622; C07K 2317/76; C07K 2317/92; C07K 14/705; C07K 16/2818; C07K 16/2827; C07K 2317/24; C07K 2317/56; A61K 45/06; A61K 47/6849; A61K 2039/505; G01N 33/574; G01N 2333/70503; A61P 35/00
See application file for complete search history.

(56) References Cited

U.S. PATENT DOCUMENTS

| | | |
|---|---|---|
| 2015/0259420 A1 | 9/2015 | Triebel et al. |
| 2017/0101472 A1 | 4/2017 | Ullman et al. |

FOREIGN PATENT DOCUMENTS

| | | |
|---|---|---|
| WO | WO 88/01649 A1 | 3/1988 |
| WO | WO 2010/019570 A2 | 2/2010 |
| WO | WO 2014/008218 A1 | 1/2014 |
| WO | WO 2015/042246 A1 | 3/2015 |
| WO | WO 2015/138920 A1 | 9/2015 |
| WO | WO 2016/126858 A2 | 8/2016 |
| WO | WO 2017/147383 A1 | 8/2017 |

OTHER PUBLICATIONS

Grosso et. al. J. Clin. Invest. 117:3383-3392 (2007) (Year: 2007).*
Andrews et. al. Immunol Rev. 276(1):90-96 (2017) (Year: 2017).*
Reichert & Valge-Archer, Nat. Rev. Drug Disc. 2007; 6:349-356 (Year: 2007).*
Chan and Carter, Nature Reviews Immunology, 2010; 10:301-316 (Year: 2010).*
HogenEsch and Nikitin, J Control Release, 10:183-186 (2012) (Year: 2012).*
Zhang et. al., Expert Rev. Mol. Diagn. 14(1):97-106 (2014) (Year: 2014).*
European Search Report For EP19824733.0 dated Jul. 5, 2022 from European patent office in a counterpart European patent application.
International Search Report for PCT/KR2019/007877 dated Oct. 31, 2019.
Holliger et al., "Diabodies": Small bivalent and bispecific antibody fragments, Proc. Natl. Acad. Sci. U.S.A., vol. 90, pp. 6444-6448, 1993.
Muller et al., "A dimeric bispecific miniantibody combines two specificities with avidity", FEBS letters, vol. 432, pp. 45-49, 1998.
Merchant et al., "An efficient route to human bispecific IgG", Nat. Biotechnology, vol. 16, pp. 677-681, 1998.
Rossi et al., "Stably tethered multifunctional structures of defined composition made by the dock and lock method for use in cancer targeting", Proc. Natl. Acad. Sci. U.S.A., vol. 103(18), pp. 6841-6846, 2006.

* cited by examiner

*Primary Examiner* — Jessica H Roark
*Assistant Examiner* — Francesca Edgingtongiordan
(74) *Attorney, Agent, or Firm* — The PL Law Group, PLLC

(57) ABSTRACT

A monoclonal antibody or an antigen-binding fragment thereof according to an embodiment of the present invention can bind to lymphocyte-activation gene 3 (LAG-3) including a heavy chain variable region and a light chain variable region and inhibit the activity thereof. Thus it is expected to be useful for the development of immunotherapeutic agents for various disorders that are associated with LAG-3.

16 Claims, 16 Drawing Sheets
Specification includes a Sequence Listing.

FIG. 1
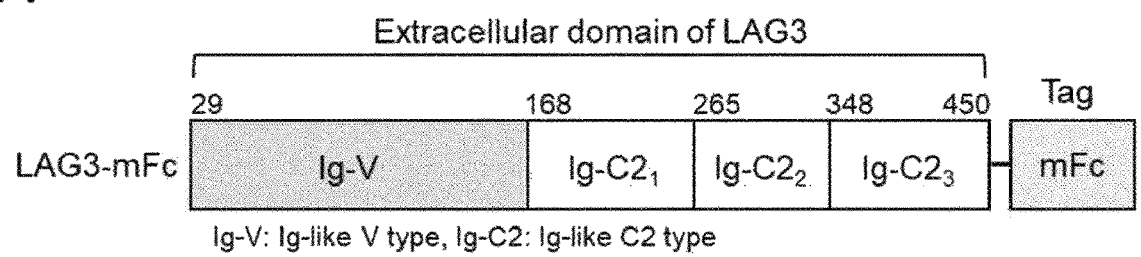
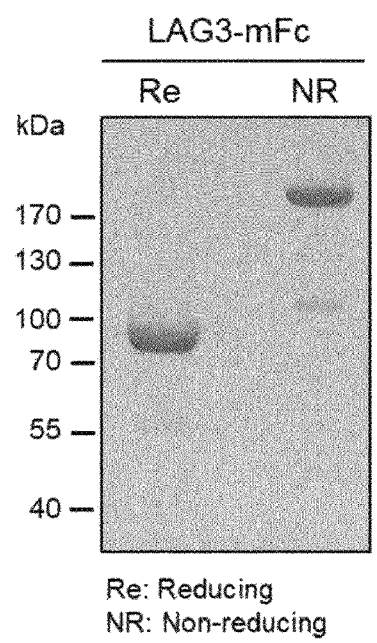
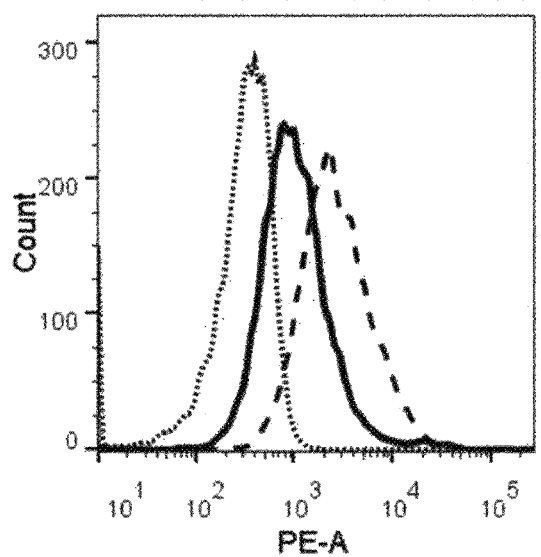

Binding Affinity of 1E09 antibody for hLAG3-mFc

Binding Affinity of 1E09 antibody for MrhLAG3-mFc

Binding Affinity of 1E09 antibody for mLAG3-mFc

```
WT   29 VPVVWAQEGAPAQLPCSPTIPLQDLSLLRRAGVTWQHQPDSGPPAAAPGHPLAPGPHPAAPSSWGPRPRRYTVLSVGPGGLR
        SGRLPLQPRVQLDERGRQRGDFSLMLRPARRADAGEYRAAVHLRDRALSCRLRLRLG 167 (SEQ ID NO: 79)
M1   29 VPVVWAQEGAPAQLPCSPTIPLQGYSLLRRAGVTWQHQPDSGPPAAAPGHPLAPGPHPAAPSSWGPRPRRYTVLSVGPGGLR
        SGRLPLQPRVQLDERGRQRGDFSLMLRPARRADAGEYRAAVHLRDRALSCRLRLRLG 167 (SEQ ID NO: 94)
M2   29 VPVVWAQEGAPAQLPCSPTIPLQDLSLLRRAGVTWQHQPDSGPPAAAPGHPLAPGPHPAAPGPRPPRHPAAPSSWGPRPRRYTVLSVGPGGLR
        SGRLPLQPRVQLDERGRQRGDFSLMLRPARRADAGEYRAAVHLRDRALSCRLRLRLG 167 (SEQ ID NO: 120)
M3   29 VPVVWAQEGAPAQLPCSPTIPLQDLSLLRRAGVTWQHQPDSGPPAAAPGHPLAPGPEPLSPHSHGPLPARYTVLSVGPGGLR
        SGRLPLQPRVQLDERGRQRGDFSLMLRPARRADAGEYRAAVHLRDRALSCRLRLRLG 167 (SEQ ID NO: 121)
M4   29 VPVVWAQEGAPAQLPCSPTIPLQDLSLLRRAGVTWQHQPDSGPPAAAPGHPLAPGPHPAAPSSWGPRPRRYTVLSVGPGGLR
        AGRWPLRPRVQLDERGRQRGDFSLMLRPARRADAGEYRAAVHLRDRALSCRLRLRLG 167 (SEQ ID NO: 122)
M5   29 VPVVWAQEGAPAQLPCSPTIPLQDLSLLRRAGVTWQHQPDSGPPAAAPGHPLAPGPHPAAPSSWGPRPRRYTVLSVGPGGLR
        SGRLPLQPRVQLDEAGRQRGDFSLMLRPARRADAGEYRAAVHLRDRALSCRLRLRLG 167 (SEQ ID NO: 123)
M6   29 VPVVWAQEGAPAQLPCSPTIPLQDLSLLRRAGVTWQHQPDSGPPAAAPGHPLAPGPHPAAPSSWGPRPRRYTVLSVGPGGLR
        SGRLPLQPRVQLDERGRQRGDFSLMLRPARRADAGEYRAAVHLRDRALSCRLRLRLG 167 (SEQ ID NO: 124)
M7   29 VPVVWAQEGAPAQLPCSPTIPLQDLSLLRRAGVTWQHQPDSGPPAAAPGHPLAPGPHPAAPSSWGPRPRRYTVLSVGPGGLR
        SGRLPLQPRVQLDERGRQRGDFSLMLRPARRADAGEYRAQVHYEDGELRCHLRLRLG 167 (SEQ ID NO: 125)
```

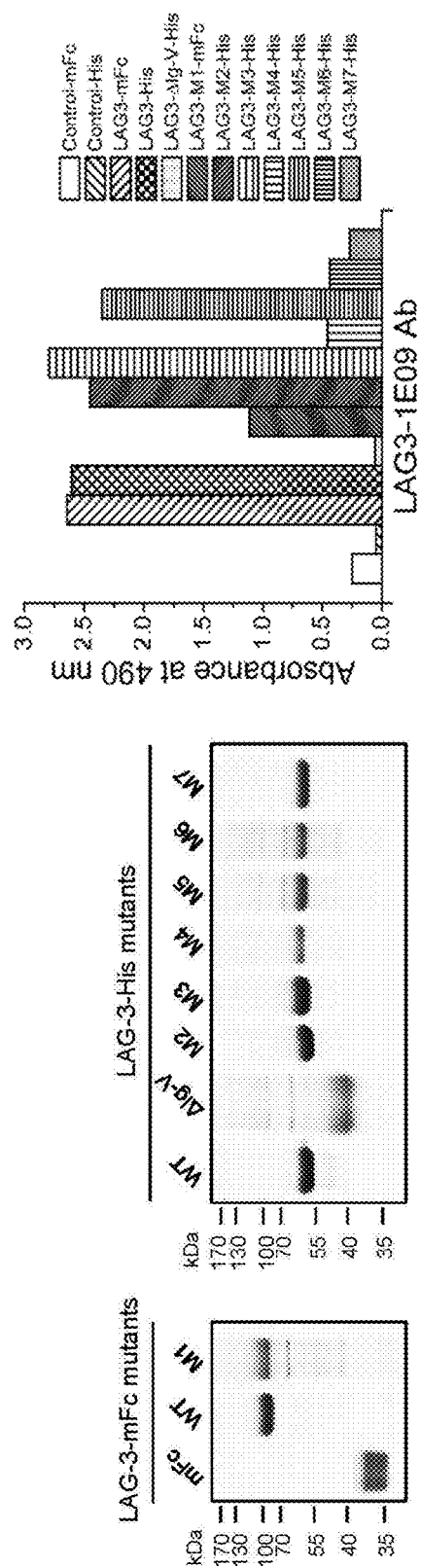

Cell-based competitive-binding assay (Raji cells)

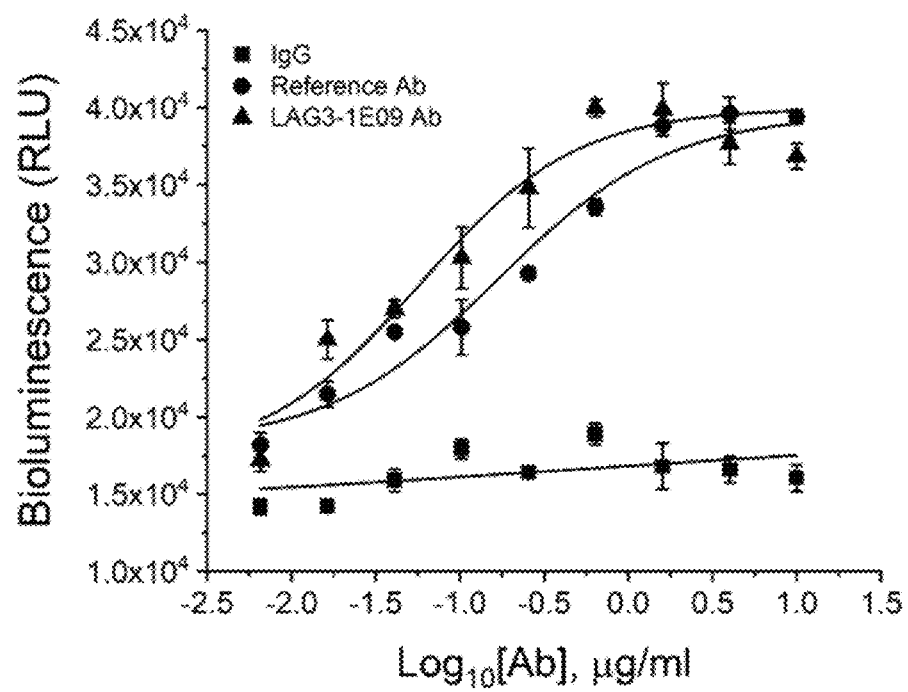

SEQUENCE LISTING

<160> NUMBER OF SEQ ID NOS: 125

<210> SEQ ID NO 1
<211> LENGTH: 8
<212> TYPE: PRT
<213> ORGANISM: Artificial Sequence
<220> FEATURE:
<223> OTHER INFORMATION: anti-LAG-3_1E09-VH-CDR1

<400> SEQUENCE: 1

Gly Phe Ser Phe Ser Asp His Tyr
1               5

<210> SEQ ID NO 2
<211> LENGTH: 8
<212> TYPE: PRT
<213> ORGANISM: Artificial Sequence
<220> FEATURE:
<223> OTHER INFORMATION: anti-LAG-3_1E09-VH-CDR2

<400> SEQUENCE: 2

Ile Asp Thr Ser Ala Thr Tyr Ile
1               5

<210> SEQ ID NO 3
<211> LENGTH: 10
<212> TYPE: PRT
<213> ORGANISM: Artificial Sequence
<220> FEATURE:
<223> OTHER INFORMATION: anti-LAG-3_1E09-VH-CDR3

<400> SEQUENCE: 3

Ala Arg Asp Asn Trp Gly Ser Leu Asp Tyr
1               5                   10

<210> SEQ ID NO 4
<211> LENGTH: 25
<212> TYPE: PRT
<213> ORGANISM: Artificial Sequence
<220> FEATURE:
<223> OTHER INFORMATION: anti-LAG-3_1E09-VH-FR1

<400> SEQUENCE: 4

Gln Val Gln Leu Val Gln Ser Gly Gly Asp Leu Val Lys Pro Gly Gly
1               5                   10                  15

Ser Leu Arg Leu Ser Cys Ala Ala Ser
            20                  25

<210> SEQ ID NO 5
<211> LENGTH: 17
<212> TYPE: PRT
<213> ORGANISM: Artificial Sequence
<220> FEATURE:
<223> OTHER INFORMATION: anti-LAG-3_1E09-VH-FR2

<400> SEQUENCE: 5

Met Asn Trp Ile Arg Gln Ala Pro Gly Lys Gly Leu Glu Trp Val Ala
1               5                   10                  15

Tyr

<210> SEQ ID NO 6
<211> LENGTH: 38
<212> TYPE: PRT
<213> ORGANISM: Artificial Sequence
<220> FEATURE:
<223> OTHER INFORMATION: anti-LAG-3_1E09-VH-FR3

-continued

<400> SEQUENCE: 6

Tyr Tyr Ala Asp Ser Val Lys Gly Arg Phe Thr Ile Ser Arg Asp Asn
1               5                   10                  15

Ala Lys Asn Ser Leu Tyr Leu Gln Met Asn Ser Leu Arg Ala Glu Asp
            20                  25                  30

Thr Ala Val Tyr Tyr Cys
        35

<210> SEQ ID NO 7
<211> LENGTH: 11
<212> TYPE: PRT
<213> ORGANISM: Artificial Sequence
<220> FEATURE:
<223> OTHER INFORMATION: anti-LAG-3_1E09-VH-FR4

<400> SEQUENCE: 7

Trp Gly Gln Gly Ala Leu Val Thr Val Ser Ser
1               5                   10

<210> SEQ ID NO 8
<211> LENGTH: 6
<212> TYPE: PRT
<213> ORGANISM: Artificial Sequence
<220> FEATURE:
<223> OTHER INFORMATION: anti-LAG-3_1E09-VL-CDR1

<400> SEQUENCE: 8

Gln Glu Ile Ser Ile Tyr
1               5

<210> SEQ ID NO 9
<211> LENGTH: 11
<212> TYPE: PRT
<213> ORGANISM: Homo sapiens

<400> SEQUENCE: 9

Gly Gly Leu Arg Ser Gly Arg Leu Pro Leu Gln
1               5                   10

<210> SEQ ID NO 10
<211> LENGTH: 9
<212> TYPE: PRT
<213> ORGANISM: Artificial Sequence
<220> FEATURE:
<223> OTHER INFORMATION: anti-LAG-3_1E09-VL-CDR3

<400> SEQUENCE: 10

Gln Gln Thr Tyr Ile Thr Pro Tyr Thr
1               5

<210> SEQ ID NO 11
<211> LENGTH: 26
<212> TYPE: PRT
<213> ORGANISM: Artificial Sequence
<220> FEATURE:
<223> OTHER INFORMATION: anti-LAG-3_1E09-VL-FR1

<400> SEQUENCE: 11

Asp Ile Gln Met Thr Gln Ser Pro Ser Ser Leu Ser Pro Ser Val Gly
1               5                   10                  15

Asp Arg Val Thr Ile Thr Cys Gln Ala Ser
            20                  25

-continued

```
<210> SEQ ID NO 12
<211> LENGTH: 17
<212> TYPE: PRT
<213> ORGANISM: Artificial Sequence
<220> FEATURE:
<223> OTHER INFORMATION: anti-LAG-3_1E09-VL-FR2

<400> SEQUENCE: 12

Leu Asn Trp Tyr Gln Gln Lys Pro Gly Lys Ala Pro Lys Leu Leu Ile
1               5                   10                  15

Tyr

<210> SEQ ID NO 13
<211> LENGTH: 36
<212> TYPE: PRT
<213> ORGANISM: Artificial Sequence
<220> FEATURE:
<223> OTHER INFORMATION: anti-LAG-3_1E09-VL-FR3

<400> SEQUENCE: 13

Asn Leu Glu Thr Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 14
<211> LENGTH: 10
<212> TYPE: PRT
<213> ORGANISM: Artificial Sequence
<220> FEATURE:
<223> OTHER INFORMATION: anti-LAG-3_1E09-VL-FR4

<400> SEQUENCE: 14

Phe Gly Gln Gly Thr Lys Leu Asp Ile Lys
1               5                   10

<210> SEQ ID NO 15
<211> LENGTH: 25
<212> TYPE: PRT
<213> ORGANISM: Artificial Sequence
<220> FEATURE:
<223> OTHER INFORMATION: anti-LAG-3_1E09_LS_1A10-VH-FR1

<400> SEQUENCE: 15

Glu Val Gln Leu Val Glu Ser Gly Gly Asp Leu Val Lys Pro Gly Gly
1               5                   10                  15

Ser Leu Arg Leu Ser Cys Ala Ala Ser
            20                  25

<210> SEQ ID NO 16
<211> LENGTH: 11
<212> TYPE: PRT
<213> ORGANISM: Artificial Sequence
<220> FEATURE:
<223> OTHER INFORMATION: anti-LAG-3_1E09_LS_1A10-VH-FR4

<400> SEQUENCE: 16

Trp Gly Gln Gly Thr Leu Val Thr Val Ser Ser
1               5                   10

<210> SEQ ID NO 17
<211> LENGTH: 25
<212> TYPE: PRT
```

<213> ORGANISM: Artificial Sequence
<220> FEATURE:
<223> OTHER INFORMATION: anti-LAG-3_1E09_LS_1G11-VH-FR1

<400> SEQUENCE: 17

Glu Val Gln Leu Val Glu Ser Gly Gly Asp Leu Val Gln Pro Gly Gly
1               5                   10                  15

Ser Leu Arg Leu Ser Cys Ala Ala Ser
            20                  25

<210> SEQ ID NO 18
<211> LENGTH: 8
<212> TYPE: PRT
<213> ORGANISM: Artificial Sequence
<220> FEATURE:
<223> OTHER INFORMATION: anti-LAG-3_1E09_LS_1G11-VH-CDR1

<400> SEQUENCE: 18

Gly Phe Asn Phe Ser Asp His Tyr
1               5

<210> SEQ ID NO 19
<211> LENGTH: 17
<212> TYPE: PRT
<213> ORGANISM: Artificial Sequence
<220> FEATURE:
<223> OTHER INFORMATION: anti-LAG-3_1E09_LS_1G11-VH-FR2

<400> SEQUENCE: 19

Met Asn Trp Val Arg Gln Ala Pro Gly Lys Gly Leu Glu Trp Val Ala
1               5                   10                  15

Tyr

<210> SEQ ID NO 20
<211> LENGTH: 8
<212> TYPE: PRT
<213> ORGANISM: Artificial Sequence
<220> FEATURE:
<223> OTHER INFORMATION: anti-LAG-3_1E09_LS_1G11-VH-CDR2

<400> SEQUENCE: 20

Ile Asp Thr Thr Ala Thr Tyr Ile
1               5

<210> SEQ ID NO 21
<211> LENGTH: 25
<212> TYPE: PRT
<213> ORGANISM: Artificial Sequence
<220> FEATURE:
<223> OTHER INFORMATION: anti-LAG-3_1E09_FR_1A06-VH-FR1

<400> SEQUENCE: 21

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 22
<211> LENGTH: 25
<212> TYPE: PRT
<213> ORGANISM: Artificial Sequence
<220> FEATURE:
<223> OTHER INFORMATION: anti-LAG-3_1E09_FR_1E05-VH-FR1

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 23
<211> LENGTH: 8
<212> TYPE: PRT
<213> ORGANISM: Artificial Sequence
<220> FEATURE:
<223> OTHER INFORMATION: anti-LAG-3_1E09_CDR_1E03-VH-CDR1

<400> SEQUENCE: 23

Gly Phe Thr Phe Asn Asp His Tyr
1               5

<210> SEQ ID NO 24
<211> LENGTH: 8
<212> TYPE: PRT
<213> ORGANISM: Artificial Sequence
<220> FEATURE:
<223> OTHER INFORMATION: anti-LAG-3_1E09_AM_1B03-VH-CDR1

<400> SEQUENCE: 24

Gly Phe Ser Phe Asn Asp His Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: anti-LAG-3_1E09_AM_2E09-VH-CDR2

<400> SEQUENCE: 25

Ile Asp Thr Asn Ala Thr Tyr Ile
1               5

<210> SEQ ID NO 26
<211> LENGTH: 8
<212> TYPE: PRT
<213> ORGANISM: Artificial Sequence
<220> FEATURE:
<223> OTHER INFORMATION: anti-LAG-3_1E09_AM_2G11-VH-CDR1

<400> SEQUENCE: 26

Gly Phe Ser Phe Thr Asp His Tyr
1               5

<210> SEQ ID NO 27
<211> LENGTH: 8
<212> TYPE: PRT
<213> ORGANISM: Artificial Sequence
<220> FEATURE:
<223> OTHER INFORMATION: anti-LAG-3_1E09_AM_2H01-VH-CDR1

<400> SEQUENCE: 27

Gly Phe Thr Phe Ser Asp His Tyr
1               5

<210> SEQ ID NO 28
<211> LENGTH: 8
<212> TYPE: PRT
<213> ORGANISM: Artificial Sequence
<220> FEATURE:
<223> OTHER INFORMATION: anti-LAG-3_1E09_AM_2H06-VH-CDR2
```

```
<400> SEQUENCE: 28

Ile Asp Thr Ile Ala Thr Tyr Ile
1               5

<210> SEQ ID NO 29
<211> LENGTH: 26
<212> TYPE: PRT
<213> ORGANISM: Artificial Sequence
<220> FEATURE:
<223> OTHER INFORMATION: anti-LAG-3_1E09_LS_1A10-VL-FR1

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser
            20                  25

<210> SEQ ID NO 30
<211> LENGTH: 6
<212> TYPE: PRT
<213> ORGANISM: Artificial Sequence
<220> FEATURE:
<223> OTHER INFORMATION: anti-LAG-3_1E09_LS_1A10-VL-CDR1

<400> SEQUENCE: 30

Gln Ser Ile Ser Ser Tyr
1               5

<210> SEQ ID NO 31
<211> LENGTH: 12
<212> TYPE: PRT
<213> ORGANISM: Homo sapiens

<400> SEQUENCE: 31

Ala Val His Leu Arg Asp Arg Ala Leu Ser Cys Arg
1               5                   10

<210> SEQ ID NO 32
<211> LENGTH: 36
<212> TYPE: PRT
<213> ORGANISM: Artificial Sequence
<220> FEATURE:
<223> OTHER INFORMATION: anti-LAG-3_1E09_LS_1A10-VL-FR3

<400> SEQUENCE: 32

Ser Leu Gln Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 33
<211> LENGTH: 9
<212> TYPE: PRT
<213> ORGANISM: Artificial Sequence
<220> FEATURE:
<223> OTHER INFORMATION: anti-LAG-3_1E09_LS_1A10-VL-CDR3

<400> SEQUENCE: 33

Gln Gln Ser Tyr Ser Thr Pro Tyr Thr
1               5

<210> SEQ ID NO 34
```

```
<211> LENGTH: 10
<212> TYPE: PRT
<213> ORGANISM: Artificial Sequence
<220> FEATURE:
<223> OTHER INFORMATION: anti-LAG-3_1E09_LS_1A10-VL-FR4

<400> SEQUENCE: 34

Phe Gly Gln Gly Thr Lys Leu Glu Ile Lys
1               5                   10

<210> SEQ ID NO 35
<211> LENGTH: 26
<212> TYPE: PRT
<213> ORGANISM: Artificial Sequence
<220> FEATURE:
<223> OTHER INFORMATION: anti-LAG-3_1E09_LS_1E06-VL-FR1

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Gln Ala Ser
            20                  25

<210> SEQ ID NO 36
<211> LENGTH: 6
<212> TYPE: PRT
<213> ORGANISM: Artificial Sequence
<220> FEATURE:
<223> OTHER INFORMATION: anti-LAG-3_1E09_LS_1E06-VL-CDR1

<400> SEQUENCE: 36

Gln Asp Ile Ser His Tyr
1               5

<210> SEQ ID NO 37
<211> LENGTH: 17
<212> TYPE: PRT
<213> ORGANISM: Artificial Sequence
<220> FEATURE:
<223> OTHER INFORMATION: anti-LAG-3_1E09_LS_1E06-VL-FR2

<400> SEQUENCE: 37

Leu Asn Trp Tyr Arg Gln Lys Pro Gly Lys Ala Pro Lys Leu Leu Ile
1               5                   10                  15

Tyr

<210> SEQ ID NO 38
<211> LENGTH: 36
<212> TYPE: PRT
<213> ORGANISM: Artificial Sequence
<220> FEATURE:
<223> OTHER INFORMATION: anti-LAG-3_1E09_LS_1E06-VL-FR3

<400> SEQUENCE: 38

Asn Leu Glu Thr Gly Val Pro Ser Arg Phe Ser Gly Ser Gly Ser Gly
1               5                   10                  15

Thr Leu Phe Thr Leu Thr Ile Ser Ser Leu Gln Pro Glu Asp Phe Ala
            20                  25                  30

Thr Tyr Tyr Cys
        35

<210> SEQ ID NO 39
<211> LENGTH: 6
<212> TYPE: PRT
<213> ORGANISM: Artificial Sequence
```

```
<220> FEATURE:
<223> OTHER INFORMATION: anti-LAG-3_1E09_LS_1G11-VL-CDR1

<400> SEQUENCE: 39

Gln Asp Ile Asp Lys Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: anti-LAG-3_1E09_LS_1G11-VL-CDR3

<400> SEQUENCE: 40

Gln Gln Ser Tyr Ser Thr Pro Asn Thr
1               5

<210> SEQ ID NO 41
<211> LENGTH: 26
<212> TYPE: PRT
<213> ORGANISM: Artificial Sequence
<220> FEATURE:
<223> OTHER INFORMATION: anti-LAG-3_1E09_LS_1H04-VL-FR1

<400> SEQUENCE: 41

Asp Ile Gln Met Thr Gln Ser Pro Ser Ser Leu Ser Ala Ser Ala Gly
1               5                   10                  15

Asp Arg Val Thr Ile Thr Cys Gln Ala Ser
            20                  25

<210> SEQ ID NO 42
<211> LENGTH: 6
<212> TYPE: PRT
<213> ORGANISM: Artificial Sequence
<220> FEATURE:
<223> OTHER INFORMATION: anti-LAG-3_1E09_LS_1H04-VL-CDR1

<400> SEQUENCE: 42

Gln Asp Ile Arg Asn Ser
1               5

<210> SEQ ID NO 43
<211> LENGTH: 17
<212> TYPE: PRT
<213> ORGANISM: Artificial Sequence
<220> FEATURE:
<223> OTHER INFORMATION: anti-LAG-3_1E09_LS_1H04-VL-FR2

<400> SEQUENCE: 43

Leu Ser Trp Tyr Gln Gln Lys Pro Gly Lys Ala Pro Lys Leu Leu Ile
1               5                   10                  15

Tyr

<210> SEQ ID NO 44
<211> LENGTH: 36
<212> TYPE: PRT
<213> ORGANISM: Artificial Sequence
<220> FEATURE:
<223> OTHER INFORMATION: anti-LAG-3_1E09_LS_1H04-VL-FR3

<400> SEQUENCE: 44

Asn Leu Glu Thr Gly Val Pro Ser Arg Phe Ser Gly Ser Gly Ser Gly
1               5                   10                  15

Thr Tyr Phe Thr Phe Thr Ile Ser Ser Leu Gln Pro Glu Asp Phe Ala
```

```
                20                  25                  30

Thr Tyr Tyr Cys
        35

<210> SEQ ID NO 45
<211> LENGTH: 9
<212> TYPE: PRT
<213> ORGANISM: Artificial Sequence
<220> FEATURE:
<223> OTHER INFORMATION: anti-LAG-3_1E09_LS_1H04-VL-CDR3

<400> SEQUENCE: 45

Gln Gln Tyr Asp Asn Val Pro Val Thr
1               5

<210> SEQ ID NO 46
<211> LENGTH: 10
<212> TYPE: PRT
<213> ORGANISM: Artificial Sequence
<220> FEATURE:
<223> OTHER INFORMATION: anti-LAG-3_1E09_LS_1H04-VL-FR4

<400> SEQUENCE: 46

Phe Gly Gly Gly Thr Lys Leu Glu Ile Lys
1               5                   10

<210> SEQ ID NO 47
<211> LENGTH: 26
<212> TYPE: PRT
<213> ORGANISM: Artificial Sequence
<220> FEATURE:
<223> OTHER INFORMATION: anti-LAG-3_1E09_FR_1A06-VL-FR1

<400> SEQUENCE: 47

Asp Ile Gln Met Thr Gln Ser Pro Gly Thr Leu Ser Met Ser Pro Gly
1               5                   10                  15

Glu Lys Ala Thr Leu Ser Cys Arg Ala Ser
            20                  25

<210> SEQ ID NO 48
<211> LENGTH: 6
<212> TYPE: PRT
<213> ORGANISM: Artificial Sequence
<220> FEATURE:
<223> OTHER INFORMATION: anti-LAG-3_1E09_FR_1A06-VL-CDR1

<400> SEQUENCE: 48

Gln Thr Val Thr Thr Asn
1               5

<210> SEQ ID NO 49
<211> LENGTH: 17
<212> TYPE: PRT
<213> ORGANISM: Artificial Sequence
<220> FEATURE:
<223> OTHER INFORMATION: anti-LAG-3_1E09_FR_1A06-VL-FR2

<400> SEQUENCE: 49

Leu Ala Trp Tyr Gln Gln Lys Ser Gly Gln Ala Pro Arg Leu Leu Ile
1               5                   10                  15

Tyr

<210> SEQ ID NO 50
<211> LENGTH: 36
<212> TYPE: PRT
```

<213> ORGANISM: Artificial Sequence
<220> FEATURE:
<223> OTHER INFORMATION: anti-LAG-3_1E09_FR_1A06-VL-FR3

<400> SEQUENCE: 50

Thr Arg Ala Thr Gly Val Pro Asp Arg Phe Ser Gly Ser Gly Ser Gly
1               5                   10                  15
Thr Asp Phe Thr Leu Thr Ile Ser Arg Leu Glu Pro Glu Asp Phe Ala
            20                  25                  30
Val Tyr Tyr Cys
        35

<210> SEQ ID NO 51
<211> LENGTH: 9
<212> TYPE: PRT
<213> ORGANISM: Artificial Sequence
<220> FEATURE:
<223> OTHER INFORMATION: anti-LAG-3_1E09_FR_1A06-VL-CDR3

<400> SEQUENCE: 51

Gln Gln Tyr Gly Ser Ser Pro Tyr Thr
1               5

<210> SEQ ID NO 52
<211> LENGTH: 26
<212> TYPE: PRT
<213> ORGANISM: Artificial Sequence
<220> FEATURE:
<223> OTHER INFORMATION: anti-LAG-3_1E09_FR_1A10-VL-FR1

<400> SEQUENCE: 52

Asp Ile Gln Met Thr Gln Ser Pro Ser Ser Leu Ser Ala Ser Val Gly
1               5                   10                  15
Asp Arg Val Thr Ile Thr Cys Gln Ala Asn
            20                  25

<210> SEQ ID NO 53
<211> LENGTH: 6
<212> TYPE: PRT
<213> ORGANISM: Artificial Sequence
<220> FEATURE:
<223> OTHER INFORMATION: anti-LAG-3_1E09_FR_1A10-VL-CDR1

<400> SEQUENCE: 53

Gln Asp Ile Ser Asn Tyr
1               5

<210> SEQ ID NO 54
<211> LENGTH: 36
<212> TYPE: PRT
<213> ORGANISM: Artificial Sequence
<220> FEATURE:
<223> OTHER INFORMATION: anti-LAG-3_1E09_FR_1A10-VL-FR3

<400> SEQUENCE: 54

Asn Leu Glu Thr Gly Val Pro Ser Arg Phe Ser Gly Gly Gly Ser Gly
1               5                   10                  15
Thr Asp Phe Thr Leu Thr Ile Asn Asn Leu Gln Pro Glu Asp Phe Ala
            20                  25                  30
Thr Tyr Tyr Cys
        35

<210> SEQ ID NO 55
<211> LENGTH: 9

```
<212> TYPE: PRT
<213> ORGANISM: Artificial Sequence
<220> FEATURE:
<223> OTHER INFORMATION: anti-LAG-3_1E09_FR_1A10-VL-CDR3

<400> SEQUENCE: 55

His His Ser Tyr Asn Thr Pro Ile Thr
1               5

<210> SEQ ID NO 56
<211> LENGTH: 10
<212> TYPE: PRT
<213> ORGANISM: Artificial Sequence
<220> FEATURE:
<223> OTHER INFORMATION: anti-LAG-3_1E09_FR_1A10-VL-FR4

<400> SEQUENCE: 56

Phe Gly Gln Gly Thr Arg Leu Glu Ile Lys
1               5                   10

<210> SEQ ID NO 57
<211> LENGTH: 6
<212> TYPE: PRT
<213> ORGANISM: Artificial Sequence
<220> FEATURE:
<223> OTHER INFORMATION: anti-LAG-3_1E09_FR_1E05-VL-CDR1

<400> SEQUENCE: 57

Gln Ser Ile Ser Ser Trp
1               5

<210> SEQ ID NO 58
<211> LENGTH: 17
<212> TYPE: PRT
<213> ORGANISM: Artificial Sequence
<220> FEATURE:
<223> OTHER INFORMATION: anti-LAG-3_1E09_FR_1E05-VL-FR2

<400> SEQUENCE: 58

Leu Ala Trp Tyr Gln His Lys Pro Gly Lys Ala Pro Lys Leu Leu Ile
1               5                   10                  15

Tyr

<210> SEQ ID NO 59
<211> LENGTH: 36
<212> TYPE: PRT
<213> ORGANISM: Artificial Sequence
<220> FEATURE:
<223> OTHER INFORMATION: anti-LAG-3_1E09_FR_1E05-VL-FR3

<400> SEQUENCE: 59

Asn Leu Glu Thr Gly Ala Pro Ser Arg Phe Ser Gly Ser Gly Ser Gly
1               5                   10                  15

Thr Asp Phe Thr Phe Thr Ile Tyr Ser Leu Gln Pro Glu Asp Val Ala
                20                  25                  30

Thr Tyr Tyr Cys
        35

<210> SEQ ID NO 60
<211> LENGTH: 9
<212> TYPE: PRT
<213> ORGANISM: Artificial Sequence
<220> FEATURE:
<223> OTHER INFORMATION: anti-LAG-3_1E09_FR_1E05-VL-CDR3

<400> SEQUENCE: 60
```

```
Gln Gln Tyr Asp Thr Val Pro Pro Thr
1               5

<210> SEQ ID NO 61
<211> LENGTH: 10
<212> TYPE: PRT
<213> ORGANISM: Artificial Sequence
<220> FEATURE:
<223> OTHER INFORMATION: anti-LAG-3_1E09_FR_1E05-VL-FR4

<400> SEQUENCE: 61

Phe Gly Pro Gly Thr Lys Val Asp Ile Lys
1               5                   10

<210> SEQ ID NO 62
<211> LENGTH: 17
<212> TYPE: PRT
<213> ORGANISM: Artificial Sequence
<220> FEATURE:
<223> OTHER INFORMATION: anti-LAG-3_1E09_FR_1E09-VL-FR2

<400> SEQUENCE: 62

Leu Asn Trp Tyr Gln Gln Lys Pro Gly Lys Ala Pro Asn Leu Leu Ile
1               5                   10                  15

Tyr

<210> SEQ ID NO 63
<211> LENGTH: 36
<212> TYPE: PRT
<213> ORGANISM: Artificial Sequence
<220> FEATURE:
<223> OTHER INFORMATION: anti-LAG-3_1E09_FR_1E09-VL-FR3

<400> SEQUENCE: 63

Asn Leu Glu Thr Gly Val Pro Ser Arg Phe Ser Gly Ser Gly Ser Gly
1               5                   10                  15

Thr Asp Phe Ala Leu Thr Ile Ser Ser Leu Gln Pro Glu Asp Phe Ala
            20                  25                  30

Thr Tyr Tyr Cys
        35

<210> SEQ ID NO 64
<211> LENGTH: 9
<212> TYPE: PRT
<213> ORGANISM: Artificial Sequence
<220> FEATURE:
<223> OTHER INFORMATION: anti-LAG-3_1E09_FR_1E09-VL-CDR3

<400> SEQUENCE: 64

Gln Gln Ser Asp Ser Thr Pro Ile Thr
1               5

<210> SEQ ID NO 65
<211> LENGTH: 10
<212> TYPE: PRT
<213> ORGANISM: Artificial Sequence
<220> FEATURE:
<223> OTHER INFORMATION: anti-LAG-3_1E09_FR_1E09-VL-FR4

<400> SEQUENCE: 65

Phe Gly Gln Gly Thr Arg Leu Asp Ile Lys
1               5                   10

<210> SEQ ID NO 66
```

<211> LENGTH: 26
<212> TYPE: PRT
<213> ORGANISM: Artificial Sequence
<220> FEATURE:
<223> OTHER INFORMATION: anti-LAG-3_1E09_FR_1E10-VL-FR1

<400> SEQUENCE: 66

```
Asp Ile Gln Met Thr Gln Ser Pro Ser Ser Leu Ser Ala Ser Val Gly
1               5                   10                  15
Asp Arg Val Ile Ile Thr Cys Gln Ala Ser
            20                  25
```

<210> SEQ ID NO 67
<211> LENGTH: 6
<212> TYPE: PRT
<213> ORGANISM: Artificial Sequence
<220> FEATURE:
<223> OTHER INFORMATION: anti-LAG-3_1E09_FR_1E10-VL-CDR1

<400> SEQUENCE: 67

```
Gln Asp Ile Thr Asn Tyr
1               5
```

<210> SEQ ID NO 68
<211> LENGTH: 36
<212> TYPE: PRT
<213> ORGANISM: Artificial Sequence
<220> FEATURE:
<223> OTHER INFORMATION: anti-LAG-3_1E09_FR_1E10-VL-FR3

<400> SEQUENCE: 68

```
Asn Leu Glu Thr Gly Val Pro Ser Arg Phe Thr Gly Ser Gly Ser Gly
1               5                   10                  15
Thr Asp Phe Thr Phe Thr Ile Ser Ser Leu Gln Pro Glu Asp Ile Ala
            20                  25                  30
Thr Tyr His Cys
        35
```

<210> SEQ ID NO 69
<211> LENGTH: 10
<212> TYPE: PRT
<213> ORGANISM: Artificial Sequence
<220> FEATURE:
<223> OTHER INFORMATION: anti-LAG-3_1E09_FR_1E10-VL-CDR3

<400> SEQUENCE: 69

```
Gln Gln Ser Tyr Ser Thr Pro Pro Tyr Thr
1               5                   10
```

<210> SEQ ID NO 70
<211> LENGTH: 36
<212> TYPE: PRT
<213> ORGANISM: Artificial Sequence
<220> FEATURE:
<223> OTHER INFORMATION: anti-LAG-3_1E09_FR_1F03-VL-FR3

<400> SEQUENCE: 70

```
Asn Leu Glu Thr Gly Val Pro Ser Arg Phe Ser Gly Ser Gly Ser Gly
1               5                   10                  15
Thr Asp Phe Thr Phe Thr Ile Ser Ser Leu Gln Pro Glu Asp Phe Ala
            20                  25                  30
Thr Tyr Tyr Cys
        35
```

<210> SEQ ID NO 71
<211> LENGTH: 9
<212> TYPE: PRT
<213> ORGANISM: Artificial Sequence
<220> FEATURE:
<223> OTHER INFORMATION: anti-LAG-3_1E09_FR_1F03-VL-CDR3

<400> SEQUENCE: 71

Gln Gln Ser Tyr Ser Thr Pro Phe Ala
1               5

<210> SEQ ID NO 72
<211> LENGTH: 10
<212> TYPE: PRT
<213> ORGANISM: Artificial Sequence
<220> FEATURE:
<223> OTHER INFORMATION: anti-LAG-3_1E09_FR_1F03-VL-FR4

<400> SEQUENCE: 72

Phe Gly Pro Gly Thr Lys Val Glu Ile Lys
1               5                   10

<210> SEQ ID NO 73
<211> LENGTH: 6
<212> TYPE: PRT
<213> ORGANISM: Artificial Sequence
<220> FEATURE:
<223> OTHER INFORMATION: anti-LAG-3_1E09_FR_1G07-VL-CDR1

<400> SEQUENCE: 73

Gln Gly Ile Ser Thr Tyr
1               5

<210> SEQ ID NO 74
<211> LENGTH: 36
<212> TYPE: PRT
<213> ORGANISM: Artificial Sequence
<220> FEATURE:
<223> OTHER INFORMATION: anti-LAG-3_1E09_FR_1G07-VL-FR3

<400> SEQUENCE: 74

Asn Leu Glu Thr Gly Val Pro Ser Arg Phe Ser Gly Ser Gly Ser Gly
1               5                   10                  15

Thr Asp Phe Thr Leu Thr Ile Ser Gly Leu Gln Pro Asp Asp Phe Ala
            20                  25                  30

Leu Tyr Tyr Cys
        35

<210> SEQ ID NO 75
<211> LENGTH: 9
<212> TYPE: PRT
<213> ORGANISM: Artificial Sequence
<220> FEATURE:
<223> OTHER INFORMATION: anti-LAG-3_1E09_FR_1G07-VL-CDR3

<400> SEQUENCE: 75

Gln Gln Ser Tyr Thr Thr Pro Tyr Ser
1               5

<210> SEQ ID NO 76
<211> LENGTH: 9
<212> TYPE: PRT
<213> ORGANISM: Artificial Sequence
<220> FEATURE:
<223> OTHER INFORMATION: anti-LAG-3_1E09_CDR_1D04-VL-CDR3

<400> SEQUENCE: 76

Gln Gln Ser Tyr Ile Thr Pro Tyr Thr
1               5

<210> SEQ ID NO 77
<211> LENGTH: 26
<212> TYPE: PRT
<213> ORGANISM: Artificial Sequence
<220> FEATURE:
<223> OTHER INFORMATION: anti-LAG-3_1E09_CDR_1E03-VL-FR1

<400> SEQUENCE: 77

Asp Ile Gln Met Thr Gln Ser Leu Ser Ser Leu Ser Ala Ser Val Gly
1               5                   10                  15

Asp Ser Val Thr Ile Thr Cys Gln Ala Ser
            20                  25

<210> SEQ ID NO 78
<211> LENGTH: 17
<212> TYPE: PRT
<213> ORGANISM: Artificial Sequence
<220> FEATURE:
<223> OTHER INFORMATION: anti-LAG-3_1E09_CDR_1E03-VL-FR2

<400> SEQUENCE: 78

Leu Asn Trp Tyr Arg Gln Lys Pro Gly Lys Ala Pro Glu Leu Leu Ile
1               5                   10                  15

Tyr

<210> SEQ ID NO 79
<211> LENGTH: 139
<212> TYPE: PRT
<213> ORGANISM: Homo sapiens

<400> SEQUENCE: 79

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

<210> SEQ ID NO 80
<211> LENGTH: 9
<212> TYPE: PRT
<213> ORGANISM: Artificial Sequence
<220> FEATURE:
<223> OTHER INFORMATION: anti-LAG-3_1E09_CDR_1E03-VL-CDR3

<400> SEQUENCE: 80

Gln Gln Ser Tyr Ser Ile Pro Tyr Thr
1               5

<210> SEQ ID NO 81
<211> LENGTH: 10
<212> TYPE: PRT
<213> ORGANISM: Artificial Sequence
<220> FEATURE:
<223> OTHER INFORMATION: anti-LAG-3_1E09_CDR_1E03-VL-FR4

<400> SEQUENCE: 81

Phe Gly Gln Gly Thr Lys Val Glu Ile Lys
1               5                   10

<210> SEQ ID NO 82
<211> LENGTH: 26
<212> TYPE: PRT
<213> ORGANISM: Artificial Sequence
<220> FEATURE:
<223> OTHER INFORMATION: anti-LAG-3_1E09_AM_1B03-VL-FR1

<400> SEQUENCE: 82

Asp Ile Gln Met Thr Gln Ser Pro Ser Ser Leu Ser Ala Ser Val Gly
1               5                   10                  15

Asp Arg Val Thr Met Thr Cys Gln Ala Ser
            20                  25

<210> SEQ ID NO 83
<211> LENGTH: 6
<212> TYPE: PRT
<213> ORGANISM: Artificial Sequence
<220> FEATURE:
<223> OTHER INFORMATION: anti-LAG-3_1E09_AM_1B03-VL-CDR1

<400> SEQUENCE: 83

Gln Asp Val Ser Asn Tyr
1               5

<210> SEQ ID NO 84
<211> LENGTH: 36
<212> TYPE: PRT
<213> ORGANISM: Artificial Sequence
<220> FEATURE:
<223> OTHER INFORMATION: anti-LAG-3_1E09_AM_1B03-VL-FR3

<400> SEQUENCE: 84

Asn Leu Glu Ile Gly Val Pro Ser Arg Phe Ser Gly Ser Gly Ser Gly
1               5                   10                  15

Thr Asp Phe Thr Phe Thr Ile Ser Ser Leu Gln Pro Glu Asp Thr Ala
            20                  25                  30

Thr Tyr Tyr Cys
        35

<210> SEQ ID NO 85
<211> LENGTH: 10
<212> TYPE: PRT
<213> ORGANISM: Artificial Sequence
<220> FEATURE:
<223> OTHER INFORMATION: anti-LAG-3_1E09_AM_1B03-VL-CDR3

<400> SEQUENCE: 85

Gln Gln Tyr Asp His Leu Pro Pro Tyr Thr
1               5                   10

<210> SEQ ID NO 86
<211> LENGTH: 26
<212> TYPE: PRT
<213> ORGANISM: Artificial Sequence
<220> FEATURE:
<223> OTHER INFORMATION: anti-LAG-3_1E09_AM_1E09-VL-FR1

<400> SEQUENCE: 86

Asp Ile Gln Met Thr Gln Ser Pro Ala Thr Leu Ser Val Ser Pro Gly
1               5                   10                  15

Glu Arg Ala Thr Leu Ser Cys Arg Ala Ser
            20                  25

<210> SEQ ID NO 87
<211> LENGTH: 6
<212> TYPE: PRT
<213> ORGANISM: Artificial Sequence
<220> FEATURE:
<223> OTHER INFORMATION: anti-LAG-3_1E09_AM_1E09-VL-CDR1

<400> SEQUENCE: 87

Gln Ser Val Met Asn Asn
1               5

<210> SEQ ID NO 88
<211> LENGTH: 17
<212> TYPE: PRT
<213> ORGANISM: Artificial Sequence
<220> FEATURE:
<223> OTHER INFORMATION: anti-LAG-3_1E09_AM_1E09-VL-FR2

<400> SEQUENCE: 88

Leu Ala Trp Tyr Gln Gln Lys Pro Gly Gln Ala Pro Arg Leu Leu Ile
1               5                   10                  15

Tyr

<210> SEQ ID NO 89
<211> LENGTH: 36
<212> TYPE: PRT
<213> ORGANISM: Artificial Sequence
<220> FEATURE:
<223> OTHER INFORMATION: anti-LAG-3_1E09_AM_1E09-VL-FR3

<400> SEQUENCE: 89

Asn Arg Ala Thr Gly Ile Pro Ala Arg Phe Ser Gly Ser Gly Ser Gly
1               5                   10                  15

Thr Asp Phe Thr Leu Thr Ile Ser Arg Leu Glu Pro Glu Asp Phe Ala
            20                  25                  30

Val Tyr Tyr Cys
        35

<210> SEQ ID NO 90
<211> LENGTH: 9
<212> TYPE: PRT
<213> ORGANISM: Artificial Sequence
<220> FEATURE:
<223> OTHER INFORMATION: anti-LAG-3_1E09_AM_1E09-VL-CDR3

<400> SEQUENCE: 90

Glu Gln Tyr Val Arg Ser Pro Tyr Thr
1               5

<210> SEQ ID NO 91
<211> LENGTH: 6
<212> TYPE: PRT

<213> ORGANISM: Artificial Sequence
<220> FEATURE:
<223> OTHER INFORMATION: anti-LAG-3_1E09_AM_1F09-VL-CDR1

<400> SEQUENCE: 91

Gln Asp Ile Arg Asn Tyr
1               5

<210> SEQ ID NO 92
<211> LENGTH: 17
<212> TYPE: PRT
<213> ORGANISM: Artificial Sequence
<220> FEATURE:
<223> OTHER INFORMATION: anti-LAG-3_1E09_AM_1F09-VL-FR2

<400> SEQUENCE: 92

Leu Gly Trp Tyr Gln Gln Lys Pro Gly Lys Ala Pro Asn Leu Leu Ile
1               5                   10                  15

Tyr

<210> SEQ ID NO 93
<211> LENGTH: 36
<212> TYPE: PRT
<213> ORGANISM: Artificial Sequence
<220> FEATURE:
<223> OTHER INFORMATION: anti-LAG-3_1E09_AM_1F09-VL-FR3

<400> SEQUENCE: 93

Thr Leu Glu Thr Gly Val Pro Ser Arg Phe Ser Gly Ser Gly Ser Gly
1               5                   10                  15

Thr Asp Phe Thr Leu Ala Ile Ser Ser Leu Gln Pro Glu Asp Phe Ala
            20                  25                  30

Thr Tyr Tyr Cys
        35

<210> SEQ ID NO 94
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 94

Val Pro Val Val Trp Ala Gln Glu Gly Ala Pro Ala Gln Leu Pro Cys
1               5                   10                  15

Ser Pro Thr Ile Pro Leu Gln Gly Tyr Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

<210> SEQ ID NO 95
<211> LENGTH: 36
<212> TYPE: PRT
<213> ORGANISM: Artificial Sequence
<220> FEATURE:
<223> OTHER INFORMATION: anti-LAG-3_1E09_AM_1H07-VL-FR3

<400> SEQUENCE: 95

Ser Leu Glu Ser Gly Val Pro Ser Arg Phe Ser Gly Ser Gly Ser Gly
1               5                   10                  15

Thr Glu Phe Thr Leu Thr Ile Asn Ser Leu Gln Pro Glu Asp Phe Ala
            20                  25                  30

Thr Tyr Tyr Cys
        35

<210> SEQ ID NO 96
<211> LENGTH: 26
<212> TYPE: PRT
<213> ORGANISM: Artificial Sequence
<220> FEATURE:
<223> OTHER INFORMATION: anti-LAG-3_1E09_AM_2E04-VL-FR1

<400> SEQUENCE: 96

Asp Ile Gln Met Thr Gln Ser Pro Ser Ser Leu Ser Ala Ser Val Gly
1               5                   10                  15

Asp Arg Val Thr Ile Ile Cys Arg Ala Ser
            20                  25

<210> SEQ ID NO 97
<211> LENGTH: 6
<212> TYPE: PRT
<213> ORGANISM: Artificial Sequence
<220> FEATURE:
<223> OTHER INFORMATION: anti-LAG-3_1E09_AM_2E04-VL-CDR1

<400> SEQUENCE: 97

Gln Ser Ile Ser Asn Tyr
1               5

<210> SEQ ID NO 98
<211> LENGTH: 17
<212> TYPE: PRT
<213> ORGANISM: Artificial Sequence
<220> FEATURE:
<223> OTHER INFORMATION: anti-LAG-3_1E09_AM_2E04-VL-FR2

<400> SEQUENCE: 98

Leu Asn Trp Tyr Gln Gln Glu Pro Gly Lys Ala Pro Lys Leu Leu Ile
1               5                   10                  15

Tyr

<210> SEQ ID NO 99
<211> LENGTH: 36
<212> TYPE: PRT
<213> ORGANISM: Artificial Sequence
<220> FEATURE:
<223> OTHER INFORMATION: anti-LAG-3_1E09_AM_2E04-VL-FR3

<400> SEQUENCE: 99

Asn Leu Glu Ser Gly Val Pro Ser Arg Phe Ser Gly Ser Gly Ser Gly
1               5                   10                  15

Thr Asp Phe Thr Leu Thr Ile Ser Ser Leu Gln Pro Glu Asp Phe Ala
            20                  25                  30

Thr Tyr Tyr Cys
        35

<210> SEQ ID NO 100
<211> LENGTH: 26
<212> TYPE: PRT
<213> ORGANISM: Artificial Sequence
<220> FEATURE:
<223> OTHER INFORMATION: anti-LAG-3_1E09_AM_2E09-VL-FR1

<400> SEQUENCE: 100

Asp Ile Gln Met Thr Gln Ser Ser Ser Leu Ser Ala Ser Val Gly
1               5                   10                  15

Asp Arg Val Thr Ile Thr Cys Gln Ala Ser
            20                  25

<210> SEQ ID NO 101
<211> LENGTH: 6
<212> TYPE: PRT
<213> ORGANISM: Artificial Sequence
<220> FEATURE:
<223> OTHER INFORMATION: anti-LAG-3_1E09_AM_2E09-VL-CDR1

<400> SEQUENCE: 101

Gln Asp Ile Thr Asp Phe
1               5

<210> SEQ ID NO 102
<211> LENGTH: 36
<212> TYPE: PRT
<213> ORGANISM: Artificial Sequence
<220> FEATURE:
<223> OTHER INFORMATION: anti-LAG-3_1E09_AM_2E09-VL-FR3

<400> SEQUENCE: 102

Asn Leu Glu Thr Gly Ile Pro Ser Arg Phe Ser Gly Ser Gly Ser Gly
1               5                   10                  15

Arg Glu Phe Thr Leu Thr Ile Asn Ser Leu Gln Pro Glu Asp Val Ala
            20                  25                  30

Ser Tyr Tyr Cys
        35

<210> SEQ ID NO 103
<211> LENGTH: 9
<212> TYPE: PRT
<213> ORGANISM: Artificial Sequence
<220> FEATURE:
<223> OTHER INFORMATION: anti-LAG-3_1E09_AM_2E09-VL-CDR3

<400> SEQUENCE: 103

Gln Gln Ser Tyr Thr Thr Pro Leu Thr
1               5

<210> SEQ ID NO 104
<211> LENGTH: 10
<212> TYPE: PRT
<213> ORGANISM: Artificial Sequence
<220> FEATURE:
<223> OTHER INFORMATION: anti-LAG-3_1E09_AM_2E09-VL-FR4

<400> SEQUENCE: 104

Phe Gly Gly Gly Thr Lys Val Asp Ile Lys
1               5                   10

```
<210> SEQ ID NO 105
<211> LENGTH: 6
<212> TYPE: PRT
<213> ORGANISM: Artificial Sequence
<220> FEATURE:
<223> OTHER INFORMATION: anti-LAG-3_1E09_AM_2G11-VL-CDR1

<400> SEQUENCE: 105

Gln Ser Ile Ser Tyr Tyr
1               5

<210> SEQ ID NO 106
<211> LENGTH: 17
<212> TYPE: PRT
<213> ORGANISM: Artificial Sequence
<220> FEATURE:
<223> OTHER INFORMATION: anti-LAG-3_1E09_AM_2G11-VL-FR2

<400> SEQUENCE: 106

Leu Asn Trp Tyr Gln Gln Arg Pro Gly Lys Ala Pro Lys Leu Leu Ile
1               5                   10                  15

Tyr

<210> SEQ ID NO 107
<211> LENGTH: 36
<212> TYPE: PRT
<213> ORGANISM: Artificial Sequence
<220> FEATURE:
<223> OTHER INFORMATION: anti-LAG-3_1E09_AM_2G11-VL-FR3

<400> SEQUENCE: 107

Asn Leu Glu Thr Gly Val Pro Ser Arg Phe Ser Gly Ser Gly Thr Gly
1               5                   10                  15

Thr Glu Phe Thr Leu Thr Ile Ser Ser Leu Gln Pro Glu Asp Phe Ala
            20                  25                  30

Thr Tyr Tyr Cys
        35

<210> SEQ ID NO 108
<211> LENGTH: 36
<212> TYPE: PRT
<213> ORGANISM: Artificial Sequence
<220> FEATURE:
<223> OTHER INFORMATION: anti-LAG-3_1E09_AM_2H01-VL-FR3

<400> SEQUENCE: 108

Thr Leu Glu Thr Gly Val Pro Ser Arg Phe Ser Gly Ser Gly Tyr Gly
1               5                   10                  15

Thr Asp Phe Thr Leu Thr Ile Ser Gly Leu Gln Pro Asp Asp Phe Ala
            20                  25                  30

Leu Tyr Tyr Cys
        35

<210> SEQ ID NO 109
<211> LENGTH: 17
<212> TYPE: PRT
<213> ORGANISM: Artificial Sequence
<220> FEATURE:
<223> OTHER INFORMATION: anti-LAG-3_1E09_AM_2H06-VL-FR2

<400> SEQUENCE: 109

Leu Asn Trp Tyr Gln Gln Thr Pro Gly Lys Ala Pro Lys Leu Leu Ile
1               5                   10                  15

Tyr
```

<210> SEQ ID NO 110
<211> LENGTH: 9
<212> TYPE: PRT
<213> ORGANISM: Artificial Sequence
<220> FEATURE:
<223> OTHER INFORMATION: anti-LAG-3_1E09_AM_2H06-VL-CDR3

<400> SEQUENCE: 110

Gln Gln Gly Tyr Gly Thr Pro Tyr Thr
1               5

<210> SEQ ID NO 111
<211> LENGTH: 10
<212> TYPE: PRT
<213> ORGANISM: Artificial Sequence
<220> FEATURE:
<223> OTHER INFORMATION: anti-LAG-3_1E09_AM_2H06-VL-FR4

<400> SEQUENCE: 111

Tyr Gly Gln Gly Thr Lys Leu Glu Ile Lys
1               5                   10

<210> SEQ ID NO 112
<211> LENGTH: 24
<212> TYPE: DNA
<213> ORGANISM: Artificial Sequence
<220> FEATURE:
<223> OTHER INFORMATION: primer

<400> SEQUENCE: 112
gtcccggtgg tgtgggccca ggag                                              24

<210> SEQ ID NO 113
<211> LENGTH: 24
<212> TYPE: DNA
<213> ORGANISM: Artificial Sequence
<220> FEATURE:
<223> OTHER INFORMATION: primer

<400> SEQUENCE: 113
gaggtggcct gctgggaggg cacc                                              24

<210> SEQ ID NO 114
<211> LENGTH: 117
<212> TYPE: PRT
<213> ORGANISM: Artificial Sequence
<220> FEATURE:
<223> OTHER INFORMATION: anti-LAG-3_1E09-VH

<400> SEQUENCE: 114

Gln Val Gln Leu Val Gln Ser Gly Gly Asp Leu Val Lys Pro Gly Gly
1               5                   10                  15

Ser Leu Arg Leu Ser Cys Ala Ala Ser Gly Phe Ser Phe Ser Asp His
            20                  25                  30

Tyr Met Asn Trp Ile Arg Gln Ala Pro Gly Lys Gly Leu Glu Trp Val
        35                  40                  45

Ala Tyr Ile Asp Thr Ser Ala Thr Tyr Ile Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Gly Ser Leu Asp Tyr Trp Gly Gln Gly Ala Leu
            100                 105                 110

Val Thr Val Ser Ser
        115

<210> SEQ ID NO 115
<211> LENGTH: 107
<212> TYPE: PRT
<213> ORGANISM: Artificial Sequence
<220> FEATURE:
<223> OTHER INFORMATION: anti-LAG-3_1E09-VL

<400> SEQUENCE: 115

Asp Ile Gln Met Thr Gln Ser Pro Ser Ser Leu Ser Pro Ser Val Gly
1               5                   10                  15

Asp Arg Val Thr Ile Thr Cys Gln Ala Ser Gln Glu Ile Ser Ile Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Ile Thr Pro Tyr
                85                  90                  95

Thr Phe Gly Gln Gly Thr Lys Leu Asp Ile Lys
            100                 105

<210> SEQ ID NO 116
<211> LENGTH: 117
<212> TYPE: PRT
<213> ORGANISM: Artificial Sequence
<220> FEATURE:
<223> OTHER INFORMATION: anti-LAG-3_1E09_AM_2H01-VH

<400> SEQUENCE: 116

Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asn Trp Val Arg Gln Ala Pro Gly Lys Gly Leu Glu Trp Val
        35                  40                  45

Ala Tyr Ile Asp Thr Ser Ala Thr Tyr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Gly Ser Leu Asp Tyr Trp Gly Gln Gly Thr Leu
            100                 105                 110

Val Thr Val Ser Ser
        115

<210> SEQ ID NO 117
<211> LENGTH: 107
<212> TYPE: PRT
<213> ORGANISM: Artificial Sequence
<220> FEATURE:
<223> OTHER INFORMATION: anti-LAG-3_1E09_AM_2H01-VL -continued

```
<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Asn Leu Leu Ile
        35                  40                  45

Tyr Asp Ala Ser Thr Leu Glu Thr Gly Val Pro Ser Arg Phe Ser Gly
50                  55                  60

Ser Gly Tyr Gly Thr Asp Phe Thr Leu Thr Ile Ser Gly Leu Gln Pro
65                  70                  75                  80

Asp Asp Phe Ala Leu Tyr Tyr Cys Gln Gln Ser Tyr Ser Thr Pro Tyr
                85                  90                  95

Ser Phe Gly Pro Gly Thr Lys Val Glu Ile Lys
            100                 105

<210> SEQ ID NO 118
<211> LENGTH: 117
<212> TYPE: PRT
<213> ORGANISM: Artificial Sequence
<220> FEATURE:
<223> OTHER INFORMATION: anti-LAG-3_1E09_FR_1E05-VH

<400> SEQUENCE: 118

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Asp His
            20                  25                  30

Tyr Met Asn Trp Val Arg Gln Ala Pro Gly Lys Gly Leu Glu Trp Val
        35                  40                  45

Ala Tyr Ile Asp Thr Ser Ala Thr Tyr Ile Tyr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Asn Trp Gly Ser Leu Asp Tyr Trp Gly Gln Gly Thr Leu
            100                 105                 110

Val Thr Val Ser Ser
        115

<210> SEQ ID NO 119
<211> LENGTH: 107
<212> TYPE: PRT
<213> ORGANISM: Artificial Sequence
<220> FEATURE:
<223> OTHER INFORMATION: anti-LAG-3_1E09_FR_1E05-VL

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln His Lys Pro Gly Lys Ala Pro Lys Leu Leu Ile
        35                  40                  45

Tyr Asp Ala Ser Asn Leu Glu Thr Gly Ala Pro Ser Arg Phe Ser Gly
50                  55                  60
```

Ser Gly Ser Gly Thr Asp Phe Thr Phe Thr Ile Tyr Ser Leu Gln Pro
65                  70                  75                  80

Glu Asp Val Ala Thr Tyr Tyr Cys Gln Gln Tyr Asp Thr Val Pro Pro
                85                  90                  95

Thr Phe Gly Pro Gly Thr Lys Val Asp Ile Lys
            100                 105

<210> SEQ ID NO 120
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 120

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
                20                  25                  30

Val Thr Trp Gln His Gln Pro Asp Ser Gly Pro Pro Ala Ala Ala Pro
            35                  40                  45

Pro Gly Pro Arg Pro Pro Arg Pro His Pro Ala Ala Pro Ser Ser Trp
50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

<210> SEQ ID NO 121
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 121

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
                20                  25                  30

Val Thr Trp Gln His Gln Pro Asp Ser Gly Pro Pro Ala Ala Ala Pro
            35                  40                  45

Gly His Pro Leu Ala Pro Gly Pro Glu Pro Leu Ser Pro His Ser His
    50                  55                  60

Gly Pro Leu Pro Ala Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

<210> SEQ ID NO 122
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 122

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
                20                  25                  30

Val Thr Trp Gln His Gln Pro Asp Ser Gly Pro Pro Ala Ala Ala Pro
            35                  40                  45

Gly His Pro Leu Ala Pro Gly Pro His Pro Ala Ala Pro Ser Ser Trp
        50                  55                  60

Gly Pro Arg Pro Arg Arg Tyr Thr Val Leu Ser Val Gly Pro Gln Gly
65                  70                  75                  80

Leu Gln Ala Gly Arg Trp Pro Leu Arg Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

<210> SEQ ID NO 123
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 123

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
                20                  25                  30

Val Thr Trp Gln His Gln Pro Asp Ser Gly Pro Pro Ala Ala Ala Pro
            35                  40                  45

Gly His Pro Leu Ala Pro Gly Pro His Pro Ala Ala Pro Ser Ser Trp
        50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Ala Gly Arg Gln Arg Gly Asp Phe Ser Leu Trp Leu Arg Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Arg Leu Gly
    130                 135

```
<210> SEQ ID NO 124
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 124
```

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Lys Pro Ala Arg
            100                 105                 110

Arg Ala Asp Ala Gly Glu Tyr Arg Ala Ala Val His Leu Arg Asp Arg
        115                 120                 125

Ala Leu Ser Cys Arg Leu Arg Leu Gly
    130                 135

```
<210> SEQ ID NO 125
<211> LENGTH: 139
<212> TYPE: PRT
<213> ORGANISM: Artificial Sequence
<220> FEATURE:
<223> OTHER INFORMATION: The lg-V domain mutants of human LAG-3

<400> SEQUENCE: 125
```

Val Pro Val Val Trp Ala Gln Glu Gly Ala Pro Ala Gln Leu Pro Cys
1               5                   10                  15

Ser Pro Thr Ile Pro Leu Gln Asp Leu Ser Leu Leu Arg Arg Ala Gly
            20                  25                  30

Val Thr Trp Gln His Gln Pro Asp Ser Gly Pro Pro Ala Ala Ala Pro
        35                  40                  45

Gly His Pro Leu Ala Pro Gly Pro His Pro Ala Ala Pro Ser Ser Trp
    50                  55                  60

Gly Pro Arg Pro Arg Arg Tyr Thr Val Leu Ser Val Gly Pro Gly Gly
65                  70                  75                  80

Leu Arg Ser Gly Arg Leu Pro Leu Gln Pro Arg Val Gln Leu Asp Glu
                85                  90                  95

Arg Gly Arg Gln Arg Gly Asp Phe Ser Leu Trp Leu Arg Pro Ala Arg
            100                 105                 110

Arg Ala Asp Ala Gly Glu Tyr Arg Ala Gln Val His Tyr Glu Asp Gly
        115                 120                 125

Glu Leu Arg Cys His Leu Arg Leu Gly
    130                 135

MONOCLONAL ANTIBODY SPECIFICALLY BINDING TO LAG-3 AND USE THEREOF

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2019/007877, filed Jun. 28, 2019, which claims priority to the benefit of Korean Patent Application No. 10-2018-0075581 filed in the Korean Intellectual Property Office on Jun. 29, 2018, the entire contents of which are incorporated herein by reference.

TECHNICAL FIELD

The present invention relates to a monoclonal antibody which specifically binds to LAG-3 and a use thereof.

BACKGROUND ART

For a living organism, maintaining the immune homeostasis is most important to sustain its life. The immune homeostasis is controlled by a balance between the immune activating signal transduction system and immune suppressive signal transduction system. The immune suppressive signal transduction is activated by a protein which is referred to as an immune checkpoint, and, by maintaining the self-tolerance for an autoantigen or weakening the activity of T cells which have been activated after an immune response, it is one of the immune systems that are critical for protecting normal cells against an autoimmune response or an excessive inflammatory response. Meanwhile, by evading the T cell immunoreactivity using this immune suppressive signal transduction system, cells with chronic viral infection or cancer cells create a microenvironment that is advantageous for their thriving.

Until now, various immune checkpoint proteins are known including CTLA-4 (cytotoxic T-lymphocyte-associated protein 4), PD-1 (programmed cell death protein 1), TIM-3 (T cell immunoglobulin and mucin-domain containing-3), LAG-3 (lymphocyte activation gene 3), TIGIT (T cell immunoreceptor with immunoglobulin and immunoreceptor tyrosine-based inhibitory motif domains), and VISTA (v-domain Ig-containing suppressor of T cell activation). The immune evasion mechanism of cancer cells consists of binding to immune checkpoint proteins present on a surface of T cells and inactivating the T cells having killing activity (i.e., cytotoxic T cells). This provides a theoretical background of an immune checkpoint inhibitor, namely, according to restoration of the activity of weakened T cells by targeting the immune checkpoint proteins, cells with viral infection or cancer cells can be eliminated. Furthermore, it is known that the signal transduction pathways for various immune checkpoint proteins are unique and do not overlap with each other, and this is also the reason of having active studies for maximizing cancer therapy by reinforcing the immune activity of T cells according to co-use of an immune checkpoint inhibitor.

LAG-3 (lymphocyte activation gene 3) is one of the various immune checkpoint proteins such as CTLA-4, PD-1, or PD-L1, and it is a type I transmembrane protein consisting of 498 amino acids. LAG-3 gene is present on the $12^{th}$ human chromosome and close to CD4 (cluster of differentiation 4) gene. It is structurally close to CD-4 so that both proteins can bind to MHC (major histocompatibility complex) class II. However, the sequence homology between the amino acids of two proteins is less than 20%, and LAG-3 has much higher binding capacity for MHC class II compared to CD4. LAG-3 is composed of an extracellular domain, which consists of an immunoglobulin-like domain, a transmembrane domain, and an intracellular domain. In the extracellular domain, the first domain (Ig-like V-type domain) is critical for MHC class II binding, and it is known that, unlike CD4 having a broad range of binding site, LAG-3 has only few amino acids that are critical for MHC class II binding and the binding between LAG-3s is important for binding to MHC class II. The intracellular domain does not contain any ITIM (immunoreceptor tyrosine-based inhibitory motif) or ITSM (immunoreceptor tyrosine-based switch motif) and has relatively short length. Human and mouse LAG-3 has three characteristic structures, i.e., highly-conserved phosphorylation site of serine residue, KIEELE site, and glutamine-proline repeat sequence. Among them, KIEELE motif is known to play a key role in suppressing the activity of T cells.

When a mouse with deleted LAG-3 gene is treated with staphylococcal enterotoxin B (SEB), which is enterotoxin secreted from *Staphylococcus*, or egg white albumin, unregulated T cell growth and spleen enlargement are yielded. Increased expression of LAG-3 is shown, after T cell activation, in $CD4^+$, $CD8^+$ T cells and several natural killer cells. It has been reported that LAG-3 is expressed in greater amount in natural T regulatory cells (natural Treg cells) and induced $CD4^+FoxP3^+$ regulatory T cells (iTreg cells). Other than MHC class II, LSECtin (liver and lymph node sinusoidal endothelial cell C-type lectin) and galectin-3 are known as a LAG-3 binding protein (i.e., ligand), and it is also known that LSECtin and galectin-3 are expressed in cancer cells and tumor-infiltrating $CD8^+$ T cells, respectively, and inhibit the activity of T cells after binding to LAG-3 present in T-cells.

Under the aforementioned technical background, the inventors of the present invention carried out, by using a phage display technique, screening of monoclonal antibody specifically binding to human LAG-3 with use of the extracellular domain of human LAG-3 protein as an antigen. By determining that the monoclonal antibody prepared based on the variable region of heavy chain and light chain of the screened antibody clone can bind to human, monkey, or mouse LAG-3 protein with high affinity and can increase the activity of T cells by inhibiting the forming of LAG-3/MHC class II complex, the inventors completed the present invention.

SUMMARY

Object of the present invention is to provide a novel antibody for LAG-3 or an antigen-binding fragment thereof.

Another object of the present invention is to provide a polynucleotide encoding the aforementioned antibody or an antigen-binding fragment thereof.

Another object of the present invention is to provide a vector including the aforementioned nucleic acid, a transformant introduced with the vector, and a method for producing the same.

Still another object of the present invention is to provide a composition for treating cancer comprising the aforementioned antibody or an antigen-binding fragment thereof.

To solve the problems that are described above, the present invention provides a monoclonal antibody or an antigen-binding fragment thereof specifically binding to LAG-3 (lymphocyte-activation gene 3) including a heavy chain variable region comprising heavy chain CDR1 represented by SEQ ID NO: 1 or SEQ ID NO: 27; heavy chain CDR2 represented by SEQ ID NO: 2; and heavy chain CDR3 represented by SEQ ID NO: 3 and a light chain variable region comprising light chain CDR1 represented by SEQ ID NO: 8, SEQ ID NO: 53 or SEQ ID NO: 57; light chain CDR2 having the sequence of Asp Ala Ser; and light chain CDR3 represented by SEQ ID NO: 10, SEQ ID NO: 33 or SEQ ID NO: 60.

Furthermore, the present invention provides a polynucleotide encoding the heavy chain variable region and light chain variable region of the aforementioned antibody or an antigen-binding fragment thereof.

Furthermore, the present invention provides an expression vector including the aforementioned polynucleotide.

Furthermore, the present invention provides a transformant transformed with the aforementioned expression vector.

Furthermore, the present invention provides a method for preparing the aforementioned antibody or an antigen-binding fragment thereof by culturing the aforementioned transformant.

Furthermore, the present invention provides a pharmaceutical composition for treating cancer comprising, as an active ingredient, the aforementioned antibody or an antigen-binding fragment thereof.

Furthermore, the present invention provides a method for treating cancer including administering the aforementioned pharmaceutical composition for treating cancer to a subject.

Furthermore, the present invention provides a composition for diagnosing cancer comprising the aforementioned antibody or an antigen-binding fragment thereof, and a cancer diagnosis kit including the composition.

Furthermore, the present invention provides a drug conjugate in which a drug is conjugated to the aforementioned monoclonal antibody or an antigen-binding fragment thereof.

Furthermore, the present invention provides CAR (chimeric antigen receptor) protein including i) the aforementioned antibody, ii) transmembrane domain, and iii) intracellular signaling domain that is characterized to bring about T cell activation upon binding of the antibody of i) to an antigen.

Still furthermore, the present invention provides a multi-specific antibody including the aforementioned monoclonal antibody or an antigen-binding fragment thereof specifically binding to LAG-3.

As the novel antibody or an antigen-binding fragment thereof of the present invention specifically binding to LAG-3 can bind to LAG-3 to inhibit the LAG-3 activity, it is expected to be advantageously used for the development of immunotherapeutic agents for various disorders that are associated with LAG-3.

BRIEF DESCRIPTION OF THE DRAWINGS

FIG. 1 shows a schematic diagram (A) of the antigen protein used for preparing an antibody binding to LAG-3 protein, and confirmation results of purity (B) and activity (C) of the purified antigen protein.

FIG. 8 shows (A) LAG-3-mFc or -His fused proteins in which Ig-like V-type (Ig-V) domain of the extracellular domain of LAG-3 is cleaved (ΔIg-V) or a specific or non-specific amino acid within Ig-V domain is substituted with other amino acid, (B) the result of the purity determination by SDS-PAGE, and (C) the result of ELISA analysis to determine the binding specificity of human anti-LAG-3 monoclonal antibody 1E09.

FIG. 10 shows the result of enhancing T cell activity by 1E09 according to inhibition of the forming of LAG-3/MHC class II complex.

DETAILED DESCRIPTION

Figure 2:
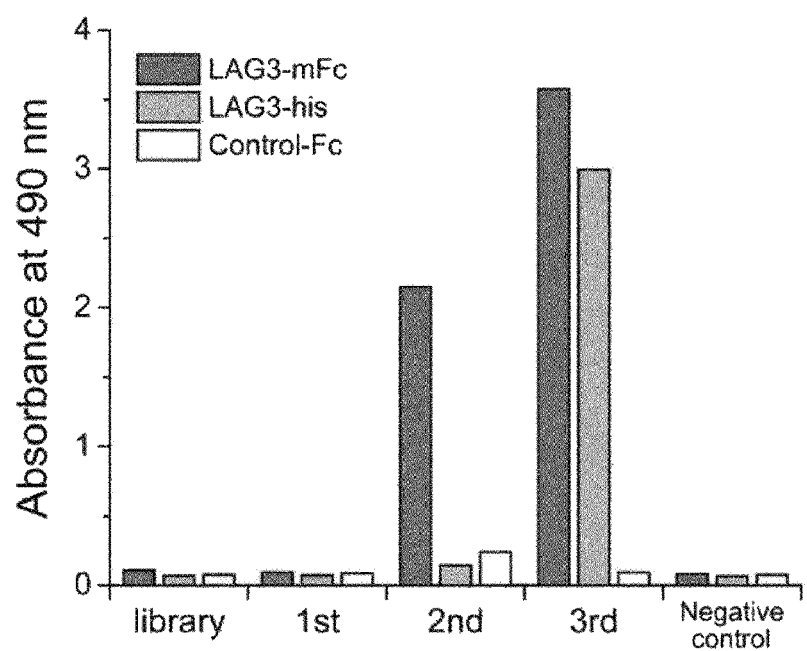
FIG. 2 shows the binding capacity of phage pool to LAG-3 in each round of panning.

To achieve the object of the present invention, provided is a monoclonal antibody or an antigen-binding fragment thereof which includes a heavy chain variable region comprising heavy chain CDR1 represented by SEQ ID NO: 1 or SEQ ID NO: 27; heavy chain CDR2 represented by SEQ ID NO: 2; and heavy chain CDR3 represented by SEQ ID NO: 3 and a light chain variable region comprising light chain CDR1 represented by SEQ ID NO: 8, SEQ ID NO: 53 or SEQ ID NO: 57; light chain CDR2 having the sequence of Asp Ala Ser; and light chain CDR3 represented by SEQ ID NO: 10, SEQ ID NO: 33 or SEQ ID NO: 60 and specifically binds to LAG-3.

The monoclonal antibody or an antigen-binding fragment thereof of the present invention is characterized in that it specifically binds to the extracellular domain of human, monkey, or mouse LAG-3 protein, and the monoclonal antibody or an antigen-binding fragment thereof of the present invention can inhibit the binding of LAG-3 to major histocompatibility complex (MHC) class II molecule, stimulate an immune response, or inhibit the binding of LAG-3 to MHC class II molecule and stimulate an immune response.

The monoclonal antibody or an antigen-binding fragment thereof specifically binding to LAG-3 according to one embodiment of the present invention may preferably consist of i) a heavy chain variable region comprising heavy chain CDR1 represented by SEQ ID NO: 1; heavy chain CDR2 represented by SEQ ID NO: 2; and heavy chain CDR3 represented by SEQ ID NO: 3 and a light chain variable region comprising light chain CDR1 represented by SEQ ID NO: 8; light chain CDR2 having the sequence of Asp Ala Ser; and light chain CDR3 represented by SEQ ID NO: 10, ii) a heavy chain variable region comprising heavy chain CDR1 represented by SEQ ID NO: 27; heavy chain CDR2 represented by SEQ ID NO: 2; and heavy chain CDR3 represented by SEQ ID NO: 3 and a light chain variable region comprising light chain CDR1 represented by SEQ ID NO: 53; light chain CDR2 having the sequence of Asp Ala Ser; and light chain CDR3 represented by SEQ ID NO: 33, or iii) a heavy chain variable region comprising heavy chain CDR1 represented by SEQ ID NO: 1; heavy chain CDR2 represented by SEQ ID NO: 2; and heavy chain CDR3 represented by SEQ ID NO: 3 and a light chain variable region comprising light chain CDR1 represented by SEQ ID NO: 57; light chain CDR2 having the sequence of Asp Ala Ser; and light chain CDR3 represented by SEQ ID NO: 60, and more preferably comprise i) a heavy chain variable region represented by the amino acid sequence of SEQ ID NO: 114 and a light chain variable region represented by the amino acid sequence of SEQ ID NO: 115, ii) a heavy chain variable region represented by the amino acid sequence of SEQ ID NO: 116 and a light chain variable region represented by the amino acid sequence of SEQ ID NO: 117, or iii) a heavy chain variable region represented by the amino acid sequence of SEQ ID NO: 118 and a light chain variable region represented by the amino acid sequence of SEQ ID NO: 119.

As described herein, the term "monoclonal antibody" means a protein molecule capable of specifically binding to a single antigenic site (i.e., single epitope) when it is presented thereto. The monoclonal antibody can be produced by various methods that are well known in the pertinent art.

In the present invention, the antibody means an antibody in whole form, in which the whole antibody has a structure with 2 whole-length light chains and 2 whole-length heavy chains and each light chain is connected to the heavy chain via disulfide bond. The whole-length antibody includes IgA, IgD, IgE, IgM and IgG, and IgG includes, as a subtype, IgG1, IgG2, IgG3 and IgG4. Furthermore, the heavy chain constant region includes gamma (γ), mu (μ), alpha (α), delta (δ) and epsilon (ε) types, and also, as a subclass, includes gamma1 (γ1), gamma2 (γ2), gamma3 (γ3), gamma4 (γ4), alpha1 (α1) and alpha2 (α2). Light chain constant region includes kappa (κ) and lambda (λ) types.

The monoclonal antibody of the present invention may be an antibody selected from the group consisting of a human antibody (fully human antibody), a humanized antibody, a chimeric antibody, a mouse antibody and a recombinant antibody and preferably a fully human antibody, but it is not limited thereto. Because the structure of fully human antibody entirely originates from a human, it is less likely to cause an immune response compared to a conventional humanized antibody or mouse antibody, and thus has an advantage of not causing an undesired immune response when administered to a human. Accordingly, it can be very advantageously used as a therapeutic antibody.

As described herein, the term "antigen-binding fragment" means a fragment which has an antigen binding function, and it includes Fab, F(ab'), F(ab')$_2$, and Fv. Among the antibody fragments, Fab has a structure including variable regions of light chain and heavy chain, a constant region of a light chain, and the first constant region of a heavy chain (CH1), and it has one antigen binding site. Fab' is different from Fab in that it has a hinge region including one or more cysteine residues at C terminus of heavy chain CH1 domain. F(ab')$_2$ antibody is generated as the cysteine residues of the hinge region of Fab' form a disulfide bond. Fv is a minimum antibody fragment which has only a heavy chain variable region and a light chain variable region, and the recombination technique for producing Fv fragment is described in International Publication WO1988/001649 or the like. In double chain Fv (dsFv), the heavy chain variable region and light chain variable region are linked to each other via a disulfide bond, and, in single chain Fv (scFv), the heavy chain variable region and light chain variable region are covalently linked to each other via a peptide linker in general. Those antibody fragments can be obtained by using a proteinase (e.g., Fab can be obtained by restriction digestion of a whole antibody with papain, and F(ab')$_2$ fragment can be obtained by restriction digestion of a whole antibody with pepsin), and it can be preferably produced by genetic engineering techniques.

As described herein, the term "variable region" means a region showing many mutations in the sequence while exhibiting the activity of specific binding to an antigen. In the variable region, CDR1, CDR2 and CDR3 are present as a complementarity determining region (CDR). Between those complementarity determining regions, a framework region (FR) is present to play the role of supporting the CDR loop.

As described herein, the term "CDR" indicates a loop-shaped region that is involved in antigen recognition, and, according to a variation in the sequence of this region, the specificity of an antibody for an antigen is decided.

According to one embodiment of the present invention, inventors of the present invention produced, by phage display method, a human antibody specifically binding to LAG-3 according to biopanning of a naive human single chain Fv library.

As described herein, the term "biopanning" indicates a process of selecting, from a phage library displaying a peptide on a phage coat, only the phages which display on a surface a peptide having a property of binding to a target molecule (e.g., antibody, enzyme, and cell surface receptor).

The monoclonal antibody or an antigen-binding fragment thereof of the present invention may be subjected to, although not particularly limited, either glycosylation and/or PEGylation to enhance the residence time in a living body to which the antibody is administered.

The term "glycosylation" described herein means a processing method for delivering a glycosyl group to a protein. The glycosylation is effected by binding of a glycosyl group to a serine, a threonine, an asparagine, or a hydroxylysine residue of a target protein as mediated by a glycosyl transferase. The glycosylated protein not only can be used as a constitutional material of a living tissue but also plays an important role in cell recognition on a cell surface. As such, according to the present invention, by modifying the glycosylation or pattern of the glycosylation of the monoclonal antibody or an antigen-binding fragment thereof of the present invention, effect of the antibody can be enhanced.

As described herein, the term "PEGylation" means a processing method for increasing the retention time of an antibody in blood by introducing polyethylene glycol to the aforementioned monoclonal antibody or an antigen-binding fragment thereof. Specifically, according to PEGylation of polymer nanoparticles with polyethylene glycol, hydrophilicity on a nanoparticle surface is enhanced, and, accordingly, fast degradation in living body can be prevented due to so-called stealth effect of preventing recognition by immune activity including macrophage in a human body to cause phagocytosis and digestion of pathogens, waste products, and foreign materials introduced from an outside. As such, the retention time of an antibody in blood can be increased by PEGylation. The PEGylation employed in the present invention can be carried out by a method by which an amide group is formed based on a bond between the carboxyl group of hyaluronic acid and the amine group of polyethylene glycol, but it is not limited thereto, and the PEGylation can be carried out by various methods. At that time, as for the polyethylene glycol to be used, polyethylene glycol having molecular weight of 100 to 1,000 and a linear or branched structure is preferably used, although it is not particularly limited thereto.

As for the glycosylation and/or PEGylation, modifications can be made by a method well known in the art to have various patterns of glycosylation and/or PEGylation as long as the function of the antibody of the present invention is maintained, and included in the antibody of the present invention are a variant monoclonal antibody with various modified pattern of glycosylation and/or PEGylation, or an antigen-binding fragment thereof.

The monoclonal antibody or an antigen-binding fragment thereof according to one embodiment of the present invention may be those capable of binding to human LAG-3 protein with $K_D$ of $1.5 \times 10^{-10}$M or less, binding to monkey LAG-3 protein with $K_D$ of $7.0 \times 10^{-10}$M or less, or binding to mouse LAG-3 protein with $K_D$ of $6.0 \times 10^{10}$M or less, but it is not limited thereto.

Also provided by the present invention is a polynucleotide encoding the heavy chain variable region and light chain variable region of the monoclonal antibody or an antigen-binding fragment thereof of the present invention.

Due to the codon degeneracy or in consideration of a codon preferred in an organism in which the light chain and heavy chain of human antibody or a fragment thereof is to be expressed, the polynucleotide encoding the light chain and heavy chain of the monoclonal antibody or an antigen-binding fragment thereof of the present invention can have various variations in the coding region within a range in which the amino acid sequence of the light chain and heavy chain of an antibody expressed from the coding region is not changed, and, even in a region other than the coding region, various changes or modifications can be made within a range in which the gene expression is not affected by them. A person skilled in the pertinent art may easily understand that those variant genes also fall within the scope of the present invention. Namely, as long as a protein having the equivalent activity is encoded, the polynucleotide of the present invention can be varied by having one or more nucleic acid bases changed by substitution, deletion, insertion, or a combination thereof, and those variants also fall within the scope of the present invention. Sequence of the polynucleotide may be either a single chain or a double chain, and it may be either a DNA molecule or an RNA (mRNA) molecule.

Also provided by the present invention is an expression vector including the polynucleotide which encodes the heavy chain variable region and light chain variable region of the monoclonal antibody or an antigen-binding fragment thereof of the present invention.

As described herein, the term "expression vector" used herein means a gene construct comprising an essential regulatory element that is operably linked such that the gene insert can be expressed, and it includes a plasmid vector; and a virus vector such as cosmid vector, adenovirus vector, retrovirus vector, and adeno-associated virus as a means for expressing a target gene in a host cell. As described herein, the expression "operably linked" means that a sequence for regulating the expression of a nucleic acid and a polynucleotide encoding the target protein are functionally linked to each other so as to exhibit a general function. The operable link to an expression vector can be achieved by a gene recombination technique well known in the art, and the site-specific DNA digestion and ligation can be easily carried out by using enzymes or the like that are generally known in the corresponding technical field.

The expression vector preferred in the present invention may include, other than an expression regulatory element like a promoter, an initiation codon, a termination codon, a polyadenylation signal, and an enhancer, a signal sequence for membrane targeting or secretion. The initiation codon and termination codon are generally regarded as part of a nucleotide sequence which encodes an immunogenic target protein, and, when a gene construct is administered, the activity should be shown in the individual and the codons should be in-frame with a coding sequence. A general promoter may be either a constitutive promoter or an inducible promoter. For a prokaryotic cell, there are lac, tac, T3 and T7 promoters, but not limited thereto. For an eukaryotic cell, there are β-actin promoter, promoters originating from human hemoglobin, human muscle creatine, or human metallothionein as well as simian virus 40 (SV40) promoter, mouse mammary tumor virus (MMTV) promoter, human immunodeficiency virus (HIV) promoter, HIV long terminal repeat (LTR) promoter, Moloney virus promoter, cytomegalovirus (CMV) promoter, Epstein-barr virus (EBV) promoter, Rous sarcoma virus (RSV) promoter, but it is not limited thereto.

A selective marker may be included in the expression vector for selecting a host cell which includes a vector. The selective marker is used for selecting cells that are transformed by a vector, and markers yielding selectable phenotypes like drug resistance, auxotrophy, or resistance to cytotoxic agent, or expression of a surface protein can be used. Because only a cell expressing the selective marker would survive in a selective agent-treated environment, it is possible to select transformed cells.

Furthermore, in case of a replicable expression vector, the vector may include a replication origin as a specific polynucleotide from which the replication starts. It is also possible to use a virus (e.g., baculovirus) or a phage vector, and a vector that can be inserted to a genome of a host cell like retrovirus. The vector expressing the whole antibody or antibody fragment can be any one of vector system in which the light chain and heavy chain are expressed simultaneously in one vector or a vector system in which each of the light chain and heavy chain is expressed in separate vector.

In the latter case, the two vectors are introduced to a host cell by cotransformation and targeted transformation, the cells transformed with a vector including the light chain (or heavy chain) are selected, and the selected cells expressing the light chain are transformed again with a vector including the heavy chain (or light chain) so that the cells expressing both the light chain and heavy chain are finally selected.

To prepare an antibody in Fab form, a vector added with a gene encoding the amino acids of the variable region (VL) and constant region (CL) of human light chain, and variable region (VH) and the first constant region domain (CH1) of human heavy chain is used.

Also provided by the present invention is a transformant transformed with the aforementioned expression vector.

The host cell that is suitable for the aforementioned vector can be a prokaryotic cell like *Escherichia coli, Bacillus subtilis, Streptomyces* sp., *Pseudomonas* sp., *Proteus mirabilis*, and *Staphylococcus* sp. Moreover, it can be an eukaryotic cell like fungus including *Aspergillus* sp., yeast including *Pichia pastoris, Saccharomyces cerevisiae, Schizosaccharomyces* sp., and *Neurospora crassa*, cells of lower eukaryotes, cells of higher eukaryotic organism like insect cells, or plant cells. The host cell may originate from mammals. Preferably, the host cell can be COS-7, BHK, CHO, CHOK1, DXB-11, DG-44, CHO/−DHFR, CV1, COS-7, HEK293, BHK, TM4, VERO, HELA, MDCK, BRL3A, W138, HepG2, SK-Hep, MMT, TRI, MRC 5, FS4, 3T3, RIN, A549, PC12, K562, PER.C6, SP2/0, NS-0, U20S or HT1080, but it is not limited thereto.

"Transformation of a host cell" described in the present invention can be carried out by a standard technique that is known in the corresponding technical field to be suitable for each host cell, and any method for introducing a nucleic acid to an organism, a cell, a tissue, or an organ is included therein. Included in the method is electroporation, cytoplasmic fusion, calcium phosphate ($CaPO_4$) precipitation, calcium chloride ($CaCl_2$) precipitation, stirring using silicon carbide fiber, *Agrobacterium*-mediated transformation, transformation mediated by PEG, dextran sulfate, lipofectamine, and drying/suppression, but it is not limited thereto.

Also provided by the present invention is a method for producing a monoclonal antibody or an antigen-binding fragment thereof specifically binding to LAG-3 including:
(a) preparing a culture broth by culturing a transformant; and
(b) purifying a monoclonal antibody or an antigen-binding fragment thereof of the present invention from the culture broth of above (a).

In the production method, the culture of a transformant can be performed using a suitable medium and culture conditions that are known in the pertinent art. The culture process can be employed with easy adjustment by a skilled person depending on bacterial strains or animal cells that are selected.

The antibody obtained by culturing the transformant can be used in a non-purified state. Impurities can be removed by additional various commons methods like centrifuge or ultrafiltration, and the resultant may be subjected to dialysis, salt precipitation, chromatography or the like, in which the method may be used either singly or in combination thereof. Among them, affinity chromatography is most widely used, and there are ion exchange chromatography, size exclusion chromatography, hydrophobic interaction chromatography, hydroxyapatite chromatography, or the like.

The antibody produced according to the above method is an antibody having enhanced affinity for an antigen. The term "affinity" indicates a property of specifically recognizing and binding to a specific antigen site, and, together with specificity of an antibody for an antigen, the high affinity is an important factor in an immune reaction. In the present invention, humanized heavy chain library cells are produced by random mutation of a heavy chain variable region, and a colony lift assay was carried out for the library cells to select first the variant clones having high antigen binding capacity. By carrying out competitive ELISA for the selected clones, affinity of each clone was examined. Other than this method, various methods for measuring the affinity for an antigen may be employed, and the surface plasmon resonance technology is one example of those methods.

The term "$K_D$" used herein means a dissociation constant of a specific antibody-antigen interaction, and it is used as an indicator for measuring the affinity of an antibody for an antigen. Lower $K_D$ value means higher affinity of an antibody for the antigen.

Also provided by the present invention is a composition for stimulating an immune response comprising the monoclonal antibody or an antigen-binding fragment thereof of the present invention as an active ingredient. Because the antibody of the present invention specifically binding to LAG-3 can inhibit the binding of LAG-3 to MHC class II molecule, stimulate an immune response, or inhibit the binding of LAG-3 to MHC class II molecule and stimulate an immune response, the composition comprising, as an active ingredient, the monoclonal antibody or an antigen-binding fragment thereof of the present invention which is specific to LAG-3 can stimulate an immune response.

Also provided by the present invention is a pharmaceutical composition for treating cancer comprising, as an active ingredient, the monoclonal antibody or an antigen-binding fragment thereof.

As the antibody of the present invention can bind with high affinity to LAG-3, which reduces the activity of T lymphocytes, by blocking the interaction between MHC and T cell receptor, the antibody may inhibit the activity of LAG-3 and enhance the activity of T lymphocytes to simulate an immune response. The monoclonal antibody or an antigen-binding fragment thereof is the same as those described in the above.

As for the term "cancer" used herein, any cancer that can be treated by the human antibody of the present invention is included without any limitation. Examples thereof include liver cancer, breast cancer, kidney cancer, brain tumor, biliary tract cancer, esophageal cancer, stomach cancer, colon cancer, rectal cancer, oral cancer, pharyngeal cancer, larynx cancer, lung cancer, ascending colon cancer, cervical cancer, thyroid cancer, leukemia, Hodgkin disease, lymphoma, and multiple myeloma blood cancer, but it is not limited thereto.

Each composition provided by the present invention may contain a pharmaceutically acceptable carrier. As described herein, the expression "pharmaceutically acceptable carrier" means a carrier or a diluent which does not inhibit the biological activity and characteristics of a compound for administration without stimulating a living organism. As a pharmaceutically acceptable carrier in the composition which is prepared as a liquid solution, physiological saline, sterilized water, buffered saline, albumin injection solution, dextrose solution, maltodextrin solution, glycerol, and a mixture of one or more of them can be used as a sterilized carrier suitable for a living organism. If necessary, common additives like anti-oxidant, buffer solution, and bacteriostat may be added. Furthermore, by additionally adding a diluent, a dispersant, a surfactant, a binder, or a lubricant, the composition can be prepared as a formulation for injection like aqueous solution, suspension, and emulsion, a pill, a capsule, a granule, or a tablet.

The pharmaceutical composition comprising the antibody and a pharmaceutically acceptable carrier for treating cancer can be applied in any formulation comprising the antibody as an active ingredient, and it can be prepared as an oral preparation or a parenteral preparation. The pharmaceutical formulation of the present invention includes a formulation that is suitable for oral, rectal, nasal, topical (including cheek and under tongue), subcutaneous, vaginal, or parenteral (including intramuscular, subcutaneous, and intravenous) administration, and a formulation that is suitable for administration by inhalation or insufflation.

The formulation for oral administration which comprises the composition of the present invention as an active ingredient may be formulated into a tablet, a troche, a lozenge, a water soluble or oily suspension, a powder or granule, an emulsion, a hard or soft capsule, a syrup, or an elixir. For preparing a formulation like tablet and capsule, a binder like lactose, saccharose, sorbitol, mannitol, starch, amylopectin, cellulose, or gelatin, a vehicle such as dicalcium phosphate, a disintegrating agent like corn starch and sweet potato starch, or a lubricating oil like magnesium stearate, calcium stearate, sodium stearylfumarate, or polyethylene glycol wax may be further comprised. In case of a capsule formulation, a liquid carrier like lipid oil may be further comprised in addition to the aforementioned materials.

As for the formulation for parenteral administration comprising the composition of the present invention as an active ingredient, the formulation can be prepared as an injection formulation for subcutaneous injection, venous injection, or intramuscular injection, suppository injection, or a spray formulation like aerosol which allows inhalation via respiratory organ. For preparing a formulation for injection, the composition of the present invention is admixed with a stabilizer or a buffer in water to give a solution or a suspension, and the resultant may be formulated as a unit dose in ampoule or vial. To have injection as a suppository, formulation into a composition for colorectal administration like suppository or enema comprising common suppository base like cocoa butter or other glycerides can be made. For preparing a spray formulation like aerosol, a water-dispersed concentrate or a propellant for dispersing wet powder may be blended with additives.

The composition of the present invention enables the inhibition of tumor growth in a subject when the antibody of the present invention is administered to a subject.

The pharmaceutical composition of the present invention may additionally comprise an immunostimulatory antibody, which is preferably at least one selected from the group consisting of anti-PD-1 antibody, anti-PD-L1 antibody and anti-CTLA-4 antibody, and more preferably anti-PD-L1 antibody, but it is not limited thereto.

Also provided by the present invention is a method for treating cancer including administering the pharmaceutical composition comprising the monoclonal antibody or an antigen-binding fragment thereof for treating cancer to a subject.

As described herein, the term "administration" means introduction of the pharmaceutical composition of the present invention to a patient via a certain suitable method. The administration route of the composition of the present invention can be various routes including oral and parenteral routes as long as it allows delivery of the composition to a target tissue. Specifically, the administration can be made by a common method via oral, colorectal, topical, intravenous, intraperitoneal, intramuscular, intraarterial, percutaneous, intranasal, inhaling, intraocular, or intradermal route.

The treatment method of the present invention includes administering the composition for treating cancer of the present invention in a pharmaceutically effective amount. It would be evident for a person who is skilled in the art that a suitable total daily dose can be determined by a clinician within a range of proper medical determination. It is preferable that the specific therapeutically effective amount for a certain patient is differently set depending on type and level of a response to be achieved, a specific composition including whether or not other formulation is used depending on a case, age, bodyweight, general health state, sex, and diet of a patient, administration time, administration route, and secretion rate of a composition, treatment period, various factors including a pharmaceutical which is used either together or simultaneously with a specific composition and similar factor that are well known in a medical field. Thus, the effective amount of the composition for prevention or treatment of cancer that is appropriate for the purpose of the present invention is preferably determined in consideration of the aforementioned items.

Furthermore, the subject means any animal which may have an occurrence of a disease like tumor development and angiogenesis due to excessive activity of LAG-3, and included in the animal are not only human and primates but also livestock like cow, pig, sheep, horse, dog, and cat.

Also provided by the present invention is a composition for cancer diagnosis comprising the anti-LAG-3 antibody or an antigen-binding fragment thereof of the present invention, and a cancer diagnosis kit including the composition.

The monoclonal antibody or an antigen-binding fragment thereof and cancer are the same as those described in the above. By using the composition for diagnosis comprising the LAG-3-specific monoclonal antibody or an antigen-binding fragment thereof of the present invention, a disorder related with expression or expression level of LAG-3, for example, cancer, can be diagnosed.

According to the method for cancer diagnosis, the LAG-3-specific monoclonal antibody of the present invention is reacted with a biological sample isolated from an individual with suspected cancer, and forming of an antigen-antibody complex is analyzed for detection, and thus information for cancer diagnosis can be provided.

As described herein, the term "biological sample" means tissues, cells, whole blood, blood serum, blood plasma, biopsy tissue samples (brain, skin, lymph node, bone marrow, or the like), supernatant of cell culture, disrupted eukaryotic cells, and cell expression system, but not limited thereto. It is possible that those biological samples, either in processed state or non-processed state, are reacted with the antibody of the present invention to examine the presence of LAG-3 or occurrence of cancer.

As described herein, the expression "antigen-antibody complex" means a complex between LAG-3 protein antigen in a sample and the monoclonal antibody or an antigen-binding fragment thereof of the present invention for recognizing an antigen, and forming of the antigen-antibody complex can be measured by common immunoassay, i.e., measurement can be made by radioimmunoassay, radioimmunoprecipitation, immunoprecipitation, immunohistochemical staining, ELISA (enzyme-linked immunosorbent assay), capture-ELISA, inhibitory or competitive assay, sandwich assay, flow cytometry, immunofluorescent staining, or immunoaffinity purification using the antibody for LAG-3, but it is not limited thereto.

By analyzing the intensity of final signal according to the aforementioned immunoassay process, cancer diagnosis can be achieved. Namely, when LAG-3 protein of the present invention is overexpressed in a biological sample separated from an individual with suspected conditions so that the signal is higher than a biological sample separated from a normal individual, the individual is diagnosed with cancer.

Furthermore, the kit according to the present invention includes the antibody of the present invention for LAG-3, and, by analyzing the signal which is exhibited upon a reaction between the antibody and a sample, cancer diagnosis can be made. At that time, the signal may include an enzyme conjugated to the antibody, e.g., alkaline phosphatase, β-galactosidase, horse radish peroxidase, luciferase, or cytochrome P450, but it is not limited thereto. As for the substrate for an enzyme, when alkaline phosphatase is used as an enzyme, a chromogenic substrate like bromochloroindole phosphate (BCIP), nitroblue tetrazolium (NBT), naphthol-AS-B1-phosphate, and ECF (enhanced chemifluorescence) can be used as a substrate. When horse radish peroxidase is used, a substrate like chloronaphthol, aminoethylcarbazole, diaminobenzidine, D-luciferin, lucigenin (bis-N-methylacridinium nitrate), resolufin benzyl ether, luminol, Amplex red reagent (10-acetyl-3,7-dihydroxyphenoxazine), HYR (p-phenylenediamine-HCl and pyrocatechol), TMB (tetramethylbenzidine), ABTS (2,2'-azine-di[3-ethylbenzthiazoline sulfonate]), o-phenylenediamine (OPD) and naphthol/pyronin, glucose oxidase and t-NBT and m-PMS (phenzaine methosulfate) can be used, but it is not limited thereto.

Furthermore, the kit of the present invention may include a label for generating detectable signal, and examples of the label include a chemical substance (e.g., biotin), an enzyme (e.g., alkaline phosphatase, β-galactosidase, horse radish peroxidase, and cytochrome P450), a radioactive material (e.g., $^{14}C$, $^{125}I$, $^{32}P$ and $^{35}S$), a fluorescence material (e.g., fluorescein), a luminescent, a chemiluminescent and FRET (fluorescence resonance energy transfer), but it is not limited thereto.

Measurement of enzyme activity and signal measurement used for cancer diagnosis can be carried out by various methods that are well known in the pertinent art. Accordingly, expression of LAG-3 can be analyzed either quantitatively or qualitatively.

Also provided by the present invention is an antibody-drug conjugate having a drug conjugated to the monoclonal antibody or an antigen-binding fragment thereof of the present invention.

As described herein, the term "drug" means a compound that can be conjugated to the LAG-3-specific antibody or an antigen-binding fragment thereof of the present invention, dissociate from the antibody or an antigen-binding fragment thereof under acidic conditions, and exhibit a therapeutic effect for target cells.

The drug that can be used for the antibody-drug conjugate of the present invention includes any compound, a part, or a residue having cytotoxic effect or inhibitory effect on cell proliferation, and included therein are (i) chemotherapeutic agent capable of functioning as a microtubulin inhibitor, a mitotic inhibitor, a topoisomerase inhibitor, or a DNA interchelator; (ii) protein toxin capable of functioning enzymatically; and (iii) radioisotopes (radioactive nuclide). At least one of those compounds can be used.

Non-limiting examples of the drug include maytansinoid, auristatin, dolastatin, trichothecene, CC1065, calicheamicin, and other enediyne antibiotics, taxan, anthracycline, methotrexate, adriamycin, vindesine, vinca alkaloid (vincristine, vinblastine, etoposide), doxorubicin, melphalan, mitomycin C, chlorambucil, daunorubicin, daunomycin, etoposide, teniposide, carminomycin, aminopterine, dactinomycin, mytomycins, bleomycins, esperamicins, 5-fluorouracil, melphalan, other nitrogen mustard and stereoisomers, isosteres, analogues, or derivatives thereof, cis-platinum and cis-platinum analogues, and other enzymes as an intercalation agent and fragments thereof, e.g., nuclease, antibiotics, toxin (enzymatically active toxin originating from bacteria, fungi, plant or animal, or small-molecule toxin), and various anti-tumor or anti-cancer agents like cisplatin, CPT-11, doxorubicin, paclitaxel, and docetaxel, but it is not limited thereto. Furthermore, examples of radioisotopes (i.e., radioactive nuclide) include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$, but not limited thereto. A micro RNA (miRNA), siRNA and shRNA or the like, which can inhibit the expression of a specific oncogene, can be also used.

Also provided by the present invention is a CAR (chimeric antigen receptor) protein including i) the antibody of the present invention; ii) a transmembrane domain, and; iii) an intracellular signaling domain that is characterized to bring about T cell activation upon binding of the antibody of i) to an antigen.

In the present invention, the CAR protein can be characterized in that it is constituted by the monoclonal antibody of the present invention, a publicly known transmembrane domain, and an intracellular signaling domain.

As described herein, the term "CAR (chimeric antigen receptor)" means a non-natural receptor capable of providing specificity for a specific antigen to an immunoeffector cell. In general, the CAR indicates a receptor that is used for providing the specificity of a monoclonal antibody to T cells. CAR is generally constituted with an extracellular domain, a transmembrane domain, and an intracellular domain.

The extracellular domain includes an antigen recognition region, and, in the present invention, the antigen recognition site is LAG-3-specific antibody. The LAG-3-specific antibody is as described in the above, and the antibody used in CAR is preferably in the form of an antibody fragment. It is more preferably in the form of Fab or scFv, but not limited thereto.

Furthermore, the transmembrane domain of CAR has the form in which it is connected to the extracellular domain, and it may be originated from either natural or synthetic form. When it is originated from natural form, it may be originated from a membrane-bound or transmembrane protein, and it can be a part originated from transmembrane domains of various proteins like alpha, beta or zeta chain of T cell receptor, CD28, CD3 epsilon, CD45, CD4, CD5, CD8, CD9, CD16, CD22, CD33, CD37, CD64, CD80, CD86, CD134, CD137, CD154 or CD8. Sequences of those transmembrane domains can be obtained from documents that are well known in the art, in which the transmembrane domain of a transmembrane protein is described well, but it is not limited thereto.

Furthermore, in a case in which the aforementioned transmembrane domain is a synthetic one, it may comprise mainly a hydrophobic amino acid such as leucine or valine. For example, triplet of phenylalanine, tryptophan, and valine may be present in the transmembrane domain, but it is not limited thereto.

In the CAR of the present invention, the intracellular domain is part of the CAR domain present inside a cell, and it has the form in which it is connected to the transmembrane domain. The intracellular domain of the present invention may include an intracellular signaling domain, which is characterized by having a property of causing T cell activation, preferably T cell proliferation, upon binding of an antigen to the antigen recognition site of CAR. The intracellular signaling domain is not particularly limited in terms of the type thereof as long as it can cause the T cell activation upon binding of an antigen to the antigen recognition site of CAR present outside a cell, and various kinds of an intracellular signaling domain can be used. Examples thereof include immunoreceptor tyrosine-based activation motif (ITAM), and the ITAM may include those originating from CD3 zeta (ξ), FcR gamma, FcR beta, CD3 gamma, CD3 delta, CD3 epsilon, CDS, CD22, CD79a, CD79b, CD66d or FcεRIγ, but not limited thereto.

Furthermore, it is preferable that the intracellular domain of the CAR of the present invention additionally comprises a costimulatory domain with the intracellular signaling domain, but it is not limited thereto. The costimulatory domain is a part which is comprised in the CAR of the present invention and plays a role of transferring a signal to T cells in addition to the signal from the intracellular signaling domain, and it indicates the intracellular part of CAR including the intracellular domain of a costimulatory molecule.

The costimulatory molecule means, as a cell surface molecule, a molecule required for having a sufficient reaction of lymphocytes for an antigen, and examples thereof include CD27, CD28, 4-1BB, OX40, CD30, CD40, PD-1, ICOS, LFA-1 (lymphocyte function-associated antigen-1), CD2, CD7, LIGHT, NKG2C, and B7-H3, but not limited thereto. The costimulatory domain can be an intracellular part of a molecule that is selected from the group consisting of those costimulatory molecules and a combination thereof.

Furthermore, selectively, a short oligopeptide or polypeptide linker may link the intracellular domain and transmembrane domain of CAR. Although this linker may be included in the CAR of the present invention, it is not particularly limited in terms of the linker length as long as it can induce the T cell activation via the intracellular domain binding of an antigen to an extracellular antibody.

Also provided by the present invention is a multi-specific antibody including the monoclonal antibody or an antigen-binding fragment thereof specifically binding to LAG-3.

In the present invention, the multi-specific antibody can be preferably a bi-specific antibody, but it is not limited thereto.

The multi-specific antibody according to the present invention preferably has the form in which the anti-LAG3 antibody of the present invention is bound to an antibody having a binding property for an immunoeffector cell-specific target molecule, or a fragment thereof. The immunoeffector cell-specific target molecule is preferably selected from PD-1, PD-L1, CTLA-4, TIM-3, TIGIT, BTLA, KIR, A2aR, VISTA, B7-H3, TCR/CD3, CD16 (FcγRIIIa) CD44, CD56, CD69, CD64 (FcγRI), CD89 and CD11b/CD18 (CR3), but it is not limited thereto.

The multi-specific antibody is an antibody which can simultaneously recognize different multi- (bi or higher) epitopes of the same antigen or two or more separate antigens, and the antibodies belonging to multi-specific antibody can be classified into scFv-based antibody, Fab-based antibody, IgG-based antibody, or the like. In case of a multi-specific, e.g., bi-specific, antibody, two signals can be simultaneously suppressed or amplified, and thus it can be more effective than a case in which one signal is suppressed/amplified. Compared to a case in which each signal is treated with a signal inhibitor for each, low-dose administration can be achieved and two signals can be suppressed/amplified at the same time in the same space.

Method for producing a bi-specific antibody is widely known. Conventionally, recombination production of a bi-specific antibody is based on coexpression of a pair of heavy chain/light chain of two immunoglobulins under conditions at which two heavy chains have different specificity.

In case of a scFv-based bi-specific antibody, by combining VL and VH of different scFvs, a hybrid scFv-based is prepared in heterodimer form to give a diabody (Holliger et al., Proc. Natl. Acad. Sci. U.S.A., 90:6444, 1993), and, by connecting different scFvs to each other, tandem ScFv can be produced. By expressing CH1 and CL of Fab at the terminus of each scFv, a heterodimeric mini antibody can be produced (Muller et al., FEBS lett., 432:45, 1998). In addition, by substituting partial amino acids of CH3 domain as a homodimeric domain of Fc, a structural change into "knob into hole" form to have a heterodimer structure is made and those modified CH3 domains are expressed at the terminus of each different scFv, and thus a minibody in heterodimeric scFv form can be produced (Merchant et al., Nat. Biotechnol., 16:677, 1998).

In case of a Fab-based bi-specific antibody, according to combination of separate Fab' for a specific antigen by utilizing a disulfide bond or a mediator, the antibody can be produced in heterodimeric Fab form, and, by expressing scFv for a different antigen at the terminus of a heavy chain or a light chain of a specific Fab, the antigen valency of 2 can be obtained. In addition, by having a hinge region between Fab and scFv, the antigen valency of 4 can be obtained in homodimer form. In addition, a method of producing the followings is known in the pertinent art: a dual target bibody by which the antigen valency of 3 is obtained according to fusion of scFv for a different antigen at the light chain terminus and heavy chain terminus of Fab, a triple target bibody by which the antigen valency of 3 is obtained according to fusion of different scFvs to the light chain terminus and heavy chain terminus of Fab, and a triple target antibody F(ab')$_3$ in simple form that is obtained by chemical fusion of three different Fabs.

In case of IgG-based bi-specific antibody, a method of producing bi-specific antibody by preparing hybrid hybridoma, so-called quadromas, based on re-hybridization of mouse and rat hybridomas is known by Trion Pharma. In addition, a method of producing a bi-specific antibody in so-called "Holes and Knob" form, in which partial amino acids of the CH3 homodimeric domain of Fc in different heavy chains are modified while sharing the light chain part, is known (Merchant et al., Nat. Biotechnol., 16:677, 1998), and, other than the bi-specific antibody in heterodimer form, a method of producing (scFv)4-IgG in homodimer form according to fusion of two different scFvs to the constant domain of the light chain and heavy chain of IgG instead of the variable domain, followed by expression, is known. Furthermore, it has been reported by ImClone Systems that, based on IMC-1C11 as a chimeric monoclonal antibody for human VEGFR-2, only a single variable domain for mouse platelet-derived growth factor receptor-α is fused to the amino terminus of the light chain of the antibody so as to produce a bi-specific antibody. Furthermore, an antibody having high antigen valency for CD20 has been reported by Rossi et al. based on so-called "dock and lock (DNL)" method using a dimerization and docking domain (DDD) of protein kinase A (PKA) R subunit and an anchoring domain of PKA (Rossi et al., Proc. Natl. Acad. Sci. U.S.A., 103: 6841, 2006).

Hereinbelow, the present invention is explained in detail in view of the examples. However, the following examples are given only for exemplification of the present invention, and it is evident that the present invention is not limited to the following examples.

EXAMPLES

Example 1. Production, Purification, and Activity Determination of LAG-3 Antigen 1-1. Construction of Vector for Expressing LAG-3 Antigen Protein For cloning the LAG-3 protein, amplification was carried out with LAG-3 gene cDNA clone plasmid (#HG16498-G, Sino Biological Inc, China) by polymerase chain reaction (PCR) using primers for LAG-3 (Table 1), which include restriction enzyme sites Sfi I at 5' and 3' for obtaining only the extracellular domain (29th to 450th amino acid sequence). The amplified PCR product was fused at the carboxy terminal with mouse Fc (mFc) using the expression vector (A of FIG. 1).

TABLE 1

| PCR primers for LAG-3 cloning | |
|---|---|
| Primer Name | SEQ ID NO: (5'→3') |
| LAG-3-F | gtcccggtggtgtgggcccaggag (SEQ ID NO: 112) |
| LAG-3-R | gaggtggcctgctgggagggcacc (SEQ ID NO: 113) |

1-2. Expression and Purification of LAG-3 Antigen Protein

By using PEI (polyethylenimine: #23966, Polysciences, USA), HEK293F cells (Invitrogen, USA) were transfected with the prepared LAG-3 antigen plasmid. Thereafter, the cells were cultured for 7 days in FREESTYLE 293 Expression Medium (#AG100009, Thermo Fisher Scientific, USA), which is a serum-free medium. The cell culture broth containing the LAG-3 protein was collected and centrifuged for 10 minutes at 5,000 rpm, and the residual cells and floating materials were removed by using a 0.22 μm TOP-filter (Millipore, USA). Based on affinity chromatography using protein A agarose resin, purification of the LAG-3 protein was carried out. The protein obtained after the first purification was subjected to the second purification using SUPERDEX 200 (1.5 cm×100 cm) gel filtration chromatography.

Purity of the purified protein was determined by SDS-PAGE (sodium dodecyl sulfate polyacrylamide gel electrophoresis) at reducing or non-reducing conditions. As a result, the purity of the purified LAG-3-mFc protein was found to be 95% or higher as it is shown in B of FIG. 1.

1-3. Determination of Activity of LAG-3 Antigen Protein

Activity of the purified LAG-3-mFc protein was determined by the protein binding to Daudi (human B cell line) which expresses MHC class II as LAG-3 receptor. Specifically, $5 \times 10^5$ Daudi cells (#10213, Korean Cell Line Bank, Korea) were reacted with 10 μg/ml LAG-3-mFc or 200 μg/ml anti-human HLA-DR, DP, DQ (#555556, BD, USA) antibody, which is MHC class II antibody (blocking antibody), at 4° C. for 45 minutes. After that, the cells were washed three times with PBS (phosphate buffered saline: #LB001-02, Welgene, Korea) containing 2% fetal bovine serum (FBS) (#26140-079, Thermo Fisher Scientific), and then treated for 30 minutes at 4° C. with human anti-LAG-3 antibody (#565616, BD Biosciences, USA) tagged with PE (phycoerythrin) fluorescent for determining LAG-3 bound on the cell surface. The same washing process as above was carried out again, and, after suspending in 0.2 ml PBS containing 2% FBS, the cells were subjected to flow cytometry analysis using FACSCanto II (BD Biosciences).

As a result, it was shown that the purified LAG-3-mFc protein binds well to Daudi cells, and, when blocking is carried out by a treating with the antibody against MHC class II, lower binding was observed (C of FIG. 1). This result indicates that the purified LAG-3-mFc protein can bind to MHC class II expressed on cell surface and has an activity based on its structure.

Example 2. Selection of Human Anti-LAG-3 Antibody 2-1. Biopanning

LAG-3-mFc prepared in Example 1 and LAG-3-his (#16498-H08H) protein antigen, which has been purchased from Sino Biological Inc., were coated (50 μg) on an immunosorb tube followed by blocking.

With regard to the human antibody library phage, bacteria were infected with human scFv (single-chain variable fragment) library having $2.7 \times 10^{10}$ variety, and then cultured for 16 hours at 30° C. After the culture, centrifuge was carried out to concentrate the supernatant with PEG (polyethylene glycol, Sigma), and the resultant was dissolved in PBS buffer to prepare a human antibody library. The library phage was added to the immunosorb tube and the reaction was allowed to occur for 2 hours at room temperature. Then, after washing with 1×PBS-Tween20 (PBS-T) and 1×PBS, only the scFv-phages specifically bound to the antigen were eluted. Through the panning process in which bacteria are infected again with the eluted phages for amplification, a pool of positive phage was obtained. The second and third round pannings were carried out in a similar manner, and the number of input phages and bound phages for each panning round are as shown in Table 2.

TABLE 2

| Comparison of antibody titer on each panning round | | |
|---|---|---|
| Number of panning | Number of input phages | Number of bound phages |
| 1 time | $8 \times 10^{12}$ | $8 \times 10^6$ |
| 2 times | $3 \times 10^{12}$ | $5 \times 10^5$ |
| 3 times | $4 \times 10^{12}$ | $1 \times 10^5$ |

2-2. Polyphage ELISA

In order to examine the antigen-specificity of the positive poly scFv-phage antibody pool, which has been obtained from the panning process of each round of Example 2-1, polyphage ELISA (enzyme linked immunoassay) was carried out.

The cell stock frozen after each panning of the first to third round was added to a medium containing 5 ml of 2×YTCM (yeast extract 10 g, tryptone 17 g, NaCl 5 g, chloramphenicol 34 μg/ml), 2% glucose, and 5 mM magnesium chloride ($MgCl_2$) such that $OD_{600}$ is 0.1, and then cultured for 2 to 3 hours at 37° C. ($OD_{600}$=0.5 to 0.7). Then, after infection with M1 helper phage, culture for 16 hours at 30° C. in a medium containing 2×YTCMK (2×YTCM, kanamycin 35 μg/ml), 5 mM magnesium chloride and 1 mM IPTG was carried out. The cultured cells were centrifuged (4,500 rpm, 15 minutes, 4° C.) and the supernatant was transferred to a new tube. On a 96-well immuno-plate (#439454, NUNC, USA), each of the two human LAG-3 antigens, i.e., LAG-3-mFc and Lag-3-his protein, was coated in an amount of 100 ng per well at 4° C. for 16 hours using a coating buffer, and then each well was blocked by using 4% skim milk dissolved in PBS. After that, each well was washed with 0.2 ml of PBS-T, and the first- to third-panning poly scFv-phage was added to each well, each in an amount of 100 μl, followed by reaction for 2 hours at room temperature. Then again, each well was washed 4 times with 0.2 ml of PBS-T, and, after diluting HRP (horseradish peroxidase)-tagged mouse anti-M13 antibody (#11973-MM05, Sino Biological Inc.) at 1:2,000, the reaction with an antibody was carried out for 1 hour at room temperature. After washing with PBS-T, OPD tablet (Sigma, #8787-TAB) was prepared in PC buffer (0.1 M $Na_2HPO_4$, 0.005 M Na-Citrate, pH 5.0) to prepare a substrate solution and added to the well (100 μl per well) to have color development for 10 minutes. Then, the absorbance at 490 nm was measured by using a spectrophotometer (Molecular Device, USA).

As a result, according to FIG. 2, it was found by ELISA that the binding property for LAG-3-mFc and LAG-3-his protein, which are two human LAG-3 antigens having different carboxy-terminal tag, has been enriched in the third poly scFv-phage.

2-3. Selection of Monoclone

To select antigen-specific scFv phage monoclone, the colonies obtained from the third panning multiclone phage antibody group having high binding property (third panning) were cultured for 16 hours at 37° C. in a 96-deep well plate (#90030, Bioneer, Korea) by using 1 ml medium containing 2×YTCM, 2% glucose, and 5 mM magnesium chloride. After culture, 100 to 200 μl were collected and added to 1 ml medium containing 2×YTCM, 2% glucose, and 5 mM magnesium chloride such that $OD_{600}$ is 0.1, and cultured for 2 to 3 hours at 37° C. such that $OD_{600}$ is 0.5 to 0.7. Infection of M1 helper phage was carried out to have MOI (multiplicity of infection) value of 1:20, and then monoclonal scFv phage was subjected to phage-ELISA in the same manner as Example 2-2 described above.

Figure 3:
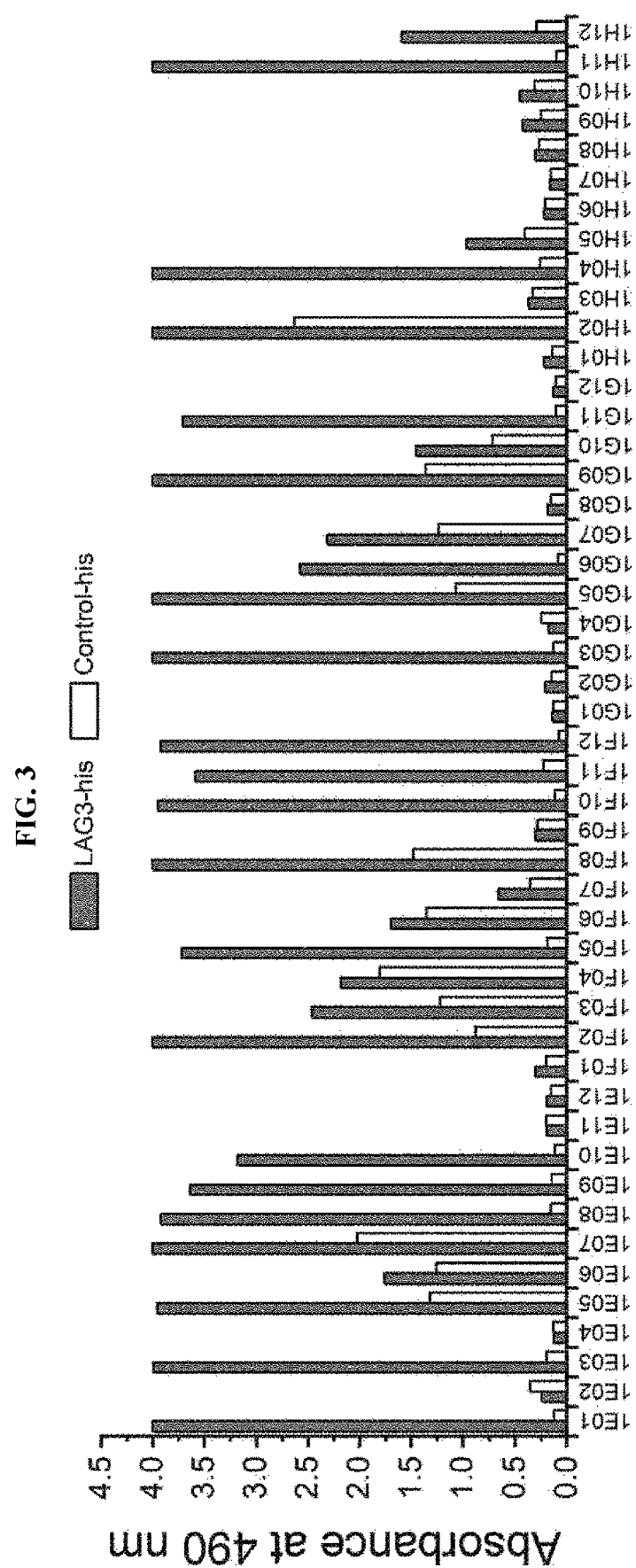
FIG. 3 shows the binding capacity of monoclonal scFv phage to LAG-3 protein.

As a result, as it is illustrated in FIG. 3, 28 monophage clones showing high binding property for the recombinant human LAG-3-his antigen were selectively obtained. The selected phage clones were further selected by the nucleotide sequencing of the following Example 2-4 and antibody property analysis of Examples 3 to 5. The following examples were made, among the selected clones, for monoclone 1E09 showing specific binding to LAG-3.

2-4. Nucleotide Sequencing of Monoclone

For the selected monoclone 1E09 showing specific binding to LAG-3, DNA-prep was carried out by using a kit for DNA purification (Qiagen, Germany) and Solgent, Korea was requested to carry out the sequencing of the DNA. In view of the sequencing result, CDR site of VH (variable region of heavy chain) and VL (variable region of light chain) of the selected antibody was determined. Then, the similarity between those antibodies and germ line antibody group was examined by using Ig BLAST program provided in NCBI webpage. As a result, properties of the monoclone 1E09 showing specific binding to LAG-3 are summarized in Table 3.

TABLE 3

| Characteristics of LAG-3 monoclone 1E09 | | | | | |
|---|---|---|---|---|---|
| Clone name | VH | Similarity | VL | Similarity | Group |
| 1E09 | VH3-11 | 88.8% | O12 | 89.5% | 1 |

The heavy chain and light chain CDR and FR (framework region) sequence of the selected antibody, and the antibody which includes the heavy chain variable region and light chain variable region containing them are described in the following Tables 4 and 5.

TABLE 4

Heavy chain variable region of LAG-3 monoclone 1E09

| Clone name | FR1 | CDR1 | FR2 | CDR2 | FR3 | CDR3 | FR4 |
|---|---|---|---|---|---|---|---|
| 1E09 | QVQLVQS GGDLVKP GGSLRLS CAAS (SEQ ID NO: 4) | GFSFSDH Y (SEQ ID NO: 1) | MNWIRQA PGKGLEW VAY (SEQ ID NO: 5) | IDTSATY I (SEQ ID NO: 2) | YYADSVK GRFTISR DNAKNSL YLQMNSL RAEDTAV YYC (SEQ ID NO: 6) | ARDNWGS LDY (SEQ ID NO: 3) | WGQGALV TVSS (SEQ ID NO: 7) |

TABLE 5

Light chain variable region of LAG-3 monoclone 1E09

| Clone name | FR1 | CDR1 | FR2 | CDR2 | FR3 | CDR3 | FR4 |
|---|---|---|---|---|---|---|---|
| 1E09 | DIQMTQSP SSLSPSVG DRVTITCQ | QEISIY (SEQ ID NO: 8) | LNWYQ QKPGK APKLLI | DAS | NLETGVP SRFSGSGS GTDFTLTI | QQTYIT PYT (SEQ ID | FGQGTK LDIK (SEQ ID |

TABLE 5-continued

Light chain variable region of LAG-3 monoclone 1E09

| Clone name | FR1 | CDR1 | FR2 | CDR2 | FR3 | CDR3 | FR4 |
|---|---|---|---|---|---|---|---|
| | AS (SEQ ID NO: 11) | | Y (SEQ ID NO: 12) | | SSLQPEDF ATYYC (SEQ ID NO: 13) | NO: 10) | NO: 14) |

Example 3. Production of Human Anti-LAG-3 Monoclonal Antibody

3-1. Conversion of scFv Form into IgG Form

To convert the selected monoclonal phage antibody for LAG-3 into full IgG form, each of the DNA sequence of heavy chain and light chain was subjected to PCR (iCycler iQ, BIO-RAD, USA) by using primers in which restriction enzyme sites for SfiI/NheI and SfiI/BglII are included, respectively. The heavy chain and light chain PCR products were digested together with each expression vector having a corresponding restriction enzyme site, and the DNA was eluted using DNA-gel extraction kit (Qiagen). For ligation, vector (1 μl, 10 ng), heavy chain or light chain (100 to 200 ng, 15 μl), 10× buffer (2 μl), ligase (1 U/μl, 1 μl), and distilled water were admixed with one another, kept for 1 to 2 hours at room temperature, and added to cells for transformation (competent cell, XL1-blue). The resultant was kept on ice for 5 minutes, and then applied with heat shock at 42° C. for 90 seconds.

After the heat shock, the cells were added with 1 ml of medium and cultured for 1 hour at 37° C. followed by spreading on an LB Amp plate and culture for 16 hours at 37° C. Thus-obtained colonies were collected and inoculated with 5 ml of an LB Amp medium. After culture for 16 hours at 37° C., DNA-prep was carried out by using DNA-prep kit (Nuclogen). Sequencing of the thus-obtained DNA was requested (Solgent, Korea).

As a result, it was found that the DNA sequence of the heavy chain and light chain clones of 1E09, which have been converted into full IgG, corresponds to the sequence of phage antibody of the clone of Table 3. After that, to produce the 1E09 antibody, each of the heavy chain and light chain clones was cultured in 100 ml medium of LB Amp, and a large amount of plasmid was obtained by using midi-prep kit (QIAgen).

3-2. Production of Human Monoclonal Antibody

The prepared expression vector including heavy chain and light chain was subjected to co-transfection in HEK-293F cells at a ratio of 6:4. Seven days after the co-transfection, the supernatant was collected and the cells and floating materials were removed by centrifuge and a 0.22 μm Top-filter. The supernatant was collected and subjected to protein A affinity chromatography to purify the IgG antibody. After the purification, the antibody was eluted using glycine buffer, and buffer exchange was made with the final PBS buffer. The purified antibody was quantified based on absorbance at 280 nm by spectrophotometer (SpectraMX M5, Molecular Devices, USA) using molar extinction coefficient of the antibody, and then stored at −70° C. until use. The antibody was then subjected to SDS-PAGE analysis with a load of 5 μg for each of reducing condition and non-reducing condition. Accordingly, the purity and mobility state of the purified protein were determined.

Figure 4:
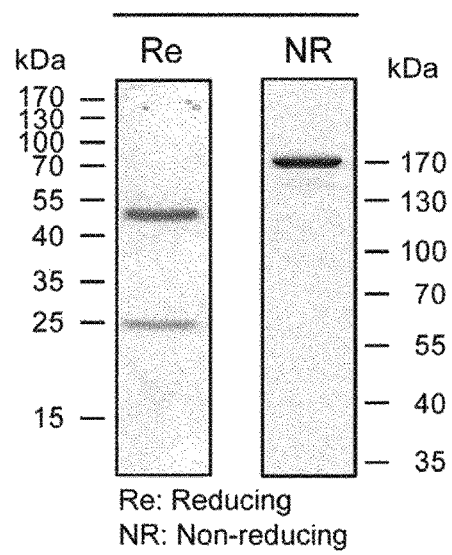
FIG. 4 shows the result of analyzing the antibody purity of 1E09, which is a purified anti-LAG-3 antibody, by SDS-PAGE at reducing or non-reducing conditions.

As a result, human anti-LAG-3 monoclonal antibody 1E09 was detected at a size of at least 150 kDa under non-reducing condition, and the yield was 130 mg/L (FIG. 4).

Example 4. Property of Human Anti-LAG-3 Monoclonal Antibody

4-1. Antibody Specificity for LAG-3 Antigen

For having a transformed cell pool in which human LAG-3 is overexpressed, HEK293E was transfected with pcDNA3.1 plasmid containing human LAG-3 (NCBI accession number NM 002286.5), and then a selection process was carried out with a selection medium containing 100 μg/ml Zeocin (#R25001, Thermo Fisher Scientific). After the selection process, the cell pool was separated by determining the expression state by FACS (fluorescence activated cell sorting) analysis using human anti-LAG-3 antibody (#565616, BD, USA) linked with PE (phycoerythrin) fluorescent, and used for evaluating the characteristics of antibody for an antigen.

For determining the antigen specificity of LAG-3-1E09 antibody, the prepared HEK293E cell pool overexpressing human LAG-3 was treated with LAG-3 siRNA (small interfering RNA) (Bioneer, Korea) to reduce the LAG-3 expression, and the antibody binding level was compared, via FACS analysis, with the binding level before the reduction.

Figure 5A:
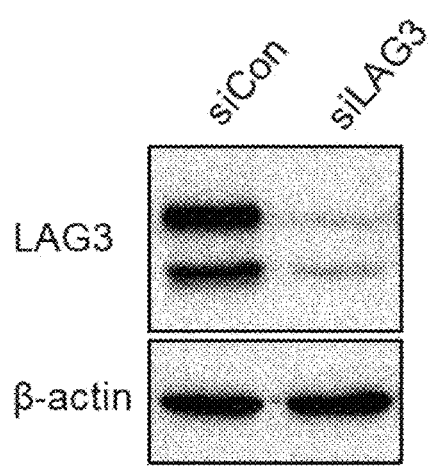
FIG. 5 shows the result of determining the binding specificity of 1E09 for antigen using HEK293E cell lines with different expression level of LAG-3 protein.
Figure 5B:
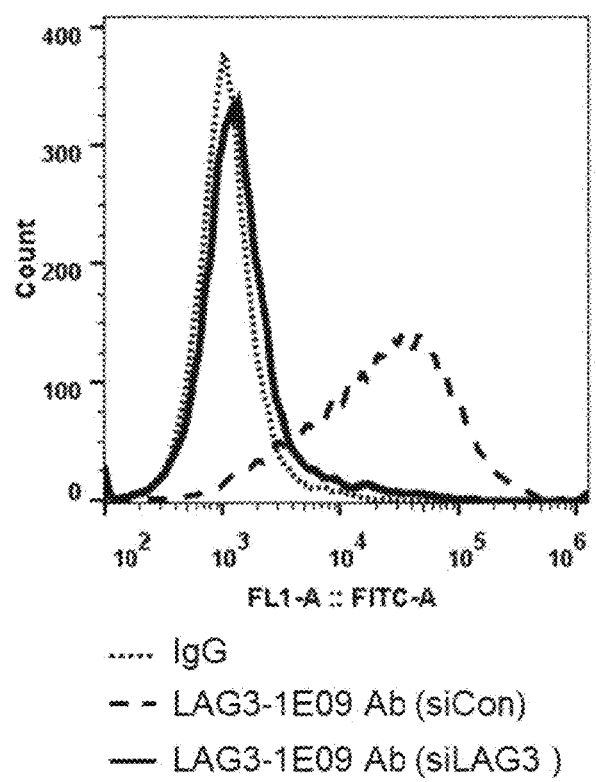

As a result of treating the cells overexpressing human LAG-3 with control siRNA (siCon) or LAG-3 siRNA (siLAG-3) at 20 nM concentration followed by Western blotting 48 hours thereafter, it was shown that the expression amount of LAG-3 has decreased by more than 90% in the cells which have been treated with LAG-3 siRNA (siLAG-3) (A of FIG. 5). At that time, to determine the cell binding of anti-LAG-3 antibody, each cell was prepared (0.5×10$^6$ cells per sample) and reacted with the antibody (2 μg/ml) for 30 minutes at 4° C. After that, the cells were washed three times with PBS containing 2% FBS and then subjected to the reaction for 30 minutes at 4° C. with anti-human IgG antibody (#FI-3000, Vectorlabs) linked with FITC (fluorescein isothiocyanate) fluorescent. The cells were washed by the same washing process as above followed by suspension in 0.2 ml PBS containing 2% FBS. The cells were then analyzed by FACSCanto II flow cytometer. As a result, it was found that human LAG-3-1E09 monoclonal antibody binds well to the human LAG-3-overexpressing cells while showing less binding to the cells with reduced LAG-3 expression due to the treatment with LAG-3 siRNA (B of FIG. 5). This result indicates that human LAG-3-1E09 monoclonal antibody specifically binds to the human LAG-3 antigen.

4-2. Determination of Cross-Reactivity to LAG-3 of Other Species

By transfecting HEK293E cells with pcDNA3.1 plasmid containing monkey (Rhesus monkey) LAG-3 (NCBI accession number XM_001108923.2) or mouse LAG-3 (NCBI accession number NM_008479) in the same manner as the preparation a pool of the transfected cells overexpressing human LAG-3 of Example 4-1, a cell pool was prepared and used for evaluation of the characteristics of 1E09 antibody for an antigen.

In order to determine the cross-reactivity of the human LAG-3-1E09 monoclonal antibody, transfected HEK293E cells overexpressing human, monkey, or mouse LAG-3 were prepared (0.2×10$^6$ cells per sample), and, after carrying out 1/3 serial dilution of the antibody starting from 6 μg/ml (40 nM), the cells were reacted with the antibody for 30 minutes at 4° C. After that, the cells were washed three times with PBS containing 2% FBS and then subjected to the reaction for 30 minutes at 4° C. with anti-human IgG antibody (#FI-3000, Vectorlabs) linked with FITC fluorescent. The cells were washed by the same washing process as above followed by suspension in 0.2 ml PBS containing 2% FBS. The cells were then analyzed by FACSCanto II flow cytometer.

Figure 6:
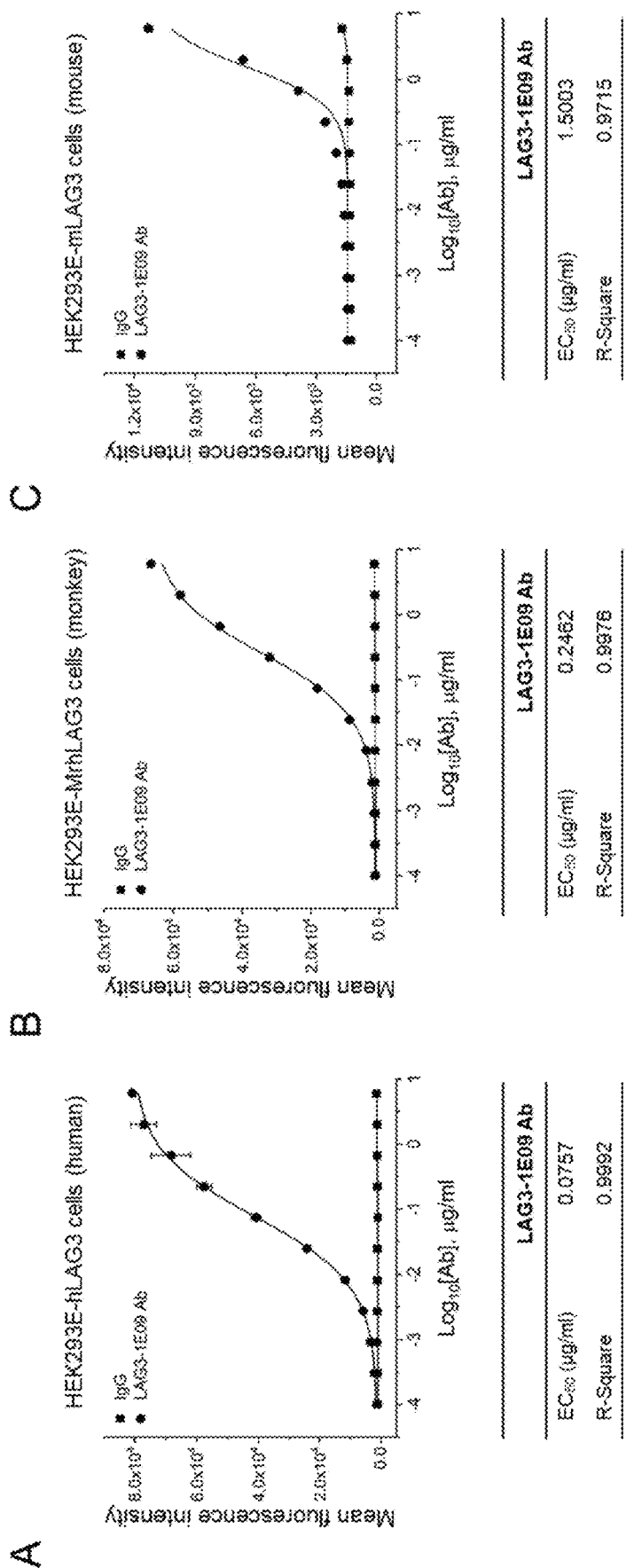
FIG. 6 shows the result of determining the cross-reactivity and binding specificity of 1E09 antibody by using cells in which human LAG-3 (A), monkey LAG-3 (B) or mouse LAG-3 (C) is overexpressed.

As a result, it was found that human LAG-3-1E09 monoclonal antibody binds specifically to any one of human, monkey and mouse LAG-3 protein which has been overexpressed on cell surface and the binding increases in the antibody concentration dependent manner (FIG. 6). At that time, when the cell binding capacity of antibody is estimated in terms of the amount required for having 50% of the maximum binding (i.e., EC$_{50}$), as a result of analyzing the MFI (mean fluorescence intensity) values representing the level of binding to cells by using GraphPad Prism software, EC$_{50}$ value representing the cell binding capacity of LAG-3-1E09 antibody was calculated to be 0.0757 μg/ml for human LAG-3, 0.2462 μg/ml for monkey LAG-3, and 1.5003 μg/ml for mouse LAG-3.

4-3. Determination of Affinity of Human Anti-LAG-3 Monoclonal Antibody for Antigen The binding affinity of human anti-LAG-3 monoclonal antibody 1E09 for an antigen was measured with antigen OCTET® QK$^e$ (Fortebio Inc. USA) analyzer by using human LAG-3 (hLAG-3-mFc), monkey LAG-3 (MrhLAG-3-mFc), or mouse LAG-3 (mLAG-Fc), which are recombinant fusion proteins fused with mouse Fc (mFc) at the carboxy terminal.

To measure the antigen-antibody affinity, AHC (anti-human Fc capture: #18-5060, Fortebio Inc.) or AMC (anti-mouse Fc capture: #18-5088, Fortebio Inc.) biosensor was first stabilized in buffer (#18-1042, Fortebio Inc.) for 10 minutes and immobilized with the antigen or antibody. After stabilization for 10 minutes in a buffer (#18-1042, Fortebio Inc.), immobilized antigen or antibody was washed out for 5 minutes with the buffer. The antibody or antigen desired for binding was prepared at different concentrations (0.94-60 nM) in a 96-well plate (#655209, Greiner Bio-One, USA) and subjected to the association reaction for 10 minutes followed by dissociation reaction for 10 minutes or 30 minutes. All tests were carried out at conditions of 30° C., 1,000 rpm, and, by collecting the sensorgram data during the association and dissociation processes over time and applying 1:1 global binding fitting model according to Octet Data Analysis Software 9.0, equilibrium dissociation constant (K$_D$) was obtained.

Figure 7A:
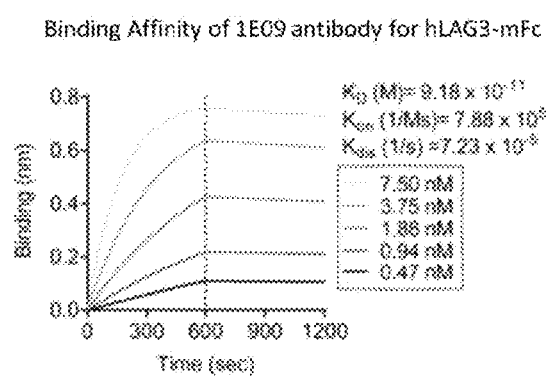
FIG. 7 shows the result of measuring the binding affinity of 1E09 antibody for human, monkey or mouse LAG-3 protein and kinetic constant of the binding, in which the measurement was carried out by using the octet system.
Figure 7B:
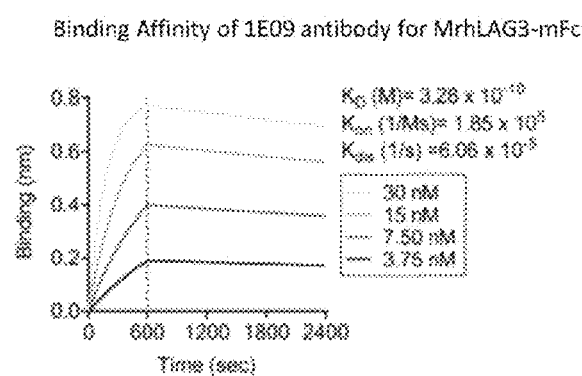
Figure 7C:
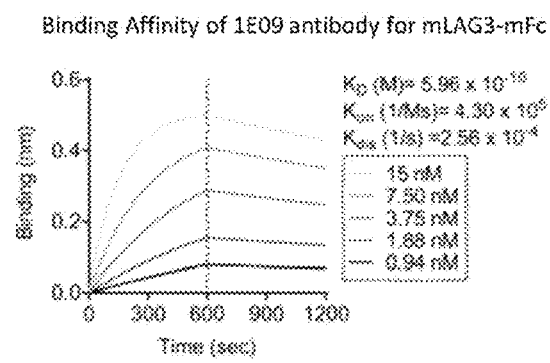

As a result, as shown in FIG. 7, the antigen binding capacity (K$_D$) of human anti-LAG-3 monoclonal antibody 1E09 was highest for human LAG-3 antigen, i.e., 0.0918 nM (A of FIG. 7), while showing the affinity of 0.328 nM for monkey LAG-3 antigen (B of FIG. 7) and 0.596 nM for mouse LAG-3 antigen (C of FIG. 7).

4-4. Determination of Epitope to LAG-3 Antigen by ELISA Analysis

To determine the antigen binding site of human anti-LAG-3 monoclonal antibody 1E09, as shown in A of FIG. 8, a variant (M1 to M7) in which Ig-V domain (29th-167th amino acid sequence) in the extracellular domain of LAG-3 has been cleaved or a specific or non-specific amino acid in the Ig-V domain is substituted with other amino acid and the wild-type (WT) were fused with mFc or His tag to prepare recombinant LAG-3 protein in the same manner as above Example 1 followed by purification (A and B of FIG. 8). Meanwhile, LAG-3-His (WT) was purchased from Sino Biological Inc. (#16498-H08H) and the recombinant LAG-3-His proteins prepared as above were first purified by affinity chromatography using Ni Sepharose 6 Fast Flow resin (#17531803, GE Healthcare). The purified or purchased recombinant LAG-3 proteins were first subjected to purity determination by SDS-PAGE (B of FIG. 8), and then used for ELISA analysis to determine the binding specificity of human anti-LAG-3 monoclonal antibody 1E09 (C of FIG. 8).

As a result of the ELISA analysis using LAG-3 antigen variant, it was found that, compared to the wild-type LAG-3 antigen, LAG-3-1E09 antibody does not bind to the LAG-3-ΔIg-V variant and, in case of LAG-3 Ig-V domain variant, the binding decreases in order of M7>M6≥M4>M1 (C of FIG. 8). Based on this result, it was shown that human LAG-3-1E09 monoclonal antibody has a binding site in Ig-V domain (29th-167th amino acids sequence) among the extracellular domains of LAG-3. Specifically, it has a binding site in the variable amino acid sites of M1, M4, M6, M7 variant of LAG-3 Ig-V domain. As those amino acid sites are found to be $^{52}$DL$^{53}$, $^{107}$GGLRSGRLPLQ$^{117}$ (SEQ ID NO: 9), $^{137}$R, and $^{150}$AVHLRDRALSCR$^{161}$ (SEQ ID NO: 31), respectively, in the wild-type LAG-3, it is recognized that LAG-3-1E09 antibody of the present invention has a conformational epitope.

Example 5. Evaluation of Activity of Human Anti-LAG-3 Monoclonal Antibody 5-1. Determination of Inhibition of Forming of LAG-3/MHC Class II Complex by Anti-LAG-3 Antibody To see whether or not LAG-3-1E09 antibody can inhibit the forming of LAG-3/MHC class II complex, Raji cell line (human leukemia cells derived from Burkitt lymphoma) expressing MHC class II on cell surface was prepared in an amount of 0.2×10$^6$ cells per sample. The antibodies were serially diluted (×1/2 dilution starting from 400 nM) in 200 nM (14.4 μg/ml) LAG-3-mFc protein and reacted for 30 minutes at 4° C. for 30 minutes (pre-incubation). After that, the antigen-antibody mixture was reacted with the prepared cells for 30 minutes at 4° C. The cells were then washed 3 times with PBS containing 2% FBS, and then reacted for 30 minutes at 4° C. with anti-mouse IgG antibody (#FI-2000, Vectorlabs) which has been linked to FITC fluorescent for detecting LAG-3-mFc. After washing them in the same manner as above and suspending them in 0.2 ml PBS containing 2% FBS, analysis was made using CytoFLEX flow cytometer (Beckman coulter, USA)

Figure 9:
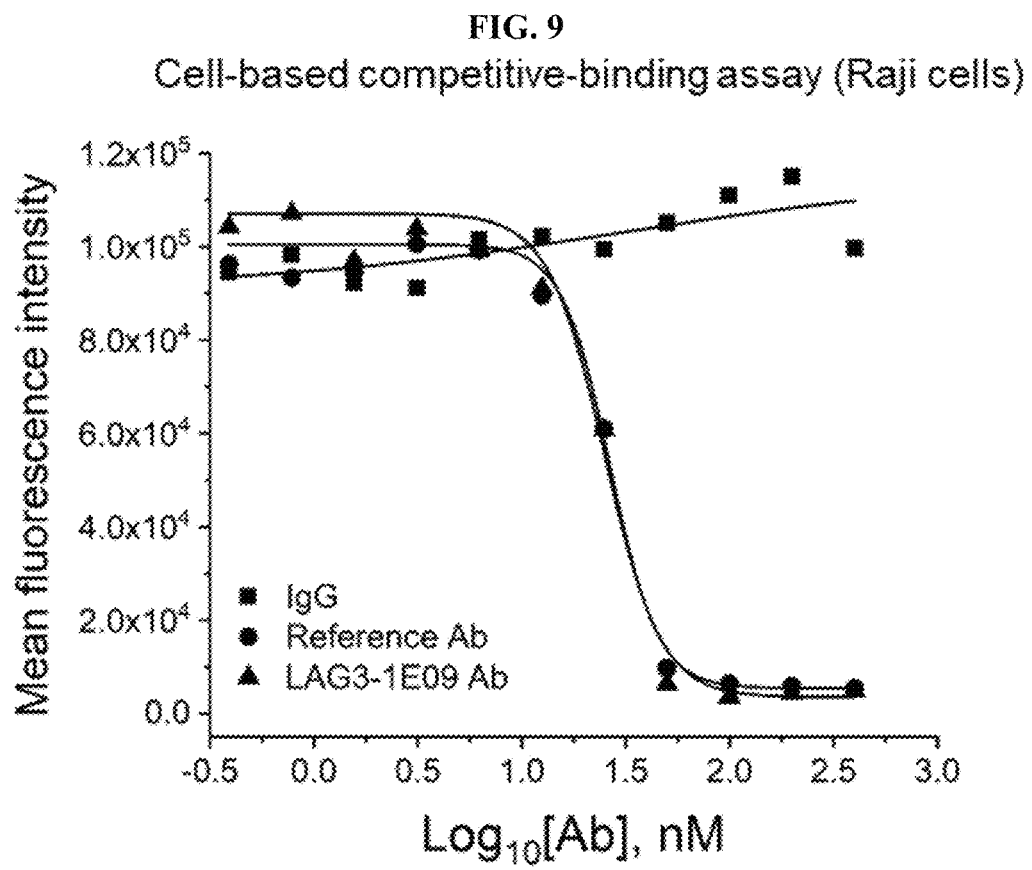
FIG. 9 shows the result of determining the effect of 1E09 for inhibiting the forming of LAG-3/MHC class II complex in concentration dependent manner, in which the determination was made by using Raji cells expressing recombinant human LAG-3 protein (hLAG-3-mFc) and MHC class II.

Property of LAG-3-1E09 antibody to inhibit the forming of LAG-3/MHC class II complex can be determined by a decrease in the binding capacity of LAG-3-mFc which binds to cells expressing MHC class II, and, according to the test result, it was found that human anti-LAG-3 monoclonal antibody 1E09 including the control antibody (see, Korean Patent Application Publication No. 2015-0023909) inhibits the forming of a complex between LAG-3 and MHC class II in a concentration dependent manner (FIG. 9). The inhibition degree can be expressed in terms of the amount of sample that is required to have 50% of the maximum inhibition caused by the antibody (i.e., $IC_{50}$). As a result of carrying an analysis using the MFI values showing the inhibition degree of LAG-3-mFc and GraphPad Prism software, it was found that $IC_{50}$ value is similar between the control antibody (i.e., reference) and 1E09 antibody, i.e., 26.6084 nM and 25.0922 nM, respectively.

5-2. Evaluation of Activity of LAG-3-1E09 Antibody for T Cells

The test for evaluating the activity of human monoclonal antibody 1E09 binding to LAG-3 was carried out by using LAG-3/MHC class II blockade bioassay kit (#CS194822, Promega). After culturing APC cell line, in which MHC class II is overexpressed, for at least 16 hours in a 96-well plate, it was treated with each antibody which has been prepared by ×1/2.5 serial dilution starting from 10 μg/ml antibody concentration, and then co-cultured for 6 hours with acting cell line overexpressing human LAG-3 (i.e., Jurkat T line). Inhibition recovery level by the antibody can be followed by the luminescence intensity resulting from degradation of a substrate by luciferase, and the measurement was carried out using a spectrophotometer (GLO-MAX® Discover System, Model #GM3000, Promega). Including the control antibody (i.e., reference), LAG-3-1E09 antibody showed the activity of recovering, in a concentration dependent manner, the signal of Jurkat T cells which are an acting cell line but have been reduced due to forming of LAG-3/MHC II complex (FIG. 10). The recovery level can be estimated in terms of the amount of a sample required for having 50% of the maximum effect by the antibody (i.e., $EC_{50}$). As a result of analyzing the result by using GraphPad Prism software, $EC_{50}$ value representing the capacity of recovering the inhibition was 0.05784 μg/ml for LAG-3-1E09 antibody and 0.16811 μg/ml for the control antibody (i.e., reference), showing that 1E09 antibody of the present invention has better activity, i.e., about 2.9 times than the control antibody.

Example 6. Optimization of Human Anti-LAG-3 Monoclonal Antibody 6-1. Construction of Libraries for Optimization of 1E09 Antibody The antibody optimization was conducted by, after constructing new LC shuffling libraries by introducing a $10^5$-$10^6$ light chain (LC) pool owned by Y-Biologics Inc. while holding the heavy chains, 1) LC shuffling, 2) core packing+LC shuffling including comparatively analyzing with the residues of structurally important sites such as hydrophobic cores, exposed residues, charge clusters and salt bridges of heavy chains, performing mutations with conserved residues, and conducting LC shuffling, and 3) CDR hot spot+LC shuffling including, for the DNA in variable region of the antibody, randomly mutating mutational hot spots that can be mutated frequently in the process of in vivo affinity maturation and conducting LC shuffling.

For the construction of LC shuffling libraries, the LC gene of 1E09 antibody was cleaved with BstX I and then used as a vector, and the library pool owned by Y-biologics Inc. was cleaved with BstX I and used as an insert. After ligation with ligase, transformation was performed using the cells for electroporation transformation. The transformed cells were collected in a square plate to prepare antibody libraries, and about $1.5 \times 10^7$ various libraries were obtained accordingly.

The result of sequencing showed that all heavy chain (HC) sequences were identical to each other while the LC sequences were different from each other.

For the construction of the core packing+LC shuffling libraries, the FR portion of the 1E09 antibody was substituted with a conserved amino acid sequence, the LC gene was cleaved with BstX I and then used as a vector, and a library pool owned by Y-biologics Inc. was cleaved with BstX I and then used as an insert. After ligation with ligase, transformation was performed using the cells for electroporation transformation. The transformed cells were collected in a square plate to prepare antibody libraries, and about $8.4 \times 10^6$ various libraries were obtained. The result of sequencing showed that the FR portion of HC was substituted with conserved amino acid sequences while the LC sequences were different from each other.

For the construction of CDR hot spot+LC shuffling libraries, the FR portion of the 1E09 antibody was substituted with a conserved amino acid sequence, the hot spot library of CDR1, CDR2 was cleaved with Sfi I and then used as an insert, and a library pool owned by Y-biologics Inc. was cleaved with Sfi I and then used as a vector. After ligation with ligase, transformation was performed using the cells for electroporation transformation. The transformed cells were collected in a square plate to prepare antibody libraries, and about $5.6 \times 10^6$ various libraries were obtained. The result of sequencing showed that the FR portion of HC was substituted with conserved amino acid sequence, and the amino acid of the hot spot sequence of CDR1, CDR2 was randomly mutated while LC sequences were different from each other.

Example 7. Screening of Human Anti-LAG-3 Monoclonal Antibody Variants 7-1. Biopanning Biopanning for screening the variants of 1E09 antibody was carried out in the same manner as Example 2-1 after infecting bacteria with the human antibody libraries which have been produced in Example 6-1 for antibody optimization. scFv-phages capable of specifically binding to LAG-3 protein were eluted. Through a panning process in which *Escherichia coli* are infected again with the eluted phages for amplification, a pool of positive phages was obtained and panning for obtaining the antibody variant was performed in the first round only. As a result, number of input phages and number of binding to antigen were determined for the panning in which optimized human antibody libraries have been used, as the results are shown in Table 6.

TABLE 6

Comparison of antibody titer according to panning method for antibody optimization

| Sample | Number of input phages | Number of bound phages |
|---|---|---|
| 1E09 (LC shuffling, LS) | $8.0 \times 10^{12}$ | $3.2 \times 10^8$ |
| 1E09 (Core packing + LS) | $1.2 \times 10^{13}$ | $1.1 \times 10^8$ |
| 1E09 (CDR hot spot + LS) | $2.0 \times 10^{12}$ | $3.4 \times 10^8$ |
| 1E09 (Core packing + CDR hot spot + LS) | $4.0 \times 10^{12}$ | $8.0 \times 10^7$ |

7-2. Screening of Monoclones of Anti-LAG-3 Antibody Variants

Phage-ELISA was carried out for monoclonal scFv phage by subjecting the colonies obtained from panning using the optimized human antibody libraries, which have been prepared to screen a monoclonal scFv phage specific to the LAG-3 antigen, in the same manner as the method of Example 2-3.

Figure 11A:
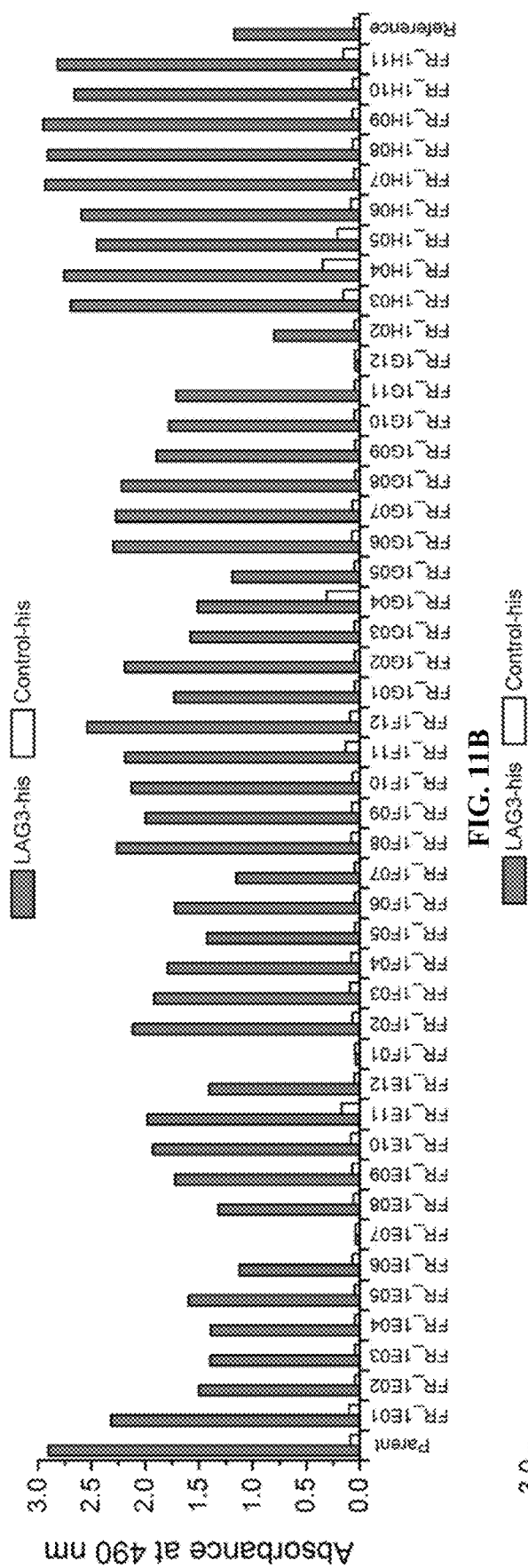
FIG. 11 shows the binding capacity of monoclonal scFv phage of 1E09 antibody variants to LAG-3.
Figure 11B:
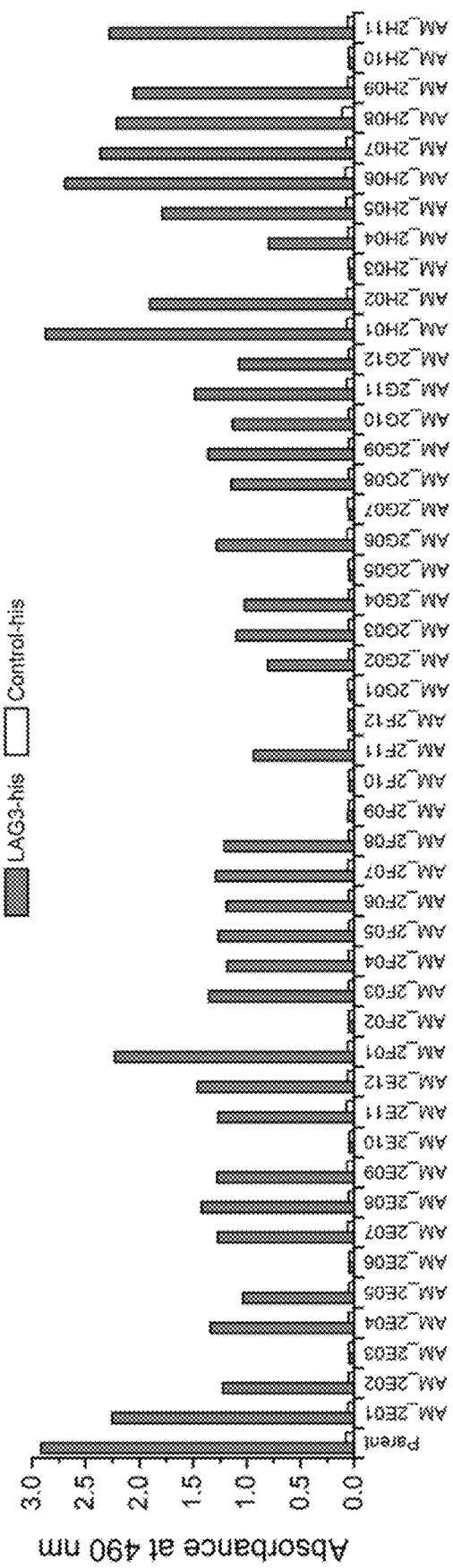

As a result, among the results of panning using the 1E09 optimized human antibody libraries, e.g., 132 clones that are obtained from the methods of Core packing+LC shuffling (A of FIG. 11) and Core packing+CDR hot spot+LC shuffling (B of FIG. 11), 78 monophage clones including a clone having antigen binding capacity similar to the parent antibody (1E09) were identified.

7-3. Nucleotide Sequencing of Anti-LAG-3 Antibody Variants

Nucleotide sequencing was carried out for the screened monoclones in the same manner as Example 2-4. As a result, 22 new phage antibodies showing a difference in similarity to the parent antibody 1E09 were identified and summarized in Table 7.

TABLE 7

Characteristics of monoclones of human anti-LAG-3 antibody variants that are selected by optimization process

| Clone name | VH | Similarity | VL | Similarity2 | Group |
|---|---|---|---|---|---|
| LAG3-1E09_LS_1A10 | VH3-11 | 88.80% | O12 | 100% | 1 |
| LAG3-1E09_LS_1E06 | VH3-11 | 88.80% | O12 | 90.50% | 2 |
| LAG3-1E09_LS_1G11 | VH3-11 | 85.70% | O12 | 91.60% | 3 |

TABLE 7-continued

Characteristics of monoclones of human anti-LAG-3 antibody variants that are selected by optimization process

| Clone name | VH | Similarity | VL | Similarity2 | Group |
|---|---|---|---|---|---|
| LAG3-1E09_LS_1H04 | VH3-11 | 88.80% | O18 | 92.60% | 4 |
| LAG3-1E09_FR_1A06 | VH3-11 | 88.80% | A27 | 85.40% | 5 |
| LAG3-1E09_FR_1A10 | VH3-11 | 89.80% | O18 | 88.40% | 6 |
| LAG3-1E09_FR_1E05 | VH3-11 | 87.80% | O18 | 88.40% | 7 |
| LAG3-1E09_FR_1E09 | VH3-11 | 89.80% | O18 | 92.60% | 8 |
| LAG3-1E09_FR_1E10 | VH3-11 | 88.80% | O18 | 91.60% | 9 |
| LAG3-1E09_FR_1F03 | VH3-11 | 89.80% | O18 | 94.70% | 10 |
| LAG3-1E09_FR_1G07 | VH3-11 | 88.80% | O12 | 89.50% | 11 |
| LAG3-1E09_CDR_1D04 | VH3-11 | 88.80% | O18 | 96.70% | 12 |
| LAG3-1E09_CDR_1E03 | VH3-11 | 87.80% | O18 | 88.40% | 13 |
| LAG3-1E09_AM_1B03 | VH3-11 | 86.70% | O18 | 94.70% | 14 |
| LAG3-1E09_AM_1E09 | VH3-11 | 88.80% | L6 | 90.00% | 15 |
| LAG3-1E09_AM_1F09 | VH3-11 | 88.80% | O12 | 88.40% | 16 |
| LAG3-1E09_AM_1H07 | VH3-11 | 85.70% | O12 | 92.60% | 17 |
| LAG3-1E09_AM_2E04 | VH3-11 | 86.70% | O12 | 93.70% | 18 |
| LAG3-1E09_AM_2E09 | VH3-11 | 86.70% | O18 | 84.20% | 19 |
| LAG3-1E09_AM_2G11 | VH3-11 | 86.70% | O12 | 91.60% | 20 |
| LAG3-1E09_AM_2H01 | VH3-11 | 87.80% | O12 | 87.40% | 21 |
| LAG3-1E09_AM_2H06 | VH3-11 | 87.80% | O18 | 96.70% | 22 |

Heavy chain and light chain CDR and FR sequence of the selected antibodies, and antibody including heavy chain variable region and light chain variable region containing them are as shown in the following Table 8 to Table 13.

TABLE 8

Heavy chain variable region of selected human LAG3 antibody variants

| NAME | FR1 | CDR1 | FR2 | CDR2 | FR3 | CDR3 | FR4 |
|---|---|---|---|---|---|---|---|
| LAG3-1E09_LS_1A10 | EVQLVES GGDLVKP GGSLRLSC AAS (SEQ ID NO: 15) | GFSFSDH Y (SEQ ID NO: 1) | MNWIRQ APGKGL EWVAY (SEQ ID NO: 5) | IDTSATY I (SEQ ID NO: 2) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |
| LAG3-1E09_LS_1E06 | EVQLVES GGDLVKP GGSLRLSC AAS (SEQ ID NO: 15) | GFSFSDH Y (SEQ ID NO: 1) | MNWIRQ APGKGL EWVAY (SEQ ID NO: 5) | IDTSATY I (SEQ ID NO: 2) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |
| LAG3-1E09_LS_1G11 | EVQLVES GGDLVQP GGSLRLSC AAS (SEQ ID NO: 17) | GFNFSDH Y (SEQ ID NO: 18) | MNWVR QAPGKG LEWVA Y (SEQ ID NO: 19) | IDTTAT YI (SEQ ID NO: 20) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |
| LAG3-1E09_LS_1H04 | EVQLVES GGDLVKP GGSLRLSC AAS (SEQ ID NO: 15) | GFSFSDH Y (SEQ ID NO: 1) | MNWIRQ APGKGL EWVAY (SEQ ID NO: 5) | IDTSATY I (SEQ ID NO: 2) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |
| LAG3-1E09_FR_1A06 | EVQLVES GGGLVKP GGSLRLSC AAS (SEQ ID NO: 21) | GFSFSDH Y (SEQ ID NO: 1) | MNWVR QAPGKG LEWVA Y (SEQ ID NO: 19) | IDTSATY I (SEQ ID NO: 2) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |

TABLE 8-continued

Heavy chain variable region of selected human LAG3 antibody variants

| NAME | FR1 | CDR1 | FR2 | CDR2 | FR3 | CDR3 | FR4 |
|---|---|---|---|---|---|---|---|
| LAG3-1E09_FR_1A10 | EVQLVESGGGLVKPGGSLRLSCAAS (SEQ ID NO: 21) | GFSFSDHY (SEQ ID NO: 1) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_FR_1E05 | EVQLVESGGGLVQPGGSLRLSCAAS (SEQ ID NO: 22) | GFSFSDHY (SEQ ID NO: 1) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_FR_1E09 | EVQLVESGGGLVKPGGSLRLSCAAS (SEQ ID NO: 21) | GFSFSDHY (SEQ ID NO: 1) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |

TABLE 9

Heavy chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_FR_1E10 | EVQLVESGGGLVKPGGSLRLSCAAS (SEQ ID NO: 21) | GFSFSDHY (SEQ ID NO: 1) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_FR_1F03 | EVQLVESGGGLVKPGGSLRLSCAAS (SEQ ID NO: 21) | GFSFSDHY (SEQ ID NO: 1) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_FR_1G07 | EVQLVESGGGLVKPGGSLRLSCAAS (SEQ ID NO: 21) | GFSFSDHY (SEQ ID NO: 1) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_CDR_1D04 | EVQLVESGGDLVKPGGSLRLSCAAS (SEQ ID NO: 15) | GFSFSDHY (SEQ ID NO: 1) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_CDR_1E03 | EVQLVESGGDLVKPGGSLRLSCAAS (SEQ ID NO: 15) | GFTFNDHY (SEQ ID NO: 23) | MNWIRQAPGKGLEWVAY (SEQ ID NO: 5) | IDTTATYI (SEQ ID NO: 20) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |

TABLE 9-continued

Heavy chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_AM_1B03 | EVQLVESGGDLVQPGGSLRLSCAAS (SEQ ID NO: 17) | GFSFNDHY (SEQ ID NO: 24) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_1E09 | EVQLVESGGDLVKPGGSLRLSCAAS (SEQ ID NO: 15) | GFSFSDHY (SEQ ID NO: 1) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_1F09 | EVQLVESGGDLVKPGGSLRLSCAAS (SEQ ID NO: 15) | GFNFSDHY (SEQ ID NO: 18) | MNWIRQAPGKGLEWVAY (SEQ ID NO: 5) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |

TABLE 10

Heavy chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_AM_1H07 | EVQLVESGGDLVQPGGSLRLSCAAS (SEQ ID NO: 17) | GFSFNDHY (SEQ ID NO: 24) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_2E04 | EVQLVESGGDLVKPGGSLRLSCAAS (SEQ ID NO: 15) | GFSFNDHY (SEQ ID NO: 24) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_2E09 | EVQLVESGGDLVKPGGSLRLSCAAS (SEQ ID NO: 15) | GFSFSDHY (SEQ ID NO: 1) | MNWVRQAPGKGLEWVAY (SEQ ID NO: 19) | IDTNATYI (SEQ ID NO: 25) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_2G11 | EVQLVESGGDLVKPGGSLRLSCAAS (SEQ ID NO: 15) | GFSFTDHY (SEQ ID NO: 26) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |
| LAG3-1E09_AM_2H01 | EVQLVESGGDLVQPGGSLRLSCAAS (SEQ ID NO: 17) | GFTFSDHY (SEQ ID NO: 27) | MNWVRQAPGKGLEWVAY (SEQ ID NO: 19) | IDTSATYI (SEQ ID NO: 2) | YYADSVKGRFTISRDNAKNSLYLQMNSLRAEDTAVYYC (SEQ ID NO: 6) | ARDNWGSLDY (SEQ ID NO: 3) | WGQGTLVTVSS (SEQ ID NO: 16) |

TABLE 10-continued

Heavy chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_AM_2H06 | EVQLVES GGDLVKP GGSLRLSC AAS (SEQ ID NO: 15) | GFTFSDH Y (SEQ ID NO: 27) | MNWVRQ APGKGLE WVAY (SEQ ID NO: 19) | IDTIAT YI (SEQ ID NO: 28) | YYADSVKG RFTISRDNA KNSLYLQM NSLRAEDT AVYYC (SEQ ID NO: 6) | ARDNWG SLDY (SEQ ID NO: 3) | WGQGTLV TVSS (SEQ ID NO: 16) |

TABLE 11

Light chain variable region of selected human LAG3 antibody variants

| NAME | FR1 | CDR1 | FR2 | CDR2 | FR3 | CDR3 | FR4 |
|---|---|---|---|---|---|---|---|
| LAG3-1E09_LS_1A10 | DIQMTQSP SSLSASVG DRVTITCR AS (SEQ ID NO: 29) | QSISSY (SEQ ID NO: 30) | LNWYQQ KPGKAPK LLIY (SEQ ID NO: 12) | AAS | SLQSGVPSR FSGSGSGTD FTLTISSLQP EDFATYYC (SEQ ID NO: 32) | QQSYSTP YT (SEQ ID NO: 33) | FGQGTKLE IK (SEQ ID NO: 34) |
| LAG3-1E09_LS_1E06 | DIQMTQSP SSLSASVG DRVTITCQ AS (SEQ ID NO: 35) | QDISHY (SEQ ID NO: 36) | LNWYRQ KPGKAPK LLIY (SEQ ID NO: 37) | DAS | NLETGVPS RFSGSGSGT LFTLTISSL QPEDFATY YC (SEQ ID NO: 38) | QQSYSTP YT (SEQ ID NO: 33) | FGQGTKLE IK (SEQ ID NO: 34) |
| LAG3-1E09_LS_1G11 | DIQMTQSP SSLSASVG DRVTITCQ AS (SEQ ID NO: 35) | QDIDKY (SEQ ID NO: 39) | LNWYQQ KPGKAPK LLIY (SEQ ID NO: 12) | DAS | NLETGVPS RFSGSGSGT DFTLTISSL QPEDFATY YC (SEQ ID NO: 13) | QQSYSTP NT (SEQ ID NO: 40) | FGQGTKL DIK (SEQ ID NO: 14) |
| LAG3-1E09_LS_1H04 | DIQMTQSP SSLSASAG DRVTITCQ AS (SEQ ID NO: 41) | QDIRNS (SEQ ID NO: 42) | LSWYQQ KPGKAPK LLIY (SEQ ID NO: 43) | DAS | NLETGVPS RFSGSGSGT YFTFTISSL QPEDFATY YC (SEQ ID NO: 44) | QQYDNV PVT (SEQ ID NO: 45) | FGGGTKLE IK (SEQ ID NO: 46) |
| LAG3-1E09_FR_1A06 | DIQMTQSP GTLSMSPG EKATLSCR AS (SEQ ID NO: 47) | QTVTTN (SEQ ID NO: 48) | LAWYQQ KSGQAPR LLIY (SEQ ID NO: 49) | DAS | TRATGVPD RFSGSGSGT DFTLTISRL EPEDFAVY YC (SEQ ID NO: 50) | QQYGSSP YT (SEQ ID NO: 51) | FGQGTKL DIK (SEQ ID NO: 14) |
| LAG3-1E09_FR_1A10 | DIQMTQSP SSLSASVG DRVTITCQ AN (SEQ ID NO: 52) | QDISNY (SEQ ID NO: 53) | LNWYQQ KPGKAPK LLIY (SEQ ID NO: 12) | DAS | NLETGVPS RFSGGGSG TDFTLTINN LQPEDFAT YYC (SEQ ID NO: 54) | HHSYNTP IT (SEQ ID NO: 55) | FGQGTRLE IDIK (SEQ ID NO: 56) |
| LAG3-1E09_FR_1E05 | DIQMTQSP SSLSASVG DRVTITCR AS (SEQ ID NO: 29) | QSISSW (SEQ ID NO: 57) | LAWYQH KPGKAPK LLIY (SEQ ID NO: 58) | DAS | NLETGAPS RFSGSGSGT DFTFTIYSL QPEDVATY YC (SEQ ID NO: 59) | QQYDTVP PT (SEQ ID NO: 60) | FGPGTKV DIK (SEQ ID NO: 61) |
| LAG3-1E09_FR_1E09 | DIQMTQSP SSLSASVG DRVTITCQ AS (SEQ ID NO: 35) | QDISNY (SEQ ID NO: 53) | LNWYQQ KPGKAPN LLIY (SEQ ID NO: 62) | DAS | NLETGVPS RFSGSGSGT DFALTISSL QPEDFATY YC (SEQ ID NO: 63) | QQSDSTPI T (SEQ ID NO: 64) | FGQGTRL DIK (SEQ ID NO: 65) |

TABLE 12

Light chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_FR_1E10 | DIQMTQSPSSLSASVGDRVIITCQAS (SEQ ID NO: 66) | QDITNY (SEQ ID NO: 67) | LNWYQQKPGKAPKLLIY (SEQ ID NO: 12) | DAS | NLETGVPSRFTGSGSGTDFTFTISSLQPEDIATYHC (SEQ ID NO: 68) | QQSYSTPPYT (SEQ ID NO: 69) | FGQGTKLEIK (SEQ ID NO: 34) |
| LAG3-1E09_FR_1F03 | DIQMTQSPSSLSASVGDRVTITCQAS (SEQ ID NO: 35) | QDISNY (SEQ ID NO: 53) | LNWYQQKPGKAPKLLIY (SEQ ID NO: 12) | DAS | NLETGVPSRFSGSGSGTDFTFTISSLQPEDFATYYC (SEQ ID NO: 70) | QQSYSTPFA (SEQ ID NO: 71) | FGPGTKVEIK (SEQ ID NO: 72) |
| LAG3-1E09_FR_1G07 | DIQMTQSPSSLSASVGDRVTITCRAS (SEQ ID NO: 29) | QGISTY (SEQ ID NO: 73) | LNWYQQKPGKAPKLLIY (SEQ ID NO: 12) | DAS | NLETGVPSRFSGSGSGTDFTLTISLQPDDFALYYC (SEQ ID NO: 74) | QQSYTTPYS (SEQ ID NO: 75) | FGPGTKVEIK (SEQ ID NO: 72) |
| LAG3-1E09_CDR_1D04 | DIQMTQSPSSLSASVGDRVTITCQAS (SEQ ID NO: 35) | QDISNY (SEQ ID NO: 53) | LNWYQQKPGKAPNLLIY (SEQ ID NO: 62) | DAS | NLETGVPSRFSGSGSGTDFTLTISSLQPEDFATYYC (SEQ ID NO: 13) | QQSYITPYT (SEQ ID NO: 76) | FGQGTKLDIK (SEQ ID NO: 14) |
| LAG3-1E09_CDR_1E03 | DIQMTQSLSSLSASVGDSVTITCQAS (SEQ ID NO: 77) | QDISNY (SEQ ID NO: 53) | LNWYRQKPGKAPELLIY (SEQ ID NO: 78) | DTS | NLETGVPSRFSGSGSGTDFTLTISSLQPEDFATYYC (SEQ ID NO: 13) | QQSYSIPYT (SEQ ID NO: 80) | FGQGTKVEIK (SEQ ID NO: 81) |
| LAG3-1E09_AM_1B03 | DIQMTQSPSSLSASVGDRVTMTCQAS (SEQ ID NO: 82) | QDVSNY (SEQ ID NO: 83) | LNWYQQKPGKAPKLLIY (SEQ ID NO: 12) | DAS | NLEIGVPSRFSGSGSGTDFTFTISSLQPEDTATYYC (SEQ ID NO: 84) | QQYDHLPPYT (SEQ ID NO: 85) | FGQGTKLEIK (SEQ ID NO: 34) |
| LAG3-1E09_AM_1E09 | DIQMTQSPATLSVSPGERATLSCRAS (SEQ ID NO: 86) | QSVMNN (SEQ ID NO: 87) | LAWYQQKPGQAPRLLIY (SEQ ID NO: 88) | DAS | NRATGIPARFSGSGSGTDFTLTISRLEPEDFAVYYC (SEQ ID NO: 89) | EQYVRSPYT (SEQ ID NO: 90) | FGQGTKDIK (SEQ ID NO: 14) |
| LAG3-1E09_AM_1F09 | DIQMTQSPSSLSASVGDRVTITCQAS (SEQ ID NO: 35) | QDIRNY (SEQ ID NO: 91) | LGWYQQKPGKAPNLLIY (SEQ ID NO: 92) | DAS | TLETGVPSRFSGSGSGTDFTLAISSLQPEDFATYYC (SEQ ID NO: 93) | QQSYSTPYT (SEQ ID NO: 33) | FGQGTKLEIK (SEQ ID NO: 34) |

TABLE 13

Light chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_AM_1H07 | DIQMTQSPSSLSASVGDRVTITCQAS (SEQ ID NO: 35) | QDISNY (SEQ ID NO: 53) | LNWYQQKPGKAPKLLIY (SEQ ID NO: 12) | EAS | SLESGVPSRFSGSGSGTEFTLTINSLQPEDFATYYC (SEQ ID NO: 95) | QQSYSTPFA (SEQ ID NO: 71) | FGPGTKVEIK (SEQ ID NO: 72) |

TABLE 13-continued

Light chain variable region of selected human LAG3 antibody variants (continued)

| NAME | FR1 | CDR1 | FR2 | CDR2 | FR3 | CDR3 | FR4 |
|---|---|---|---|---|---|---|---|
| LAG3-1E09_A M_2E04 | DIQMTQSP SSLSASVG DRVTIICR AS (SEQ ID NO: 96) | QSISNY (SEQ ID NO: 97) | LNWYQQE PGKAPKLL IY (SEQ ID NO: 98) | DAS | NLESGVPSR FSGSGSGTD FTLTISSLQP EDFATYYC (SEQ ID NO: 99) | QQSYSTP YT (SEQ ID NO: 33) | FGQGTKV EIK (SEQ ID NO: 81) |
| LAG3-1E09_A M_2E09 | DIQMTQSS SSLSASVG DRVTITCQ AS (SEQ ID NO: 100) | QDITDF (SEQ ID NO: 101) | LNWYQQK PGKAPKLL IY (SEQ ID NO: 12) | DAS | NLETGIPSR FSGSGSGRE FTLTINSLQ PEDVASYY C (SEQ ID NO: 102) | QQSYTTP LT (SEQ ID NO: 103) | FGGGTKV DIK (SEQ ID NO: 104) |
| LAG3-1E09_A M_2G1 1 | DIQMTQSP SSLSASVG DRVTITCR AS (SEQ ID NO: 29) | QSISYY (SEQ ID NO: 105) | LNWYQQR PGKAPKLL IY (SEQ ID NO: 106) | DAS | NLETGVPS RFSGSGTGT EFTLTISSL QPEDFATY YC (SEQ ID NO: 107) | QQSYSTP FA (SEQ ID NO: 71) | FGPGTKV EIK (SEQ ID NO: 72) |
| LAG3-1E09_A M_2H0 1 | DIQMTQSP SSLSASVG DRVTITCQ AS (SEQ ID NO: 35) | QDISNY (SEQ ID NO: 53) | LNWYQQK PGKAPNLL IY (SEQ ID NO: 62) | DAS | TLETGVPSR FSGSGYGT DFTLTISGL QPDDFALY YC (SEQ ID NO: 108) | QQSYSTP YS (SEQ ID NO: 33) | FGPGTKV EIK (SEQ ID NO: 72) |
| LAG3-1E09_A M_2H0 6 | DIQMTQSP SSLSASVG DRVTITCQ AS (SEQ ID NO: 35) | QDISNY (SEQ ID NO: 53) | LNWYQQT PGKAPKLL IY (SEQ ID NO: 109) | DAS | NLETGVPS RFSGSGSGT DFTLTISSL QPEDFATY YC (SEQ ID NO: 13) | QQGYGTP YT (SEQ ID NO: 110) | YGQGTKL EIK (SEQ ID NO: 111) |

Example 8. Production of Selected Human Anti-LAG-3 Monoclonal Antibody Variants

8-1. Conversion of scFv Form to IgG Form

In order to convert the selected 22 monoclonal phage antibodies against LAG-3 from phage to fully human IgG form, the same process as Example 3-1 was carried out, and each plasmid DNA containing the nucleotide sequences of the heavy chain and light chain DNA was obtained and sent for sequencing (Solgent, Korea).

As a result, it was found that each of the nucleotide sequences of the heavy chain and light chain of the 22 antibody clones against LAG-3 obtained after conversion into fully IgG form is in match with the sequence of phage antibody. After that, the heavy chain and light chain plasmid DNAs of which sequence has been identified were used for producing antibodies.

8-2. Production of Anti-LAG-3 Antibody Variants

Production of the 22 antibodies, which are selected 1E09 antibody variants, was carried out in the same manner as Example 3-2. Each vector including the cloned heavy and light chains was co-transfected and expressed in animal transient expression cells, HEK-293F, and then purified by protein A affinity chromatography to determine the yield, and the protein purity and mobility were examined by SDS-PAGE analysis under reducing and non-reducing conditions.

Figure 12:
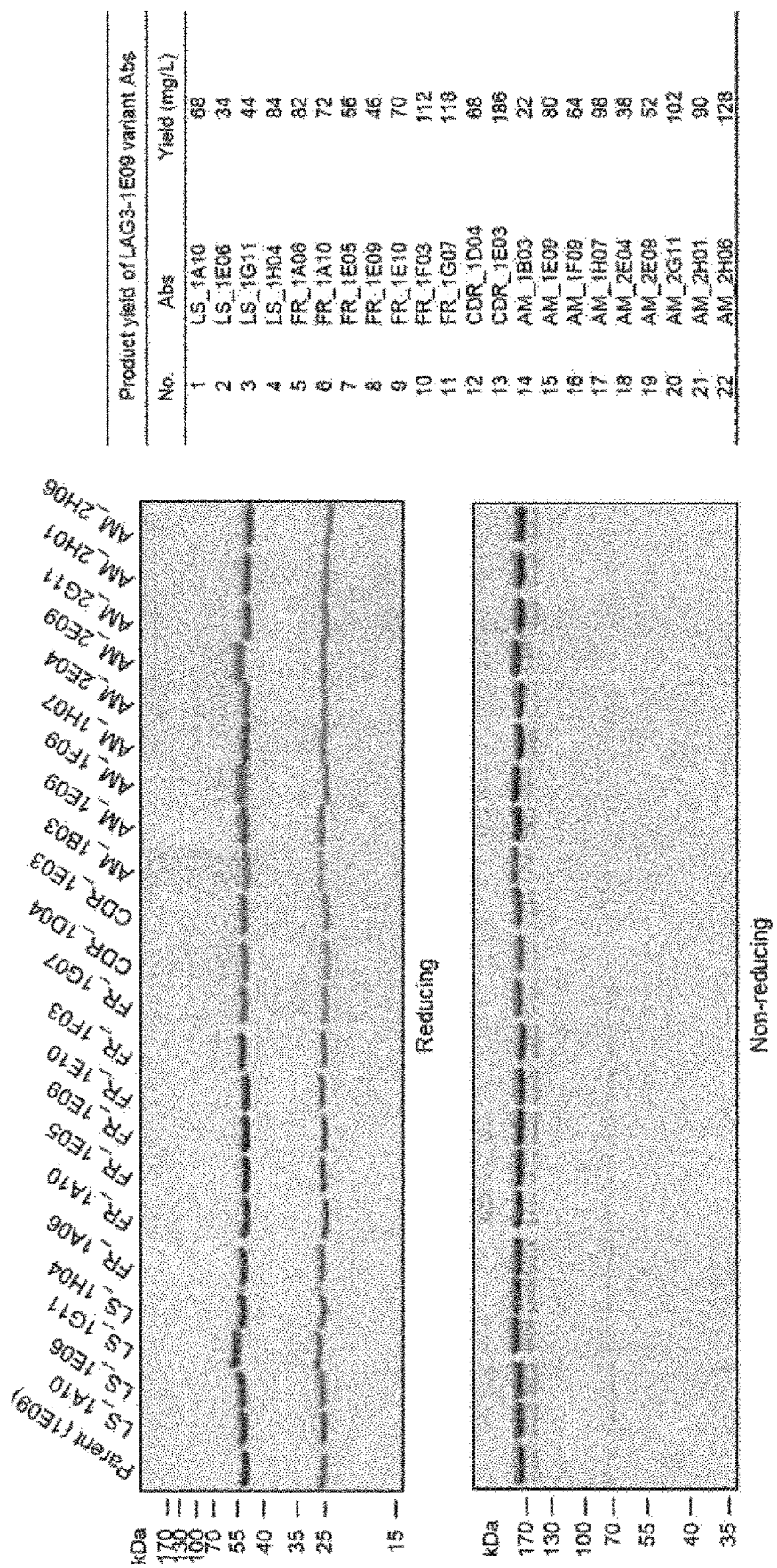
FIG. 12 shows the result of determining purity and yield of the variant antibodies selected after optimization (affinity maturation) of 1E09, in which the determination was made by SDS-PAGE at reducing or non-reducing conditions.

As a result, as shown in FIG. 12, all of the human anti-LAG-3-1E09 monoclonal antibody variants were detected at a size of 150 kDa or more under non-reducing conditions and the yield was varying from the lowest yield of 22 mg/L to the highest yield of 186 mg/L.

Example 9. Characteristics of Selected Human Anti-LAG-3 Antibody Variants

9-1. Species Cross-Reactivity of Selected Human Anti-LAG-3 Antibody Variants Binding and inter-species cross-reactivity of the 22 antibodies, which are variants of human anti-LAG-3 monoclonal antibody, against human LAG-3 antigen were determined by measuring MFI values representing antibody binding in HEK293E cells, which overexpress human, monkey or mouse LAG-3, by using CytoFLEX flow cytometer according to the methods described in Examples 4-1 and 4-2. Binding of the variant antibodies for human LAG-3 antigen, including binding of LAG-3-1E09 parent antibody, and inter-species cross-reactivity between monkey and mouse were shown in the following Table 14 by describing the values that are measured at antibody concentration of 2 µg/ml.

TABLE 14

Species cross-reactivity of selected human anti-LAG-3 antibody variants Cell Surface Binding at 2 µg/ml

| Abs | HEK23E-hLAG3 (Human) | HEK293E-MrhLAG3 (Rhesus Monkey) | HEK293E-mLAG3 (Mouse) |
|---|---|---|---|
| Parent (1E09) | Yes | Yes | Yes |
| LS_1A10 | Yes | Yes | No |
| LS_1E06 | Yes | Yes | Yes |
| LS_1G11 | Yes | Yes | Yes |
| LS_1H04 | Yes | Yes | No |

TABLE 14-continued

Species cross-reactivity of selected
human anti-LAG-3 antibody variants
Cell Surface Binding at 2 µg/ml

| Abs | HEK23E-hLAG3 (Human) | HEK293E-MrhLAG3 (Rhesus Monkey) | HEK293E-mLAG3 (Mouse) |
|---|---|---|---|
| FR_1A06 | Yes | Yes | No |
| FR_1A10 | Yes | Yes | Yes |
| FR_1E05 | Yes | Yes | No |
| FR_1E09 | Yes | Yes | No |
| FR_1E10 | Yes | Yes | Yes |
| FR_1F03 | Yes | Yes | Yes |
| FR_1G07 | Yes | Yes | Yes |
| CDR_1D04 | Yes | Yes | Yes |
| CDR_1E03 | Yes | Yes | Yes |
| AM_1B03 | Yes | Yes | No |
| AM_1E09 | Yes | Yes | No |
| AM_1F09 | Yes | Yes | No |
| AM_1H07 | Yes | Yes | No |
| AM_2E04 | Yes | Yes | No |
| AM_2E09 | Yes | Yes | Yes |
| AM_2G11 | Yes | Yes | Yes |
| AM_2H01 | Yes | Yes | Yes |
| AM_2H06 | Yes | Yes | Yes |

Figure 13:
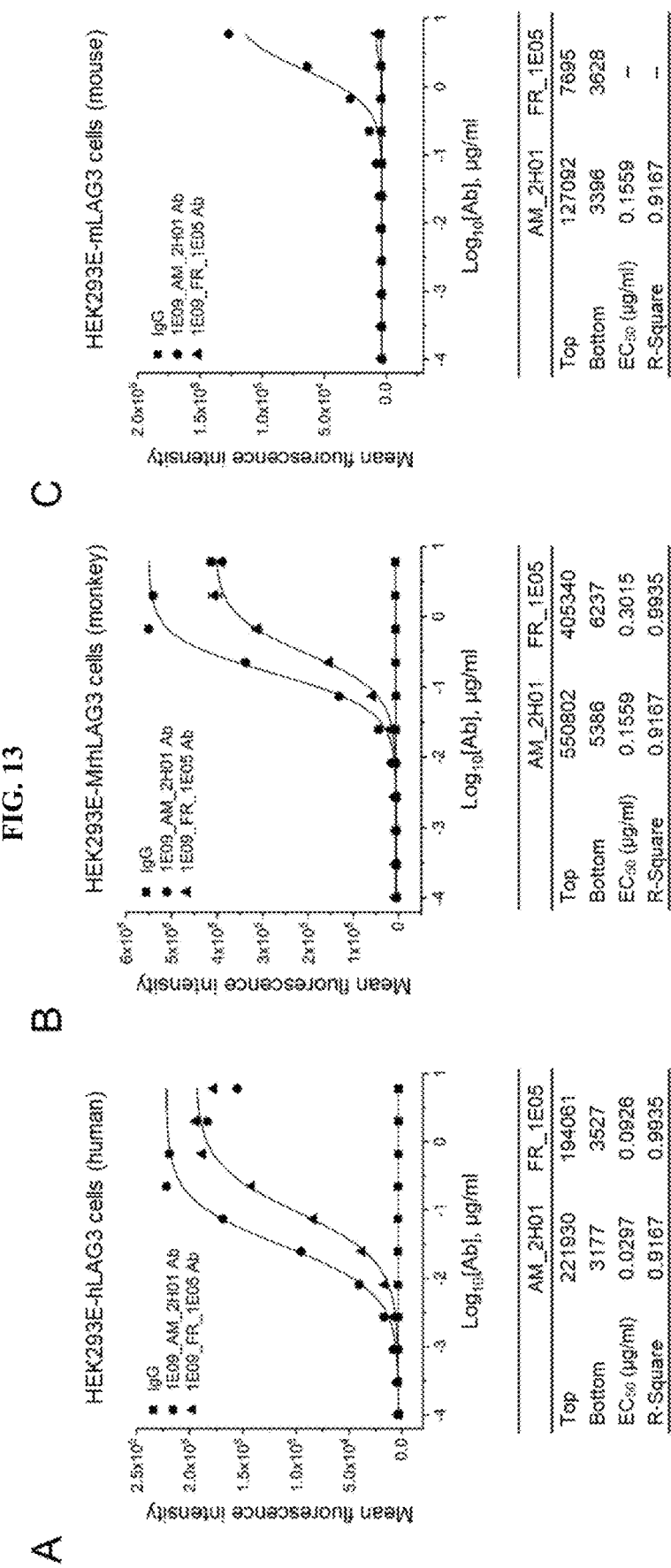
FIG. 13 shows the result of determining the cross-reactivity and binding specificity by using 1E09-AM_2H01 and 1E09-FR_1E05 as a variant antibody and cells in which human LAG-3 (A), monkey LAG-3 (B) or mouse LAG-3 (C) is overexpressed.
Figure 14C:
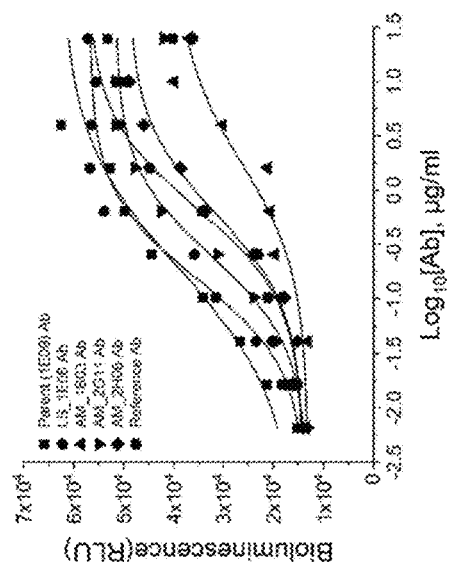
FIG. 14 shows the result demonstrating that T cell activity is enhanced by variant antibodies as they inhibit the forming of LAG-3/MHC class II complex.
Figure 14B:
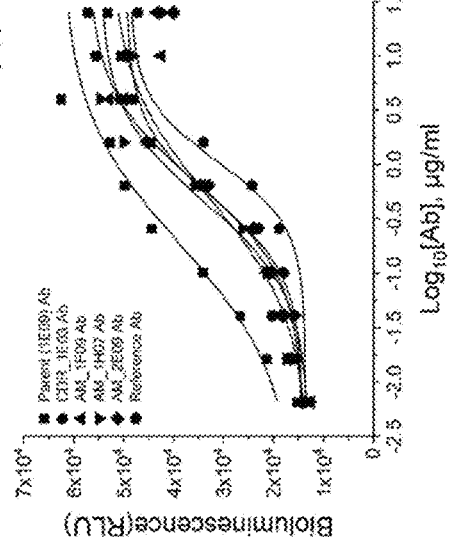
Figure 14A:
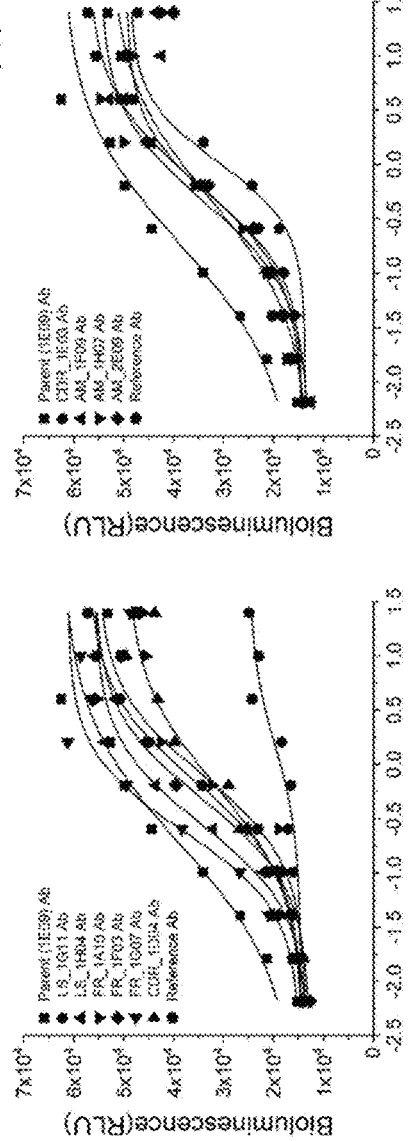
Figure 14D:
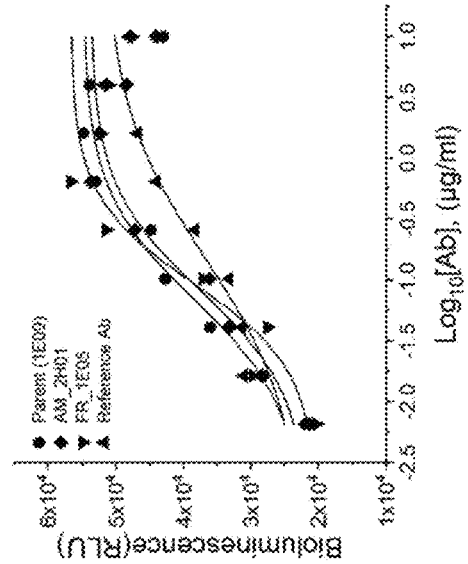
Figure 15A:
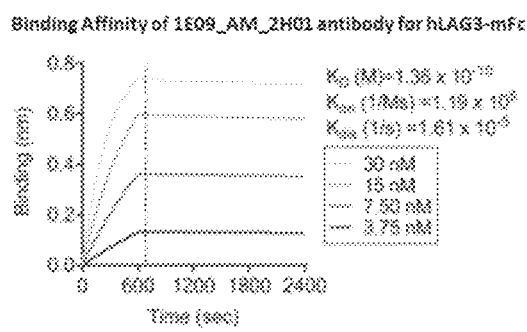
FIG. 15 shows the result of measuring the binding affinity of the variant antibodies for human, monkey, or mouse LAG-3 protein and kinetic constant of the binding, in which the measurement was carried out by using the octet system.
Figure 15D:
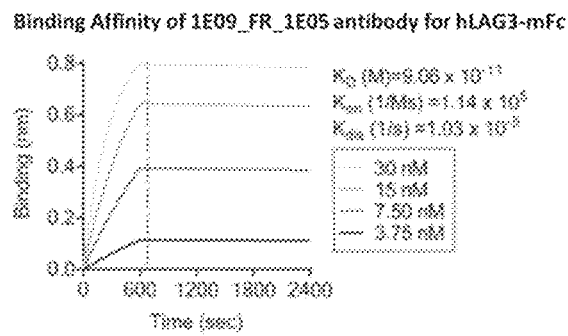
Figure 15B:
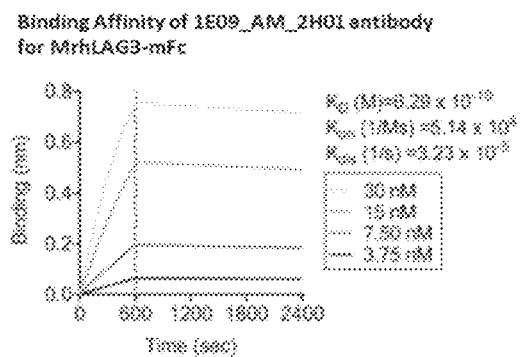
Figure 15E:
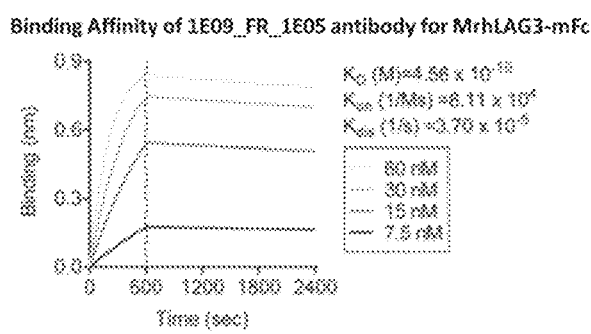
Figure 15C:
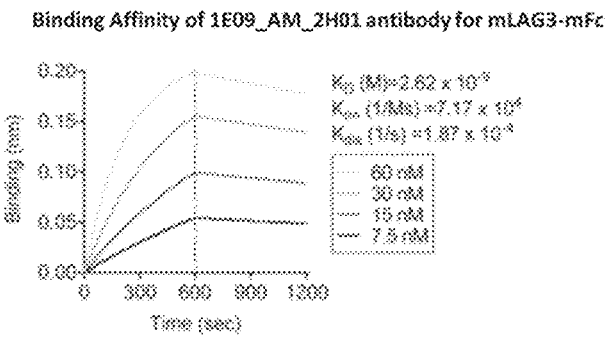

Furthermore, in case of 1E09_AM_2H01 and 1E09_FR_1E05 antibodies among the 22 antibodies, the cell binding capacity is the same as $EC_{50}$ values that are shown in FIG. 13.

9-2. Evaluation of Activity of Selected Human Anti-LAG-3 Monoclonal Antibody Variant The test for evaluating the activity of the 22 antibodies, i.e., human anti-LAG-3 monoclonal antibody 1E09 variants, was carried out in the same manner as Example 5-2 by using LAG-3/MHC class II blockade bioassay kit. After culturing APC cell line, in which MHC class II is overexpressed, for at least 16 hours in a 96-well plate, it was treated with each antibody which has been prepared by ×1/2.5 serial dilution starting from 25 µg/ml (A of FIG. 14) or 10 µg/ml (B of FIG. 14) antibody concentration, and co-cultured for 6 hours with acting cell line overexpressing human LAG-3. Inhibition recovery level by the antibody was determined by measuring the luminescence intensity resulting from degradation of a substrate by luciferase using a spectrophotometer (GLO-MAX® Discover System, Model #GM3000, Promega). Among the 22 antibodies including LAG-3-1E09 parent antibody, for example, 15 antibodies showed the activity of recovering, in a concentration gradient dependent manner, the signal of acting cells (i.e., Jurkat T cells) which have been reduced due to forming of LAG-3/MHC class II complex (FIG. 14). Compared to the control antibody (i.e., reference), 12 antibodies of the present invention were shown to exhibit better activity, and $EC_{50}$ values representing the inhibition recovery capacity of each antibody are given in Table 15.

TABLE 15

Determination of in vitro efficacy of selected human
anti-LAG-3 antibody variants

| Abs | Top | bottom | $EC_{50}$ (µg/ml) | R-Square |
|---|---|---|---|---|
| LAG3/MHC class II Blockade bioassay (A of FIG. 13) | | | | |
| Parent (1E09) | 62520 | 15050 | 0.1864 | 0.8975 |
| LS 1G11 | 24780 | 14490 | 1.5117 | 0.8773 |
| LS_1H04 | 55840 | 13050 | 0.2840 | 0.9590 |
| FR 1A10 | 55270 | 13420 | 0.8108 | 0.9028 |

TABLE 15-continued

Determination of in vitro efficacy of selected human
anti-LAG-3 antibody variants

| Abs | Top | bottom | $EC_{50}$ (µg/ml) | R-Square |
|---|---|---|---|---|
| FR_1F03 | 55910 | 12690 | 0.4854 | 0.9582 |
| FR_1G07 | 61250 | 14650 | 0.2419 | 0.9292 |
| CDR_1D04 | 49540 | 13940 | 0.6555 | 0.9710 |
| CDR_1E03 | 48700 | 13570 | 1.0594 | 0.9741 |
| AM_1F09 | 52880 | 12600 | 0.4877 | 0.8923 |
| AM_1H07 | 54730 | 12810 | 0.4484 | 0.8925 |
| AM_2E09 | 49470 | 14130 | 0.4817 | 0.9301 |
| LS_1E06 | 56800 | 13570 | 0.1510 | 0.8312 |
| AM_1B03 | 39910 | 13010 | 1.8245 | 0.9024 |
| AM_2G11 | 51620 | 13210 | 0.2459 | 0.9436 |
| AM 2H06 | 49020 | 13910 | 0.6061 | 0.8905 |
| Reference | 57200 | 14010 | 0.7160 | 0.9887 |
| LAG3/MHC class II Blockade bioassay (B of FIG. 13) | | | | |
| Parent (1E09) | 54820 | 21910 | 0.0688 | 0.8267 |
| AM 2H01 | 53740 | 21300 | 0.0822 | 0.8373 |
| FR_1E05 | 56655 | 20280 | 0.0938 | 0.8493 |
| Reference | 51815 | 21865 | 0.1540 | 0.9388 |

9-3. Determination of Affinity of Selected Human Anti-LAG-3 Monoclonal Antibody Variants for Antigen Affinity of the selected human anti-LAG-3 monoclonal antibody variants for antigen was determined by measuring, according to the same method as Example 4-3 using human LAG-3 (hLAG-3-mFc), monkey LAG-3 (MrhLAG-3-mFc), and mouse LAG-3 (mLAG-Fc) antigens as a recombinant fusion protein, the equilibrium dissociation constant ($K_D$) using OCTET® $QK^e$ (Fortebio Inc. USA) analyzer.

Figure 16:
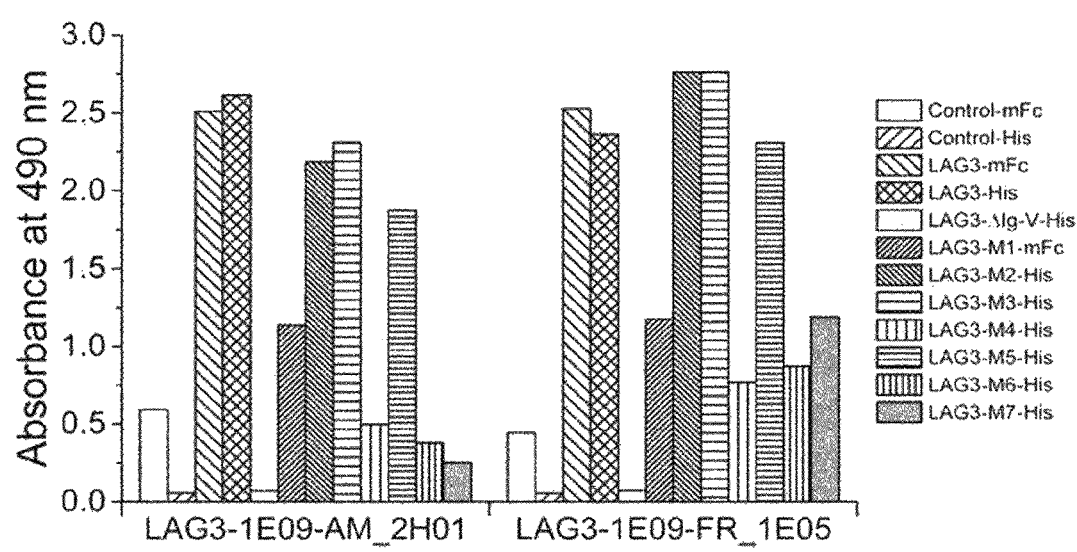
FIG. 16 shows the result of determining the binding specificity of 1E09-AM_2H01 and 1E09-FR_1E05, which are a LAG-3-1E09 variant antibody, using LAG-3-mFc or -His fused proteins in which Ig-V domain of the extracellular domain of LAG-3 is cleaved (ΔIg-V) or a specific or non-specific amino acid within Ig-V domain is substituted with other amino acid (see, A and B of FIG. 8), in which the determination was made by ELISA.

As a result, it was found that, among the human anti-LAG-3 monoclonal antibody 1E09 variants, 1E09-AM_2H01 (A to C of FIG. 15) and 1E09-FR_1E05 (D and E of FIG. 15), for example, have antigen binding capacity ($K_D$) of 0.136 nM and 0.0906 nM, respectively, for human LAG-3 antigen, or 0.629 nM and 0.456 nM, respectively, for monkey LAG-3 antigen. For mouse LAG-3 antigen, 1E09-AM_2H01 shows the antigen binding capacity of 2.62 nM but 1E09-FR_1E05 did not show any binding. 9-4. Determination of antigen binding site (epitope) of selected human anti-LAG-3 monoclonal antibody variants To determine the antigen binding site of human anti-LAG-3 monoclonal antibody 1E09 variants, ELISA was carried out by using recombinant LAG-3 mutant variants, in which Ig-V domain in the extracellular domain of LAG-3 has been cleaved (ΔIg-V) or a specific or non-specific amino acid is substituted with other amino acid (M1 to M7) as it is described in Example 4-4 (FIG. 16).

As a result, among the variant antibodies of human anti-LAG-3 monoclonal antibody 1E09, 1E09-AM_2H01 and 1E09-FR_1E05, for example, bind to Ig-V domain in LAG-3 extracellular domain, which is similar to the case of parent antibody 1E09 (C of FIG. 8), and, specifically, they bind to M1, M4, M6, M7 sites in LAG-3 Ig-V domain. Accordingly, it was recognized that they have a conformational epitope showing binding to $^{52}DL^{53}$, $^{107}$GGLRS-GRLPLQ$^{117}$ (SEQ ID NO: 9), $^{137}$R, and $^{150}$AVHLRDRALSCR$^{161}$ (SEQ ID NO: 31) of WT LAG-3 (FIG. 16).

A sequence listing electronically submitted with the present application on Oct. 29, 2020 as an ASCII text file named 20201029_Q39820GR12_TU_SEQ, created on Oct. 29, 2020 and having a size of 47,000 bytes, is incorporated herein by reference in its entirety.

What is claimed is:

1. A monoclonal antibody or an antigen-binding fragment thereof specifically binding to lymphocyte-activation gene 3 (LAG-3), comprising:
   a heavy chain variable region comprising:
   heavy chain CDR1 represented by SEQ ID NO: 1 or SEQ ID NO: 27;
   heavy chain CDR2 represented by SEQ ID NO: 2; and
   heavy chain CDR3 represented by SEQ ID NO: 3; and
   a light chain variable region comprising:
   light chain CDR1 represented by SEQ ID NO: 8, SEQ ID NO: 53 or SEQ ID NO: 57;
   light chain CDR2 represented by Asp Ala Ser; and
   light chain CDR3 represented by SEQ ID NO: 10, SEQ ID NO: 33 or SEQ ID NO: 60.

2. The monoclonal antibody or the antigen-binding fragment thereof according to claim 1, comprising:
   the heavy chain variable region comprising:
   the heavy chain CDR1 represented by SEQ ID NO: 1;
   the heavy chain CDR2 represented by SEQ ID NO: 2; and
   the heavy chain CDR3 represented by SEQ ID NO: 3; and
   the light chain variable region comprising:
   the light chain CDR1 represented by SEQ ID NO: 8;
   the light chain CDR2 represented by Asp Ala Ser; and
   the light chain CDR3 represented by SEQ ID NO: 10.

3. The monoclonal antibody or the antigen-binding fragment thereof according to claim 1, comprising:
   the heavy chain variable region comprising:
   the heavy chain CDR1 represented by SEQ ID NO: 27;
   the heavy chain CDR2 represented by SEQ ID NO: 2; and
   the heavy chain CDR3 represented by SEQ ID NO: 3; and
   the light chain variable region comprising:
   the light chain CDR1 represented by SEQ ID NO: 53;
   the light chain CDR2 represented by Asp Ala Ser; and
   the light chain CDR3 represented by SEQ ID NO: 33.

4. The monoclonal antibody or the antigen-binding fragment thereof according to claim 1, comprising:
   the heavy chain variable region comprising:
   the heavy chain CDR1 represented by SEQ ID NO: 1;
   the heavy chain CDR2 represented by SEQ ID NO: 2; and
   the heavy chain CDR3 represented by SEQ ID NO: 3; and
   the light chain variable region comprising:
   the light chain CDR1 represented by SEQ ID NO: 57;
   the light chain CDR2 represented by Asp Ala Ser; and
   the light chain CDR3 represented by SEQ ID NO: 60.

5. The monoclonal antibody or the antigen-binding fragment thereof according to claim 2, comprising:
   the heavy chain variable region represented by the amino acid sequence of SEQ ID NO: 114; and
   the light chain variable region represented by the amino acid sequence of SEQ ID NO: 115.

6. The monoclonal antibody or the antigen-binding fragment thereof according to claim 3, comprising:
   the heavy chain variable region represented by the amino acid sequence of SEQ ID NO: 116; and
   the light chain variable region represented by the amino acid sequence of SEQ ID NO: 117.

7. The monoclonal antibody or the antigen-binding fragment thereof according to claim 4, comprising:
   the heavy chain variable region represented by the amino acid sequence of SEQ ID NO: 118; and
   the light chain variable region represented by the amino acid sequence of SEQ ID NO: 119.

8. The monoclonal antibody or the antigen-binding fragment thereof according to claim 1, wherein the monoclonal antibody is selected from the group consisting of fully human antibodies, humanized antibodies, chimeric antibodies, and recombinant antibodies.

9. The monoclonal antibody or the antigen-binding fragment thereof according to claim 1, wherein the antigen-binding fragment is selected from the group consisting of scFv (single chain variable fragment), dsFv, Fab, F(ab') and F(ab')$_2$ which bind to LAG-3.

10. A polynucleotide encoding the heavy chain variable region and light chain variable region of the monoclonal antibody or the antigen-binding fragment thereof of claim 1.

11. An expression vector comprising the polynucleotide of claim 10.

12. A cell transformed with the expression vector of claim 11.

13. A method for producing a monoclonal antibody or an antigen-binding fragment thereof specifically binding to LAG-3, the method comprising:
   culturing the transformed cell of claim 12 to prepare a culture broth; and
   purifying the monoclonal antibody or the antigen-binding fragment thereof from the culture broth.

14. A drug conjugate having a drug conjugated to the monoclonal antibody or the antigen-binding fragment thereof of claim 1.

15. A chimeric antigen receptor (CAR) protein comprising:
   the monoclonal antibody or the antigen-binding fragment thereof of claim 1;
   a transmembrane domain; and
   an intracellular signaling domain that is characterized to bring about T cell activation upon binding of the monoclonal antibody or the antigen-binding fragment thereof to an antigen.

16. A multi-specific antibody including the monoclonal antibody or the antigen-binding fragment thereof of claim 1.

* * * * *